(12) United States Patent
Van Der Eycken et al.

(10) Patent No.: US 9,771,344 B2
(45) Date of Patent: Sep. 26, 2017

(54) PELORUSIDE ANALOGS

(71) Applicant: Universiteit Gent, Ghent (BE)

(72) Inventors: Johan Van Der Eycken, Ninove (BE); Gert Smans, Rheinfelden (DE); Jelle Cornelus, Zelzate (BE); Dries Van Den Bossche, Ghent (BE); Nick Jacobs, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 15/036,743

(22) PCT Filed: Nov. 28, 2014

(86) PCT No.: PCT/EP2014/075903
§ 371 (c)(1),
(2) Date: May 13, 2016

(87) PCT Pub. No.: WO2015/079009
PCT Pub. Date: Jun. 4, 2015

(65) Prior Publication Data
US 2016/0304483 A1  Oct. 20, 2016

(30) Foreign Application Priority Data

Nov. 28, 2013  (EP) .................... 13194845

(51) Int. Cl.
| C07D 313/00 | (2006.01) |
| A61K 31/365 | (2006.01) |
| A61K 45/06 | (2006.01) |

(52) U.S. Cl.
CPC .......... *C07D 313/00* (2013.01); *A61K 31/365* (2013.01); *A61K 45/06* (2013.01)

(58) Field of Classification Search
None
See application file for complete search history.

(56) References Cited

U.S. PATENT DOCUMENTS 6,353,019 B1   3/2002   Boyd et al.

FOREIGN PATENT DOCUMENTS

| WO | 2005/023792 A2 | 3/2005 |
| WO | 2011/036299 A1 | 3/2011 |

OTHER PUBLICATIONS

Hood et al. (2002) "Peloruside A, A Novel Antimitotic Agent with Paclitaxel-like Microtubulestabilizing Activity," Cancer Res. 62:3356-3360.
International Search Report with Written Opinion corresponding to International Patent Application No. PCT/EP2014/075903, mailed Mar. 30, 2015.
Gaitanos et al. (2004) "Peloruside a does not bind to the taxoid site on beta-tubulin and retains its activity in multidrug-resistant cell lines," Cancer Res. 64:5063-5067.
Hamel et al. (2006) "Synergistic effects of peloruside A and laulimalide with taxoid site drugs, but not with each other, on tubulin assembly," Mol. Pharmacol. 70:1555-1564.
Robbins et al.: Eds. (1976) Basic Pathology. 2nd Ed. W.B. Saunders Company. pp. 68-79.
Singh et al. (2009) "Peloruside B, A Potent Antitumor Macrolide from the New Zealand Marine Sponge Mycale hentscheli: Isolation, Structure, Total Synthesis, and Bioactivity," J. Org. Chem. 75:2-10.
West et al. (2000) "Peloruside A: A Potent Cytotoxic Macrolide Isolated from the New Zealand Marine Sponge *Mycale* sp.," J. Org. Chem. 65:445-449.

*Primary Examiner* — Samantha Shterengarts
(74) *Attorney, Agent, or Firm* — Lathrop Gage LLP; James H. Velema

(57) ABSTRACT

The present invention provides new therapeutic compounds for treatment of diseases caused or influenced by microtubule stability, such as proliferative diseases. The compounds are phenyl-analogs of the naturally occurring peloruside. The analogs are easier to synthesize, and hence open up the possibility to produce said compounds in large quantities for therapeutic use.

20 Claims, 6 Drawing Sheets

A

B

C

D

PELORUSIDE ANALOGS

RELATED APPLICATIONS

This application is a 35 U.S.C. §371 national stage filing of international patent application number PCT/EP2014/075903, filed Nov. 28, 2014, which claims priority to European patent application number 13194845.7, filed Nov. 28, 2013, each of which is incorporated herein by reference in its entirety.

FIELD OF THE INVENTION

The present invention is situated in the field of medical treatment, more particularly in the field of treatment of microtubule-related disorders, particularly cancer treatment, using analogs of the natural compound peloruside with improved treatment characteristics. The invention relates to said peloruside analogs as such, and methods involving the use of said peloruside analogs in treatment.

BACKGROUND OF THE INVENTION

New and potent drugs are urgently needed to inhibit uncontrolled growth, invasion and metastasis. The majority of available treatments or therapeutics are limited towards inhibition of the growth of the tumour. Microtubule inhibitors block the mitotic spindle and function of the cytoplasmic microtubule complex and therefore form an interesting alternative for drug development for treating cancer, since they inhibit proliferation, invasion and metastasis. Two examples of such drugs that have been used with success are paclitaxel (Taxol®) and docetaxel (Taxotere®), which have been used to treat roughly one million of patients in the 10 years since they were first approved as anti-cancer drugs. Paclitaxel, docetaxel and vinca alkaloids like vinblastine are compounds interacting with the mitotic spindle by binding to β-tubulin. They are used as therapeutics in standard chemotherapy regimens and in combination with new drugs like the HER2 targeting antibody trastuzumab. But toxicity, drug resistance, and complex galenic formulations are restricting their clinical use in cancer therapy. Further drawbacks of e.g. paclitaxel are its low solubility in water (needs to be dissolved in Cremophor EL (polyoxyethylated castor oil) which causes hypersensitivity reactions), high hydrophobicity, adhesion to plastic tubing inner surfaces complicating administration, creating therapy resistance, etc. . . .

Thus, new tubulin targeting antimitotic agents with better tolerability and efficacy against (late-stage resistant) tumors are urgently needed. The present invention provides solutions to the above-identified problems by designing peloruside-derivatives as new therapeutic agents.

SUMMARY OF THE INVENTION

The present invention follows from a study of peloruside. Peloruside was first discovered in marine sponges in New Zealand, and comes mainly in two forms, Peloruside A (West et al. *J. Org. Chem.*, 2000, 65, 445-449) and B (Singh et al. *J. Org. Chem.* 2009, 75, 2-10):

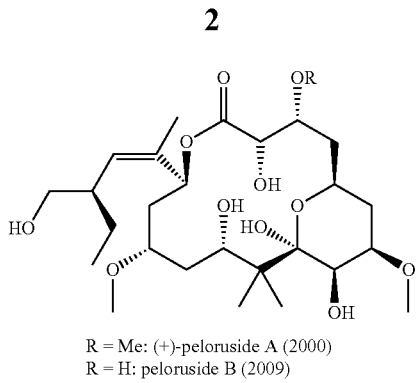

R = Me: (+)-peloruside A (2000)
R = H: peloruside B (2009)

Peloruside functions as an antitumor agent by promoting tubulin polymerization and interfering with microtubule dynamics, which causes arrest of the cell cycle in the $G_2$-M phase, followed by apoptosis (Hood et al. *Cancer Res.* 2002, 62, 3356-3360), even at nanomolar concentrations. This mode of action is similar to that of paclitaxel. Peloruside however is less susceptible than paclitaxel to multidrug resistance, arising from overexpression of the P-glycoprotein (Gaitanos et al. *Cancer Res.*, 2004, 64, 5063-5067). Moreover, it is proven that peloruside and paclitaxel do not compete for the same binding site. Hence, peloruside conserves its cytotoxicity in cell lines that are affected by mutations of the β-tubuline gene, causing a conformational change of the taxoid binding site. Furthermore, it is proven that peloruside exhibits synergy with other microtubule stabilizing drugs like taxol (Hamel et al. *Cancer Chemoth. Pharm.*, 2006, 70, 1555-1564).

The biggest drawback of using peloruside is that it is only found in milligram quantities in a specific species of sea sponges with low natural abundance.

The inventors designed peloruside analogs by replacing the pyranose moiety with a phenyl moiety and could determine that its activity as a microtubule inhibitor was comparable to that of Paclitaxel. On a weight per volume base the peloruside analogs are at least as potent as paclitaxel in their ability to disturb the cytoplasmic microtubule complex. The smaller molecular weight of the former versus the latter may be associated with better penetration through the cell membrane, with reduced aspecific cytotoxicity and escape from resistance mechanisms. Adhesion to plastic tubing inner surfaces, which can complicate paclitaxel administration, also seems to be reduced.

By using a phenyl ring to replace the pyranose ring, the number of stereocenters is reduced from 10 to 6 and hence also the synthetic complexity is reduced, while retaining the biological activity.

The invention therefore provides compounds of Formula I, and the stereoisomers, prodrugs, tautomers, racemates, salts, hydrates, or solvates thereof,

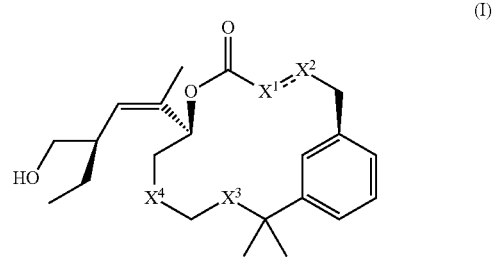

(I)

wherein

X$^1$ is CR$^{1a}$R$^{1b}$, X$^2$ is CR$^{2a}$R$^{2b}$, X$^3$ is CR$^{3a}$R$^{3b}$, X$^4$ is CR$^{4a}$R$^{4b}$, wherein R$^{1a}$, R$^{2a}$, R$^{3a}$, and R$^{4a}$ are each independently selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group independently being optionally substituted with one or more substituent(s) each independently selected from hydroxyl, halogen, C$_{1-6}$alkyl and C$_{1-6}$alkoxy; and R$^{1b}$, R$^{2b}$, R$^{3b}$, and R$^{4b}$ each independently are selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group independently being optionally substituted with one or more substituent(s) each independently selected from hydroxyl, halogen, C$_{1-6}$alkyl and C$_{1-6}$alkoxy; or R$^{1a}$ and R$^{1b}$, or R$^{2a}$ and R$^{2b}$, or R$^{3a}$ and R$^{3b}$, or R$^{4a}$ and R$^{4b}$ taken together represent an oxo (=O) group;

wherein the bond represented by a dashed and solid line represents a single bond or a double bond and in case of a double bond, R$^{1b}$ and R$^{2b}$ are absent and at least one of R$^{1a}$ and R$^{2a}$ is not OH or —NR$^{10}$R$^{11}$; and R$^{10}$ and R$^{11}$ are each independently selected from hydrogen and C$_{1-6}$alkyl; and wherein:

when R$^{1a}$, R$^{2a}$, R$^{3a}$ or R$^{4a}$ is hydroxyl, the corresponding R$^{1b}$, R$^{2b}$, R$^{3b}$ or R$^{4b}$ is not hydroxyl, is not —NR$^{10}$R$^{11}$, is not halogen, or is not C$_{1-6}$alkoxy, when R$^{1a}$, R$^{2a}$, R$^{3a}$ or R$^{4a}$ is —NR$^{10}$R$^{11}$, the corresponding R$^{1b}$, R$^{2b}$, R$^{3b}$ or R$^{4b}$ is not hydroxyl, is not —NR$^{10}$R$^{11}$, is not halogen, or is not C$_{1-6}$alkoxy, when R$^{1a}$, R$^{2a}$, R$^{3a}$ or R$^{4a}$ is halogen, the corresponding R$^{1b}$, R$^{2b}$, R$^{3b}$ or R$^{4b}$ is not hydroxyl, or is not —NR$^{10}$R$^{11}$, when R$^{1b}$, R$^{2b}$, R$^{3b}$ or R$^{4b}$ is hydroxyl, the corresponding R$^{1a}$, R$^{2a}$, R$^{3a}$ or R$^{4a}$ is not hydroxyl, is not —NR$^{10}$R$^{11}$, is not halogen, or is not C$_{1-6}$alkoxy, and when R$^{1b}$, R$^{2b}$, R$^{3b}$ or R$^{4b}$ is —NR$^{10}$R$^{11}$, the corresponding R$^{1a}$, R$^{2a}$, R$^{3a}$ or R$^{4a}$ is not hydroxyl, is not —NR$^{10}$R$^{11}$, is not halogen, or is not C$_{1-6}$alkoxy.

when R$^{1b}$, R$^{2b}$, R$^{3b}$ or R$^{4b}$ is halogen, the corresponding R$^{1a}$, R$^{2a}$, R$^{3a}$ or R$^{4a}$ is not hydroxyl, or is not —NR$^{10}$R$^{11}$, Preferably, the invention provides compounds of Formula I, and the stereoisomers, prodrugs, tautomers, racemates, salts, hydrates, or solvates thereof,

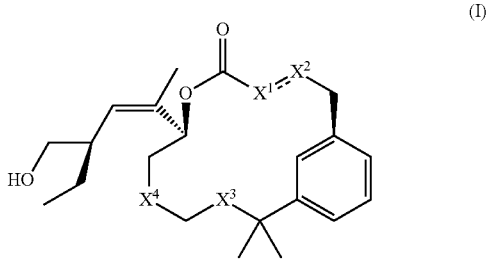

(I)

wherein:

X$^1$ is CR$^{1a}$R$^{1b}$, X$^2$ is CR$^{2a}$R$^{2b}$, X$^3$ is CR$^{3a}$R$^{3b}$, X$^4$ is CR$^{4a}$R$^{4b}$, and wherein:

R$^{1a}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy;

R$^{2a}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy, R$^{3a}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy R$^{4a}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy; and wherein:

R$^{1b}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy, R$^{2b}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy, R$^{3b}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group being independently optionally substituted with one or more substituent(s) each independently selected from hydroxyl, halogen, C$_{1-6}$alkyl and C$_{1-6}$alkoxy, R$^{4b}$ is selected from hydrogen, hydroxyl, halogen, and a group selected from —NR$^{10}$R$^{11}$, C$_{1-6}$alkyl, C$_{2-6}$alkenyl, C$_{2-6}$alkynyl, C$_{6-10}$aryl, C$_{6-10}$arylC$_{1-6}$alkyl and C$_{1-6}$alkoxy, each group independently being independently optionally substituted with one or more substituent(s) each independently selected from hydroxyl, halogen, C$_{1-6}$alkyl and C$_{1-6}$alkoxy;

or wherein R$^{1a}$ and R$^{1b}$, or R$^{2a}$ and R$^{2b}$, or R$^{3a}$ and R$^{3b}$, or R$^{4a}$ and R$^{4b}$ taken together represent an oxo (=O) group; and wherein the bond represented by a dashed and solid line represents a single bond or a double bond and wherein in case of a double bond, R$^{1b}$ and R$^{2b}$ are absent and at least one of R$^{1a}$ and R$^{2a}$ is not OH or —NR$^{10}$R$^{11}$; and wherein:

R$^{10}$ and R$^{11}$ are each independently selected from hydrogen and C$_{1-6}$alkyl; and wherein:

when R$^{1a}$, R$^{2a}$, R$^{3a}$ or R$^{4a}$ is hydroxyl, the corresponding R$^{1b}$, R$^{2b}$, R$^{3b}$ or R$^{4b}$ is not hydroxyl, is not —NR$^{10}$R$^{11}$, is not halogen, or is not C$_{1-6}$alkoxy, when $R^{1a}$, $R^{2a}$, $R^{3a}$ or $R^{4a}$ is —$NR^{10}R^{11}$, the corresponding $R^{1b}$, $R^{2b}$, $R^{3b}$ or $R^{4b}$ is not hydroxyl, is not —$NR^{10}R^{11}$, is not halogen, or is not $C_{1-6}$alkoxy, when $R^{1a}$, $R^{2a}$, $R^{3a}$ or $R^{4a}$ is halogen, the corresponding $R^{1b}$, $R^{2b}$, $R^{3b}$ or $R^{4b}$ is not hydroxyl, or is not —$NR^{10}R^{11}$, when $R^{1b}$, $R^{2b}$, $R^{3b}$ or $R^{4b}$ is hydroxyl, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy, and when $R^{1b}$, $R^{2b}$, $R^{3b}$ or $R^{4b}$ is —$NR^{10}R^{11}$, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy.

when $R^{1b}$, $R^{2b}$, $R^{3b}$ or $R^{4b}$ is halogen, the corresponding $R^{1a}$, $R^{2a}$, $R^{3a}$ or $R^{4a}$ is not hydroxyl, or is not —$NR^{10}R^{11}$, Preferably, in the structures of general formula I as defined above, $R^{1b}$, $R^{2b}$, $R^{3b}$, and $R^{4b}$ each independently are selected from hydrogen and halogen and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy; or wherein $R^{1a}$ and $R^{1b}$, and/or $R^{2a}$ and $R^{2b}$, and/or $R^{3a}$ and $R^{3b}$, and/or $R^{4a}$ and $R^{4b}$ taken together represent an oxo (=O) group.

In a preferred embodiment, in the structures of general formula I as defined above, said $R^{1b}$, $R^{2b}$, $R^{3b}$, and $R^{4b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy.

In a preferred embodiment, in the structures of general formula I as defined above, said $R^{1b}$, $R^{2b}$, and $R^{3b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy, and wherein $R^{4a}$ and $R^{4b}$ taken together represent an oxo (=O) group.

In a preferred embodiment, the invention provides compounds having structural Formula Ia, and the stereoisomers, prodrugs, tautomers, racemates, salts, hydrates, or solvates thereof:

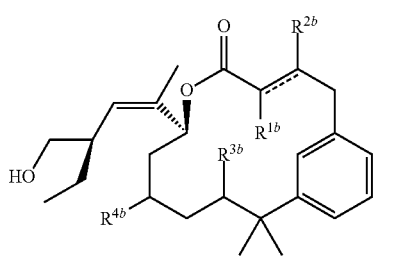
(Ia)

wherein $R^{1b}$, $R^{2b}$, $R^{3b}$, and $R^{4b}$ have the same meaning as defined above.

In another preferred embodiment, the invention provides compounds having structural Formula Ib, Ic or Id, and the stereoisomers, prodrugs, tautomers, racemates, salts, hydrates, or solvates thereof:

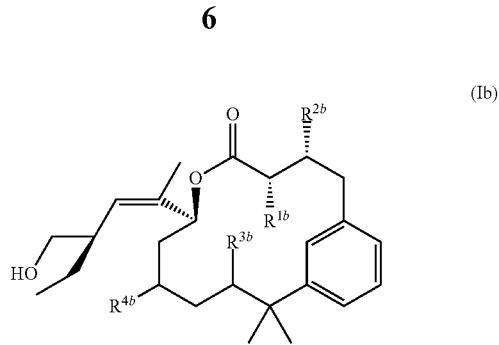
(Ib)

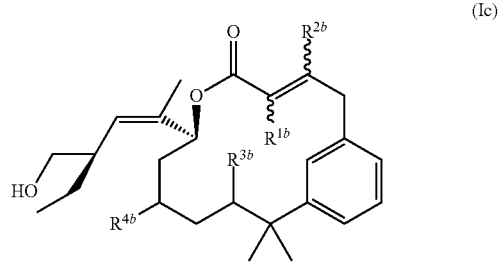
(Ic)

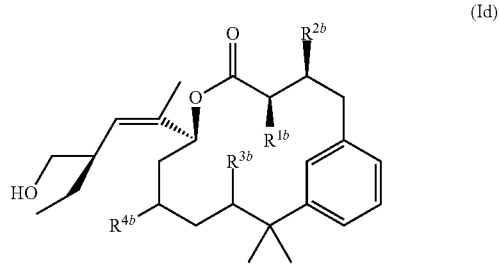
(Id)

wherein $R^{1b}$, $R^{2b}$, $R^{3b}$, and $R^{4b}$ have the same meaning as defined above. The double bond in structure Ic can have the Z- or E-geometry.

In another preferred embodiment, the invention provides compounds having structural Formula Ie, If, or Ig, and the stereoisomers, prodrugs, tautomers, racemates, salts, hydrates, or solvates thereof:

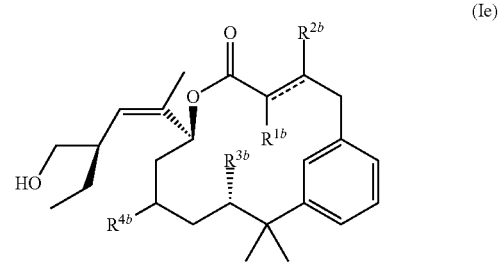
(Ie)

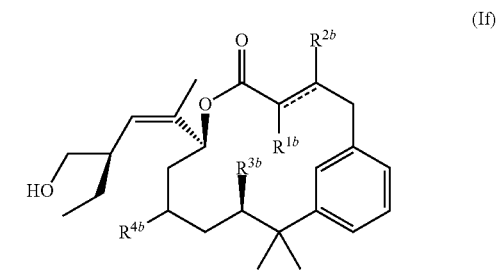
(If)

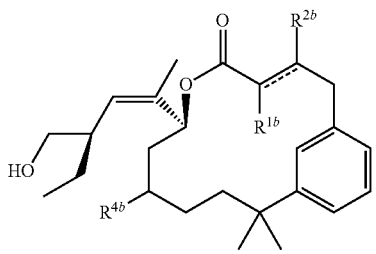
(Ig)

wherein $R^{1b}$, $R^{2b}$, $R^{3b}$, and $R^{4b}$ have the same meaning as defined above. Preferably, the bond represented by a dashed and solid line represents a single bond and $R^{1b}$ and $R^{2b}$ are positioned as in formula Ib or Id. Alternatively the bond represented by a dashed and solid line represents a double bond.

In another embodiment, the invention provides compounds having structural Formula Ih, Ii, or Ij, and the stereoisomers, prodrugs, tautomers, racemates, salts, hydrates, or solvates thereof:

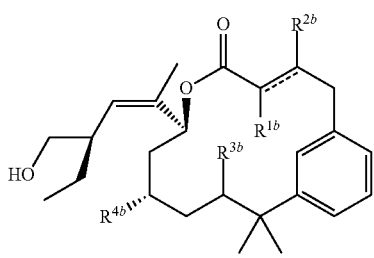
(Ih)

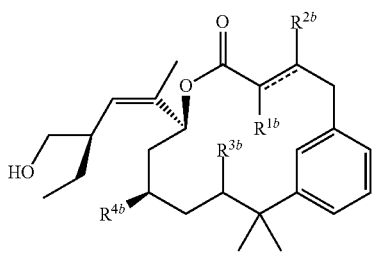
(Ii)

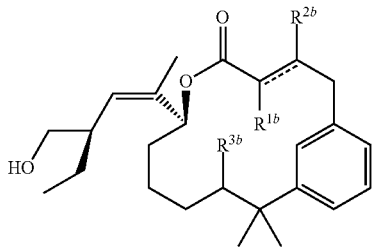
(Ij)

wherein $R^{1b}$, $R^{2b}$, $R^{3b}$, and $R^{4b}$ have the same meaning as defined above. Preferably, the bond represented by a dashed and solid line represents a single bond and $R^{1b}$ and $R^{2b}$ are positioned as in formula Ib or Id. Alternatively the bond represented by a dashed and solid line represents a double bond.

Preferably, $R^{3b}$ and $R^{4b}$ have an anti-stereorelationship in the compounds of formulas Ia to Ij defined herein.

Preferably, $R^{1b}$ and $R^{2b}$ are each independently selected from hydrogen, hydroxyl, —$NR^{10}R^{11}$, halogen, $C_{1-6}$alkyl, and $C_{1-6}$alkoxy, preferably $R^{1b}$ and $R^{2b}$ are both hydrogen, hydroxyl, halogen or methoxy, or a combination of hydroxyl and methoxy in the compounds of formulas Ia to Ij defined herein.

In further preferred embodiments of the compounds of formulas Ia to Ij defined herein, $R^{3b}$ is selected from hydrogen, hydroxyl, —$NR^{10}R^{11}$, halogen, $C_{1-6}$alkyl, and $C_{1-6}$alkoxy; preferably $R^{3b}$ is hydroxyl, halogen, or methoxy.

In further preferred embodiments of the compounds of formulas Ia to Ij defined herein, $R^{4b}$ is selected from the group consisting of hydrogen, hydroxyl, —$NR^{10}R^{11}$, halogen, $C_{1-6}$alkyl, and $C_{1-6}$alkoxy; preferably $R^{4b}$ is hydroxyl, halogen, or methoxy.

Further preferred embodiments of the invention are compounds having one of the following structural formulas:

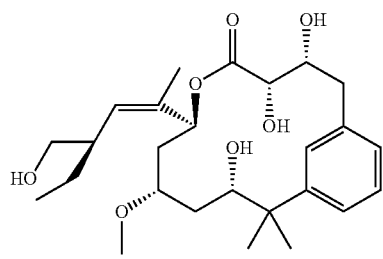

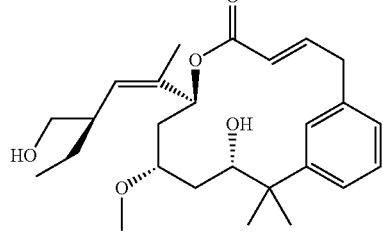

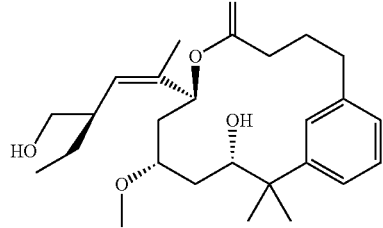

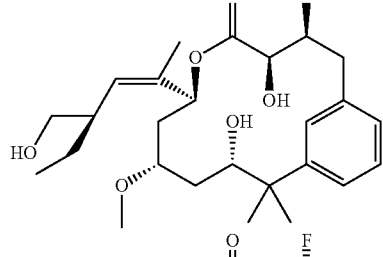

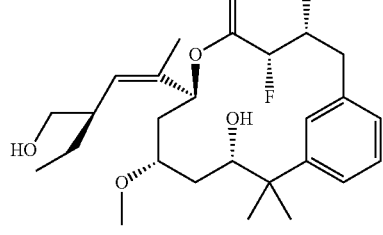

-continued

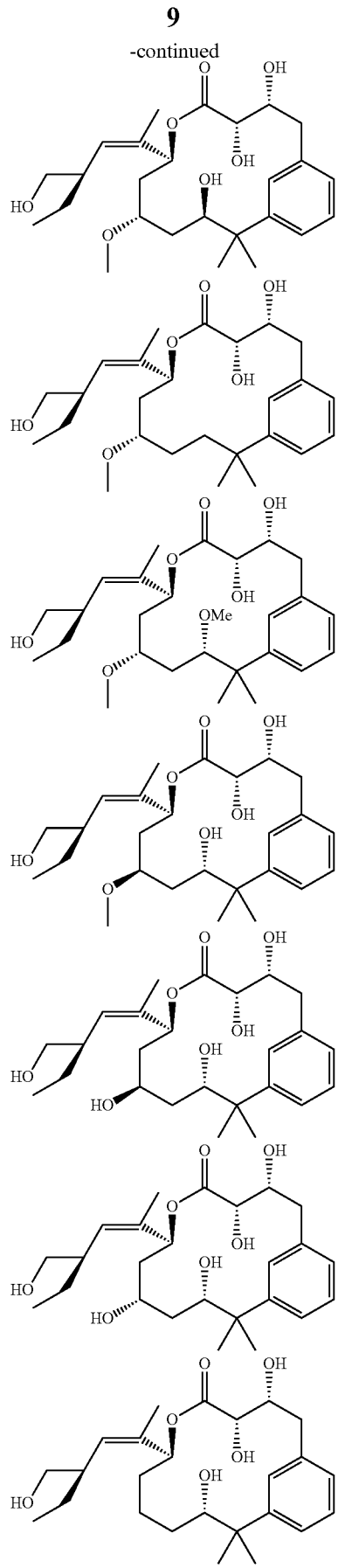

-continued

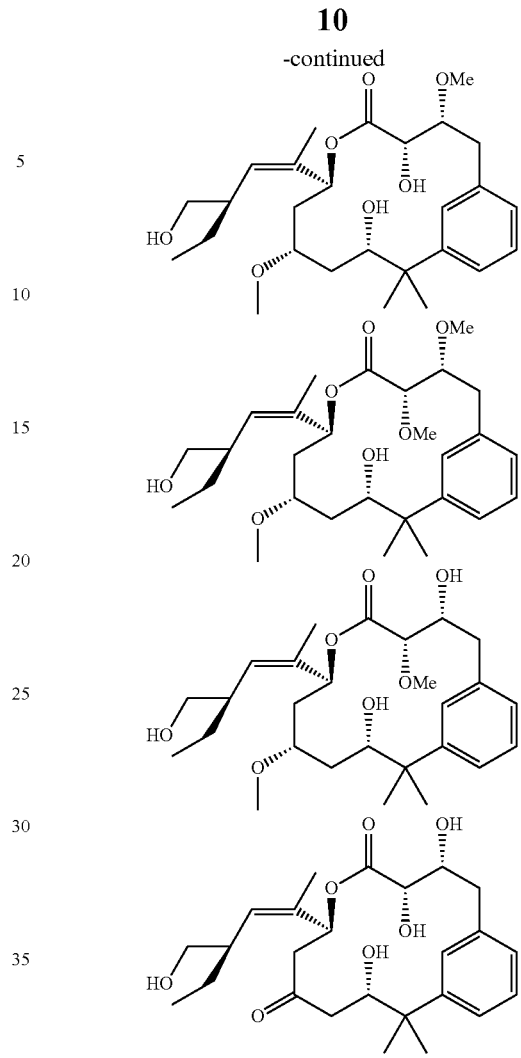

The invention further provides a pharmaceutical composition comprising a compound according to any one of the embodiments defined herein and a pharmaceutically acceptable excipient. In another embodiment, said pharmaceutical composition can comprise a further active pharmaceutical ingredient.

The invention further provides a compound according to any one of the embodiments defined herein, or the pharmaceutical composition as defined herein, for use as a medicament.

Preferably, for treating a disease by intervening at the level of microtubule dynamics, more specifically by stabilizing the microtubules, more preferably for treating a proliferative disorder. In a further preferred embodiment, said proliferative disorder is selected from the group comprising: neoplasia, dysplasia, tumor growth, or cancer. Preferred types of cancer are (advanced) breast cancer, prostate cancer, ovarian cancer, colorectal cancer, lung cancer, melanoma, or epidermoid carcinoma, non-small cell lung cancer and Kaposi's sarcoma.

The invention further provides the use of the compounds or the pharmaceutical composition as defined herein for the manufacturing of a medicament for treating a disease caused by changes in microtubule stability, more preferably for treating a proliferative disorder. In a further preferred embodiment, said proliferative disorder is selected from the group comprising: neoplasia, dysplasia, tumor growth, or cancer. Preferred types of cancer are (advanced) breast cancer, prostate cancer, ovarian cancer, colorectal cancer, lung cancer, melanoma, or epidermoid carcinoma, non-small cell lung cancer and Kaposi's sarcoma.

The invention further provides a method of treating diseases as defined herein, in a subject needing such therapy, comprising administering a therapeutically effective amount of one or more of the compound(s) or the pharmaceutical preparation defined herein to a patient in need thereof. More preferably said disease is a proliferative disorder. In a further preferred embodiment, said proliferative disorder is selected from the group comprising: neoplasia, dysplasia, tumor growth, or cancer. Preferred types of cancer are (advanced) breast cancer, prostate cancer, ovarian cancer, colorectal cancer, lung cancer, melanoma, or epidermoid carcinoma, non-small cell lung cancer and Kaposi's sarcoma. Optionally, said treatment of a proliferative disorder is performed in combination with any one of the therapies selected from the group comprising: surgery, chemotherapy, radiation therapy, immunotherapy, and/or gene therapy.

In certain embodiments of treatment, the compound or the pharmaceutical preparation as defined herein can be administered in combination with one or more additional active compounds, before, after or simultaneously with the administration of said compound or pharmaceutical composition.

In a preferred embodiment, the pharmaceutical composition as defined herein can be administered orally, for example in the form of pills, tablets, lacquered tablets, sugar-coated tablets, granules, hard and soft gelatin capsules, aqueous, alcoholic or oily solutions, syrups, emulsions or suspensions; rectally, for example in the form of suppositories; parenterally, for example subcutaneously, intramuscularly or intravenously in the form of solutions for injection or infusion; percutaneous or topically, for example in the form of ointments, tinctures, sprays or transdermal therapeutic systems; through inhalative administration in the form of e.g. nasal sprays or aerosol mixtures; or in the form of microcapsules, implants or rods.

In a preferred embodiment, the pharmaceutically acceptable carrier and/or additives can be selected from the group of: fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

In a preferred embodiment, the subject is a mammal, e.g. human, equine, rabbit, mouse, rat, pig, sheep, cow or dog. Preferably the subject is human.

Taking into account the small size of the peloruside analog, we do not foresee pharmacodynamic problems in the systemic treatment of cancer. For "topical" treatment of ovarian cancer via the peritoneal cavity the small size may facilitate diffusion into the circulation, which reduces the local retention of the drug at the site of tumor deposits in the peritoneum.

The invention further provides for a process for producing a compound according to the general formula I, comprising the steps of:
(a) reacting a methyl ketone having structural Formula IIa with an aldehyde having structural Formula IIb, through aldol coupling, wherein $P^4$ and $P^5$ are protecting groups, and executing suitable functional group interconversions, thereby obtaining a compound having structural Formula II;
(b) protecting the functional groups at positions $X^3$ and $X^4$ in the compound of Formula II where needed;
(c) reacting the compound of Formula II with a compound of the Formula III in the presence of a suitable catalyst, giving rise to a compound of the formula (IV),
(d) removing the protecting groups $P^1$ and $P^4$ in the resulting compound and esterifying the deprotected COOH with the $C_{15}$ OH group, thereby obtaining the lactone having structural Formula V; and
(e) deprotecting $P^5$ in the compound having structural Formula V and deprotecting any of the possibly protected $X^1$, $X^2$, $X^3$, or $X^4$ groups, if required after executing additional suitable functional group interconversions, thereby obtaining a compound having structural Formula I, generally following the reaction scheme below:

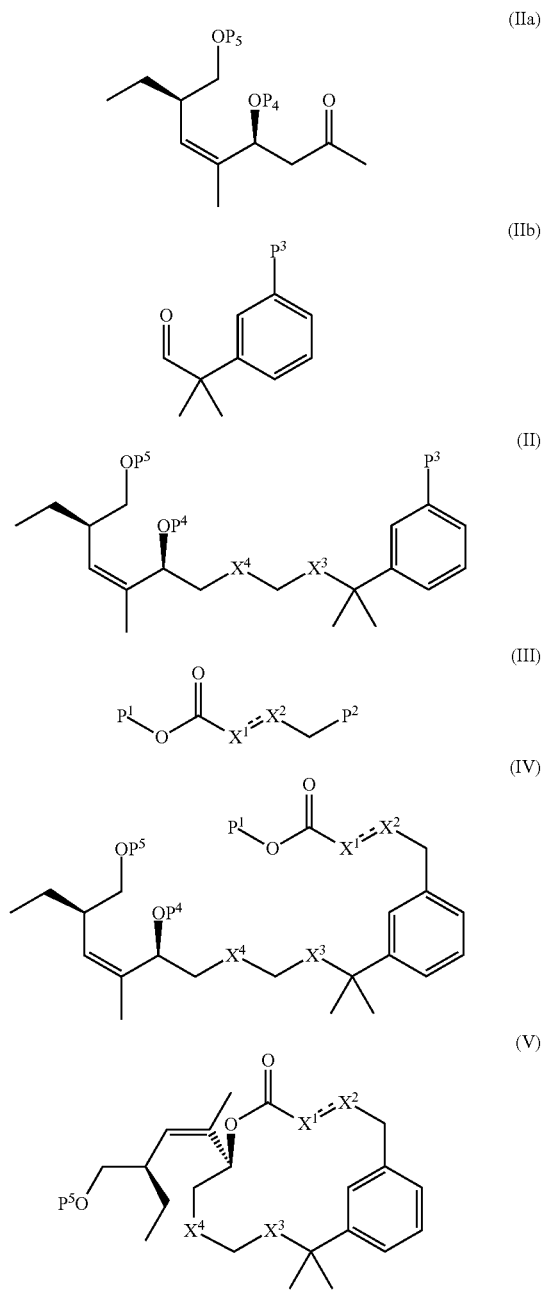

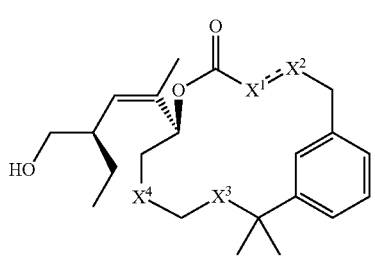

(I)

wherein
- P¹ is hydrogen or a carboxyl protecting group; for example optionally substituted alkyl, preferably P¹ is methyl;
- P² is selected from halogen, pseudohalogen, $CF_3SO_3$, OAc, preferably P² is bromo, and simultaneously,
- P³ is a trialkyltin, such as trimethyltin or tri-n-butyltin, or is a boronic acid or boronic ester; or alternatively,
- P² is a trialkyltin, such as trimethyltin or tri-n-butyltin, or is a boronic acid or boronic ester and simultaneously,
- P³ is selected from halogen, pseudohalogen, $CF_3SO_3$, OAc, (for example, P³ is bromo);
- P⁴ is selected from an orthogonally chosen protecting group, preferably P⁴ is MPM (4-OMe-Bn);
- P⁵ is a protecting group which can be orthogonally removed, preferably selected from: TBS (tert-butyldimethylsilyl) or MEM (2-methoxyethoxymethyl);
- the suitable catalyst is typically a transition metal with ligands. For example, said suitable catalyst can be $Pd_2(dba)_3 \cdot CHCl_3$; and
- $X^1, X^2, X^3$, and $X^4$ have the same meaning as that defined above, and wherein, if present, their functional groups are suitably protected in steps (b) and (c), functionally interconverted where needed and deprotected accordingly in step (d).

BRIEF DESCRIPTION OF THE FIGURES

The present invention is illustrated by the following figures which are to be considered for illustrative purposes only and in no way limit the invention to the embodiments disclosed therein.

DETAILED DESCRIPTION OF THE INVENTION

Figure 1:
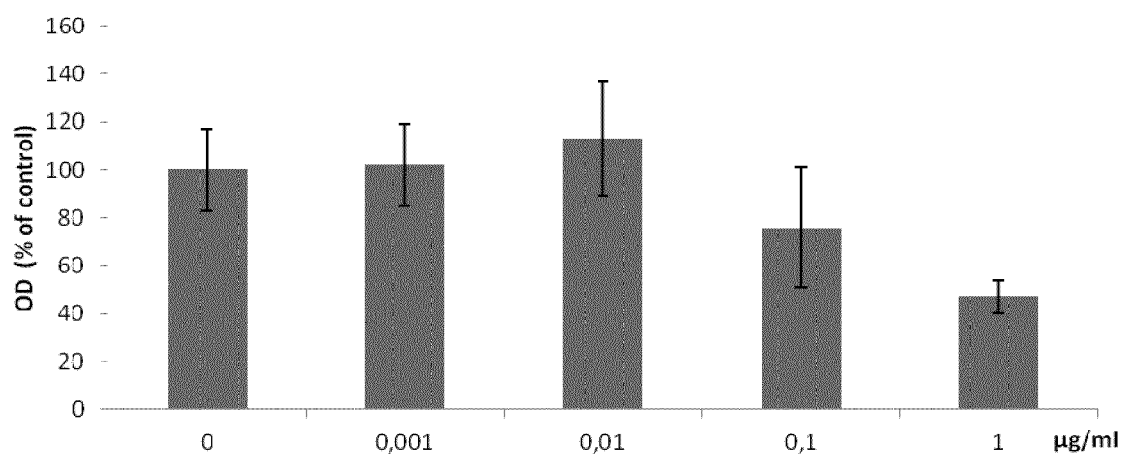
FIG. 1: JC168 inhibits cell growth. MO4 cells were treated with dimethyl sulfoxide (DMSO, solvent control), 0.001, 0.01, 0.1 or 1 μg/ml JC168 for 4 days. After said 4 days of incubation the cells were fixed and stained with sulforhodamine B to determine cellular protein content. Excess dye was removed by washing. Protein-bound dye was dissolved and optical density was measured. Data represent optical density (OD) as a percentage of solvent control (mean and standard deviation, n=6).

As used herein, the singular forms "a", "an", and "the" include both singular and plural referents unless the context clearly dictates otherwise. By way of example, "a compound" can refer to one or more than one compound; "a composition" refers to one or more than one composition.

The terms "comprising", "comprises" and "comprised of" as used herein are synonymous with "including", "includes" or "containing", "contains", and are inclusive or open-ended and do not exclude additional, non-recited members, elements or method steps. The term "comprising" also encompasses the closed-wording "consisting of" and "consisting essentially of".

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

The expression "the corresponding $R^{xa}$" or "the corresponding $R^{xb}$ group" needs to be seen in the light of formula "$CR^{xa}R^{xb}$" (e.g. $CR^{1a}R^{1b}$, $CR^{2a}R^{2b}$, $CR^{3a}R^{3b}$, and $CR^{4a}R^{4b}$). For each $R^{xa}$ group, there is a corresponding $R^{xb}$ group in the substituent $R^{xa}R^{xb}$ and vice versa. As an example, for each $R^{1a}$ group, there is a corresponding $R^{1b}$ group in the $R^{1a}R^{1b}$ substituent, and vice versa.

All documents cited in the present specification are hereby incorporated by reference in their entirety. In particular, the teachings of all documents herein specifically referred to are incorporated by reference.

The inventors have designed so-called "phenyl-pelorusides", or "pelofens", which are peloruside analogs, wherein the pyranose group has been substituted by a phenyl group. The first compound synthesised was designated "JC168" and had the following structural formula:

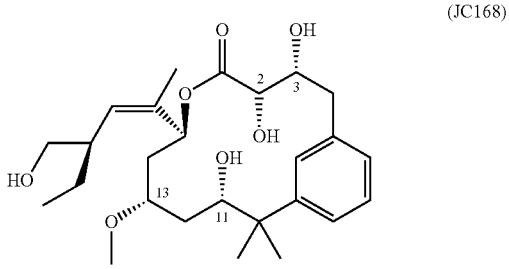

(JC168)

Because of the biological activity of JC168, a whole array of phenyl analogs can be synthesized to further explore the structure-activity relationship (SAR) of the peloruside binding site. Because these phenyl analogs are structurally less complicated and thus more easily accessible than peloruside, the SAR of peloruside can be studied via these analogs. The inventors therefore embarked on a strategy to design analogs of said general pelofen compound, especially focussing on modifying the substituents at positions $C_2$, $C_3$, $C_{11}$, and $C_{13}$. Said positions are called respectively $X^1$, $X^2$, $X^3$ and $X^4$ in general formula I.

The term "compounds as defined herein" therefore comprises all compounds having the general Formula I:

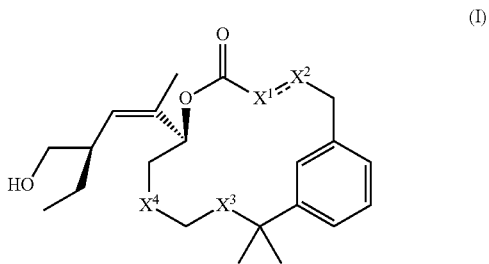

(I)

wherein
$X^1$ is $CR^{1a}R^{1b}$, $X^2$ is $CR^{2a}R^{2b}$, $X^3$ is $CR^{3a}R^{3b}$, $X^4$ is $CR^{4a}R^{4b}$, wherein
$R^{1a}$, $R^{2a}$, $R^{3a}$, and $R^{4a}$ are each independently selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; and
$R^{1b}$, $R^{2b}$, $R^{3b}$, and $R^{4b}$ each independently are selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; or $R^{1a}$ and $R^{1b}$, or $R^{2a}$ and $R^{2b}$, or $R^{3a}$ and $R^{3b}$, or $R^{4a}$ and $R^{4b}$ taken together represent an oxo (=O) group;
wherein the bond represented by a dashed and solid line represents a single bond or a double bond and in case of a double bond, $R^{1b}$ and $R^{2b}$ are absent and at least one of $R^{1a}$ and $R^{2a}$ is not OH or $-NR^{10}R^{11}$; and
$R^{10}$ and $R^{11}$ are each independently selected from hydrogen and $C_{1-6}$alkyl; and wherein:
when $R^{1a}$, $R^{2a}$, $R^{3a}$ or $R^{4a}$ is hydroxyl, the corresponding $R^{1b}$, $R^{2b}$, $R^{3b}$ or $R^{4b}$ is not hydroxyl, is not $-NR^{10}R^{11}$, is not halogen, or is not $C_{1-6}$alkoxy,
when $R^{1a}$, $R^{2a}$, $R^{3a}$ or $R^{4a}$ is $-NR^{10}R^{11}$, the corresponding $R^{1b}$, $R^{2b}$, $R^{3b}$ or $R^{4b}$ is not hydroxyl, is not $-NR^{10}R^{11}$, is not halogen, or is not $C_{1-6}$alkoxy,
when $R^{1a}$, $R^{2a}$, $R^{3a}$ or $R^{4a}$ is halogen, the corresponding $R^{1b}$, $R^{2b}$, $R^{3b}$ or $R^{4b}$ is not hydroxyl, or is not $-NR^{10}R^{11}$,
when $R^{1b}$, $R^{2b}$, $R^{3b}$ or $R^{4b}$ is hydroxyl, the corresponding $R^{1a}$, $R^{2a}$, $R^{3a}$ or $R^{4a}$ is not hydroxyl, is not $-NR^{10}R^{11}$, is not halogen, or is not $C_{1-6}$alkoxy, and
when $R^{1b}$, $R^{2b}$, $R^{3b}$ or $R^{4b}$ is $-NR^{10}R^{11}$, the corresponding $R^{1a}$, $R^{2a}$, $R^{3a}$ or $R^{4a}$ is not hydroxyl, is not $-NR^{10}R^{11}$, is not halogen, or is not $C_{1-6}$alkoxy.
when $R^{1b}$, $R^{2b}$, $R^{3b}$ or $R^{4b}$ is halogen, the corresponding $R^{1a}$, $R^{2a}$, $R^{3a}$ or $R^{4a}$ is not hydroxyl, or is not $-NR^{10}R^{11}$, Also the stereoisomers, prodrugs, tautomers, racemates, salts, hydrates, or solvates of said compounds are falling within the definition of the term "compounds as defined herein".

In a preferred subset of compounds as defined herein, the $C_2$-$C_3$ substituents are envisaged, meaning the structural formula I is only changed at said two positions. Positions $C_{11}$ and $C_{13}$ are as in the original pelofen JC168, as depicted in formula (XI) below:

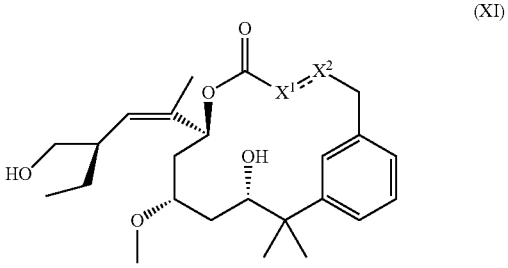

(XI)

wherein
$X^1$ is $CR^{1a}R^{1b}$, $X^2$ is $CR^{2a}R^{2b}$, wherein
$R^{1a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl, and $C_{1-6}$alkoxy;
$R^{2a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy;
$R^{1b}$ is selected from hydrogen, hydroxyl, halogen and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy;

$R^{2b}$ is selected from hydrogen, hydroxyl, halogen and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; or wherein $R^{1a}$ and $R^{1b}$, or $R^{2a}$ and $R^{2b}$, taken together represent an oxo (=O) group;

wherein the bond represented by a dashed and solid line represents a single bond or a double bond and in case of a double bond, $R^{1b}$ and $R^{2b}$ are absent and at least one of $R^{1a}$ and $R^{2a}$ is not OH or —$NR^{10}R^{11}$; wherein $R^{10}$ and $R^{11}$ are each independently selected from hydrogen and $C_{1-6}$alkyl; and wherein when $R^{1a}$ or $R^{2a}$ is hydroxyl, the corresponding $R^{1b}$ or $R^{2b}$ is not hydroxyl, is not —$NR^{10}R^{11}$, is not halogen, or is not $C_{1-6}$alkoxy, when $R^{1a}$ or $R^{2a}$ is —$NR^{10}R^{11}$, the corresponding $R^{1b}$ or $R^{2b}$ is not hydroxyl, is not —$NR^{10}R^{11}$, is not halogen, or is not $C_{1-6}$alkoxy, when $R^{1a}$ or $R^{2a}$ is halogen, the corresponding $R^{1b}$ or $R^{2b}$ is not hydroxyl, or is not —$NR^{10}R^{11}$, when $R^{1b}$ or $R^{2b}$ is hydroxyl, the corresponding $R^{1a}$ or $R^{2a}$ is not hydroxyl, is not —$NR^{10}R^{11}$, is not halogen, or is not $C_{1-6}$alkoxy, and when $R^{1b}$ or $R^{2b}$ is —$NR^{10}R^{11}$, the corresponding $R^{1a}$ or $R^{2a}$ is not hydroxyl, is not —$NR^{10}R^{11}$, is not halogen, or is not $C_{1-6}$alkoxy.

when $R^{1b}$ or $R^{2b}$ is halogen, the corresponding $R^{1a}$ or $R^{2a}$ is not hydroxyl, or is not —$NR^{10}R^{11}$.

In preferred embodiments, the invention provides compounds of Formula XIa:

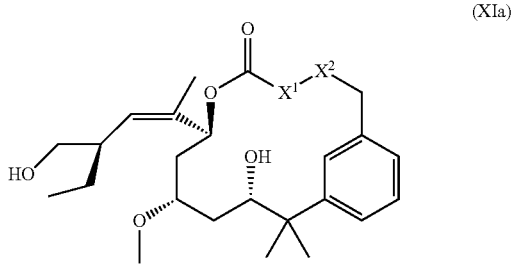

wherein:
$X^1$ is $CR^{1a}R^{1b}$, and $X^2$ is $CR^{2a}R^{2b}$, wherein
$R^{1a}$ and $R^{2a}$ are both hydrogen;
$R^{1b}$ and $R^{2b}$ are each independently selected from hydrogen, hydroxyl, —$NR^{10}R^{11}$, halogen, $C_{1-6}$alkyl, and $C_{1-6}$alkoxy; preferably wherein $R^{1b}$ and $R^{2b}$ are both hydrogen, hydroxyl, halogen or methoxy, or a combination of hydroxyl and methoxy; preferably, wherein $R^{1b}$ and $R^{2b}$ are halogen; preferably, wherein $R^{1b}$ is hydroxyl and $R^{2b}$ is methoxy or vice versa; preferably, wherein $R^{1b}$ is halogen and $R^{2b}$ is methoxy, or vice versa; preferably, wherein $R^{1b}$ is halogen and $R^{2b}$ is hydroxyl, or vice versa; preferably, wherein $R^{1b}$ and $R^{2b}$ are methoxy; preferably, wherein $R^{1b}$ and $R^{2b}$ are hydroxyl.

In further preferred embodiments, the invention provides compounds of Formula XIb:

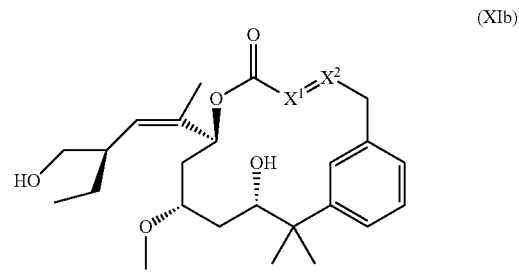

wherein:
$X^1$ is $CR^{1a}R^{1b}$, and $X^2$ is $CR^{2a}R^{2b}$, wherein
the bond between $X^1$ and $X^2$ is a double bond, and $R^{1a}$ and $R^{2a}$ hence are absent;
$R^{1b}$ and $R^{2b}$ are each independently selected from hydrogen, hydroxyl, —$NR^{10}R^{11}$, halogen, $C_{1-6}$alkyl, and $C_{1-6}$alkoxy; preferably wherein $R^{1b}$ and $R^{2b}$ are both hydrogen, hydroxyl, halogen or methoxy, or a combination of hydroxyl and methoxy; preferably, wherein $R^{1b}$ and $R^{2b}$ are halogen; preferably, wherein $R^{1b}$ is hydroxyl and $R^{2b}$ is methoxy or vice versa; preferably, wherein $R^{1b}$ is halogen and $R^{2b}$ is methoxy, or vice versa; preferably, wherein $R^{1b}$ is halogen and $R^{2b}$ is hydroxyl, or vice versa; preferably, wherein $R^{1b}$ and $R^{2b}$ are methoxy; preferably, wherein $R^{1b}$ and $R^{2b}$ are hydroxyl.

In another preferred subset of compounds as defined herein, the $C_{13}$ substituents are envisaged, meaning the structural formula I is only changed at said position. Positions $C_2$, $C_3$, and $C_{11}$ are as in the original pelofen JC168, as depicted in formula (XII) below:

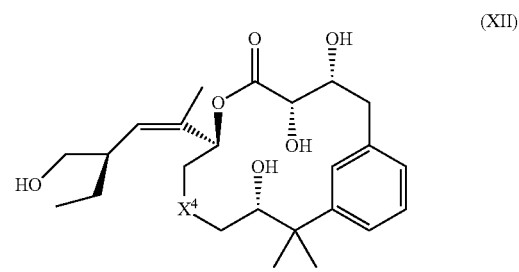

wherein
$X^4$ is $CR^{4a}R^{4b}$, wherein
$R^{4a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; and
$R^{4b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; or wherein $R^{4a}$ and $R^{4b}$ taken together represent an oxo (=O) group; and wherein $R^{10}$ and $R^{11}$ are each independently selected from hydrogen and $C_{1-6}$alkyl, and when $R^{4a}$ is hydroxyl, $R^{4b}$ is not hydroxyl, is not —$NR^{10}R^{11}$, is not halogen, or is not $C_{1-6}$alkoxy, when $R^{4a}$ is —$NR^{10}R^{11}$, $R^{4b}$ is not hydroxyl, is not —$NR^{10}R^{11}$, is not halogen, or is not $C_{1-6}$alkoxy, when $R^{4a}$ is halogen, $R^{4b}$ is not hydroxyl, or is not —$NR^{10}R^{11}$, when $R^{4b}$ is hydroxyl, $R^{4a}$ is not hydroxyl, is not —$NR^{10}R^{11}$, is not halogen, or is not $C_{1-6}$alkoxy, and when $R^{4b}$ is —$NR^{10}R^{11}$, $R^{4a}$ is not hydroxyl, is not —$NR^{10}R^{11}$, is not halogen, or is not $C_{1-6}$alkoxy.

when $R^{4b}$ is halogen, $R^{4a}$ is not hydroxyl, or is not —$NR^{10}R^{11}$.

In preferred embodiments of the compounds of Formula XII, $R^{4a}$ is hydrogen and $R^{4b}$ is selected from the group consisting of: hydrogen, hydroxyl, halogen, or from a group selected from —$NR^{10}R^{11}$, $C_{1-6}$alkyl, and $C_{1-6}$alkoxy, each independently optionally substituted with one or more substituent(s) each independently selected from hydroxyl, halogen, $C_{1-6}$alkyl and $C_{1-6}$alkoxy. Preferably $R^{4b}$ is hydroxyl, halogen, or methoxy.

In further preferred embodiments of the compounds of Formula XII, $R^{4a}$ and $R^{4b}$ taken together represent an oxo (=O) group.

In another preferred subset of compounds as defined herein, the $C_{11}$ substituents are envisaged, meaning the structural formula I is only changed at said position. Positions $C_2$, $C_3$, and $C_{13}$ are as in the original pelofen JC168, as depicted in formula (XIII) below:

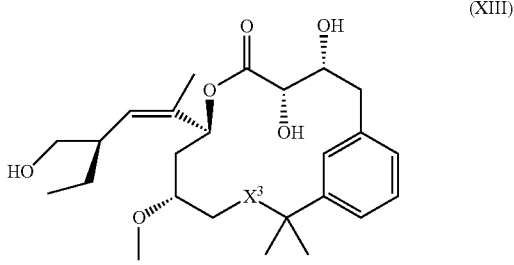

(XIII)

wherein $X^3$ is $CR^{3a}R^{3b}$, wherein $R^{3a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; and $R^{3b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; or $R^{3a}$ and $R^{3b}$ taken together represent an oxo (=O) group;

$R^{10}$ and $R^{11}$ are each independently selected from hydrogen and $C_{1-6}$alkyl, and when $R^{3a}$ is hydroxyl, $R^{3b}$ is not hydroxyl, is not —$NR^{10}R^{11}$, is not halogen, or is not $C_{1-6}$alkoxy, when $R^{3a}$ is —$NR^{10}R^{11}$, $R^{3b}$ is not hydroxyl, is not —$NR^{10}R^{11}$, is not halogen, or is not $C_{1-6}$alkoxy, when $R^{3a}$ is halogen, $R^{3b}$ is not hydroxyl, or is not —$NR^{10}R^{11}$, when $R^{3b}$ is hydroxyl, $R^{3a}$ is not hydroxyl, is not —$NR^{10}R^{11}$, is not halogen, or is not $C_{1-6}$alkoxy, and when $R^{3b}$ is —$NR^{10}R^{11}$, $R^{3a}$ is not hydroxyl, is not —$NR^{10}R^{11}$, is not halogen, or is not $C_{1-6}$alkoxy.

when $R^{3b}$ is halogen, $R^{3a}$ is not hydroxyl, or is not —$NR^{10}R^{11}$

In further preferred embodiments of the compounds defined by Formula (XIII), $R^{3a}$ is hydrogen and $R^{3b}$ is selected from the group consisting of: hydrogen, hydroxyl, halogen, or from a group selected from: —$NR^{10}R^{11}$, $C_{1-6}$alkyl, and $C_{1-6}$alkoxy, each independently optionally substituted with one or more substituent(s) each independently selected from hydroxyl, halogen, $C_{1-6}$alkyl and $C_{1-6}$alkoxy. Preferably $R^{3b}$ is hydroxyl, halogen, or methoxy.

In further preferred embodiments of the compounds defined by Formula XIII, $R^{3a}$ and $R^{3b}$ taken together represent an oxo (=O) group.

In yet another subset of compounds, as defined herein, both the $C_{11}$ and $C_{13}$ substituents are envisaged, meaning the structural formula I is changed at positions $C_{11}$ and $C_{13}$. Positions $C_2$, and $C_3$, are as in the original pelofen JC168, as depicted in formula (XIV) below:

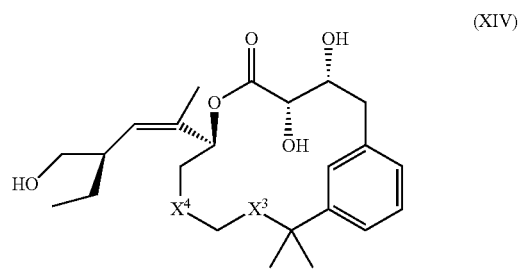

(XIV)

wherein $X^3$ is $CR^{3a}R^{3b}$, $X^4$ is $CR^{4a}R^{4b}$, wherein $R^{3a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy;

$R^{4a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; and $R^{3b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy;

$R^{4b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy; or wherein $R^{3a}$ and $R^{3b}$, or $R^{4a}$ and $R^{4b}$ taken together represent an oxo (=O) group; and wherein $R^{10}$ and $R^{11}$ are each independently selected from hydrogen and $C_{1-6}$alkyl, and when $R^{3a}$ or $R^{4a}$ is hydroxyl, the corresponding $R^{3b}$ or $R^{4b}$ is not hydroxyl, is not —$NR^{10}R^{11}$, is not halogen, or is not $C_{1-6}$alkoxy, when $R^{3a}$ or $R^{4a}$ is —$NR^{10}R^{11}$, the corresponding $R^{3b}$ or $R^{4b}$ is not hydroxyl, is not —$NR^{10}R^{11}$, is not halogen, or is not $C_{1-6}$alkoxy, when $R^{3a}$ or $R^{4a}$ is halogen, the corresponding $R^{3b}$ or $R^{4b}$ is not hydroxyl, or is not —$NR^{10}R^{11}$, when $R^{3b}$ or $R^{4b}$ is hydroxyl, the corresponding $R^{3a}$ or $R^{4a}$ is not hydroxyl, is not —$NR^{10}R^{11}$, is not halogen, or is not $C_{1-6}$alkoxy, and when $R^{3b}$ or $R^{4b}$ is —$NR^{10}R^{11}$, the corresponding $R^{3a}$ or $R^{4a}$ is not hydroxyl, is not —$NR^{10}R^{11}$, is not halogen, or is not $C_{1-6}$alkoxy.

when $R^{3b}$ or $R^{4b}$ is halogen, the corresponding $R^{3a}$ or $R^{4a}$ is not hydroxyl, or is not —$NR^{10}R^{11}$ In further preferred embodiments of the compounds defined by Formula (XIV), $R^{3a}$ and $R^{4a}$ are both hydrogen, $R^{3b}$ is selected from the group consisting of: hydrogen, hydroxyl, halogen, or from a group selected from: —$NR^{10}R^{11}$, $C_{1-6}$alkyl, and $C_{1-6}$alkoxy, each independently optionally substituted with one or more substituent(s) each independently selected from hydroxyl, halogen, $C_{1-6}$alkyl and $C_{1-6}$alkoxy, and/or $R^{4b}$ is selected from the group consisting of: hydrogen, hydroxyl, halogen, or from a group selected from —$NR^{10}R^{11}$, $C_{1-6}$alkyl, and $C_{1-6}$alkoxy, each independently optionally substituted with one or more substituent(s) each independently selected from hydroxyl, halogen, $C_{1-6}$alkyl and $C_{1-6}$alkoxy. Preferably $R^{3b}$ is hydroxyl and $R^{4b}$ is methoxy or vice versa. Preferably, $R^{3b}$ is hydroxyl and $R^{4b}$ is halogen or vice versa. Preferably, $R^{3b}$ is halogen and $R^{4b}$ is methoxy or vice versa. Preferably, both $R^{3b}$ and $R^{4b}$ are hydroxyl, both $R^{3b}$ and $R^{4b}$ are halogen, or both $R^{3b}$ and $R^{4b}$ are methoxy.

In yet another subset of compounds, as defined herein, all four $C_2$, $C_3$, $C_{11}$ and $C_{13}$ substituents are envisaged, meaning the structural formula I is changed at positions $C_2$, $C_3$, $C_{11}$ and $C_{13}$:

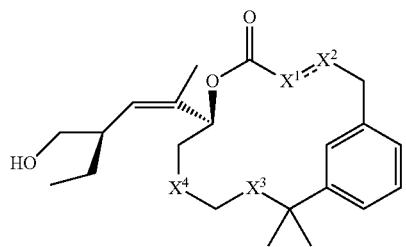

(I)

wherein $X^1$ is $CR^{1a}R^{1b}$, $X^2$ is $CR^{2a}R^{2b}$, $X^3$ is $CR^{3a}R^{3b}$, $X^4$ is $CR^{4a}R^{4b}$, and wherein:

$R^{1a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy;

$R^{2a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{3a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy $R^{4a}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy; and wherein:

$R^{1b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{2b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{3b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{4b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being independently optionally substituted with one or more substituent(s) each independently selected from hydroxyl, halogen, $C_{1-6}$alkyl and $C_{1-6}$alkoxy;

or wherein $R^{1a}$ and $R^{1b}$, or $R^{2a}$ and $R^{2b}$, or $R^{3a}$ and $R^{3b}$, or $R^{4a}$ and $R^{4b}$ taken together represent an oxo (=O) group; and wherein the bond represented by a dashed and solid line represents a single bond or a double bond and wherein in case of a double bond, $R^{1b}$ and $R^{2b}$ are absent and at least one of $R^{1a}$ and $R^{2a}$ is not OH or —$NR^{10}R^{11}$; and wherein:

$R^{10}$ and $R^{11}$ are each independently selected from hydrogen and $C_{1-6}$alkyl; and wherein:

when $R^{1a}$, $R^{2a}$, $R^{3a}$ or $R^{4a}$ is hydroxyl, the corresponding $R^{1b}$, $R^{2b}$, $R^{3b}$ or $R^{4b}$ is not hydroxyl, is not —$NR^{10}R^{11}$, is not halogen, or is not $C_{1-6}$alkoxy, when $R^{1a}$, $R^{2a}$, $R^{3a}$ or $R^{4a}$ is —$NR^{10}R^{11}$, the corresponding $R^{1b}$, $R^{2b}$, $R^{3b}$ or $R^{4b}$ is not hydroxyl, is not —$NR^{10}R^{11}$, is not halogen, or is not $C_{1-6}$alkoxy, when $R^{1a}$, $R^{2a}$, $R^{3a}$ or $R^{4a}$ is halogen, the corresponding $R^{1b}$, $R^{2b}$, $R^{3b}$ or $R^{4b}$ is not hydroxyl, or is not —$NR^{10}R^{11}$, when $R^{1b}$, $R^{2b}$, $R^{3b}$ or $R^{4b}$ is hydroxyl, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy, and when $R^{1b}$, $R^{2b}$, $R^{3b}$ or $R^{4b}$ is —$NR^{10}R^{11}$, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy.

when $R^{1b}$, $R^{2b}$, $R^{3b}$ or $R^{4b}$ is halogen, the corresponding $R^{1a}$, $R^{2a}$, $R^{3a}$ or $R^{4a}$ is not hydroxyl, or is not —$NR^{10}R^{11}$.

In a preferred embodiment, the invention provides compounds having structural Formula Ia, and the stereoisomers, prodrugs, tautomers, racemates, salts, hydrates, or solvates thereof:

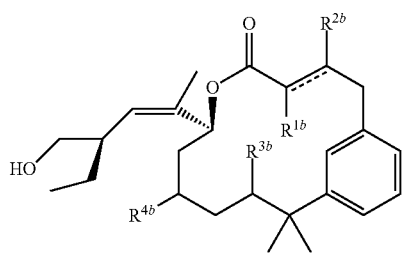

(Ia)

wherein $R^{1b}$, $R^{2b}$, $R^{3b}$, and $R^{4b}$ have the same meaning as defined above.

In another preferred embodiment, the invention provides compounds having structural Formula Ib, Ic or Id, and the stereoisomers, prodrugs, tautomers, racemates, salts, hydrates, or solvates thereof:

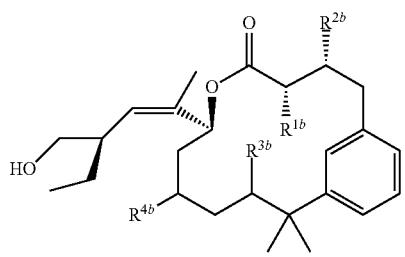

(Ib)

(Ic)

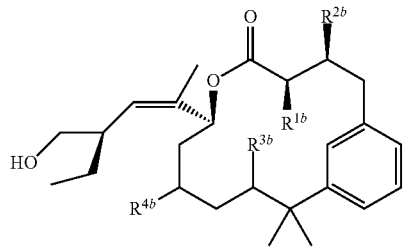

(Id)

wherein $R^{1b}$, $R^{2b}$, $R^{3b}$, and $R^{4b}$ have the same meaning as defined above. The double bond in structure Ic can have the Z- or E-geometry.

In another preferred embodiment, the invention provides compounds having structural Formula Ie, If, or Ig, and the stereoisomers, prodrugs, tautomers, racemates, salts, hydrates, or solvates thereof:

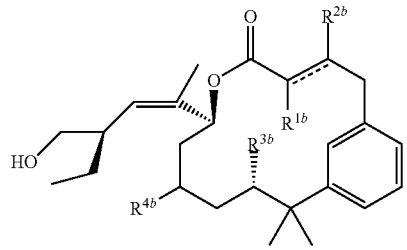

(Ie)

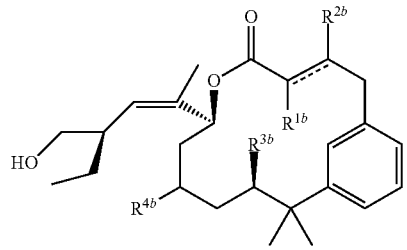

(If)

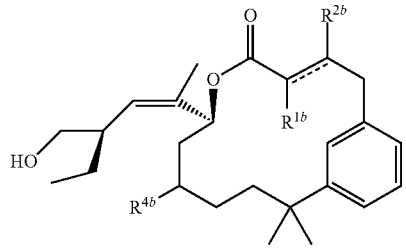

(Ig)

wherein $R^{1b}$, $R^{2b}$, $R^{3b}$, and $R^{4b}$ have the same meaning as defined above. Preferably, the bond represented by a dashed and solid line represents a single bond and $R^{1b}$ and $R^{2b}$ are positioned as in formula Ib or Id. Alternatively the bond represented by a dashed and solid line represents a double bond.

In another embodiment, the invention provides compounds having structural Formula Ih, Ii, or Ij, and the stereoisomers, prodrugs, tautomers, racemates, salts, hydrates, or solvates thereof:

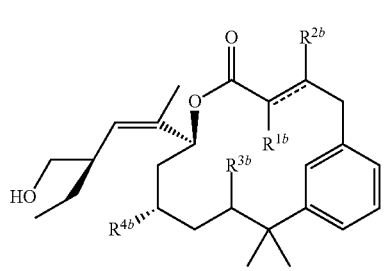

(Ih)

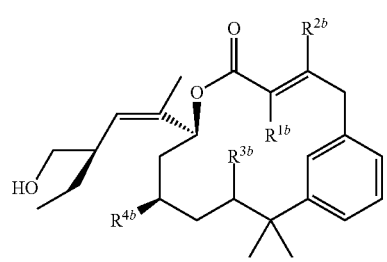

(Ii)

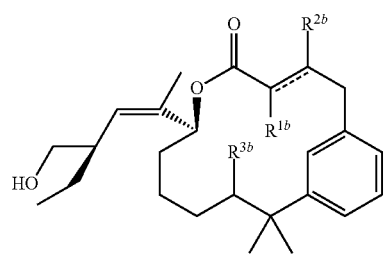

(Ij)

wherein $R^{1b}$, $R^{2b}$, $R^{3b}$, and $R^{4b}$ have the same meaning as defined above. Preferably, the bond represented by a dashed and solid line represents a single bond and $R^{1b}$ and $R^{2b}$ are positioned as in formula Ib or Id. Alternatively the bond represented by a dashed and solid line represents a double bond.

Preferably, $R^{3b}$ and $R^{4b}$ have an anti-stereorelationship in the compounds defined herein.

Preferably, $R^{1b}$ and $R^{2b}$ are each independently selected from hydrogen, hydroxyl, —$NR^{10}R^{11}$, halogen, $C_{1-6}$alkyl, and $C_{1-6}$alkoxy, preferably $R^{1b}$ and $R^{2b}$ are both hydrogen, hydroxyl, halogen or methoxy, or a combination of hydroxyl and methoxy in the compounds defined herein.

In further preferred embodiments of the compounds defined herein, $R^{3b}$ is selected from hydrogen, hydroxyl, —$NR^{10}R^{11}$, halogen, $C_{1-6}$alkyl, and $C_{1-6}$alkoxy; preferably $R^{3b}$ is hydroxyl, halogen, or methoxy.

In further preferred embodiments of the compounds defined herein, $R^{4b}$ is selected from the group consisting of hydrogen, hydroxyl, —$NR^{10}R^{11}$, halogen, $C_{1-6}$alkyl, and $C_{1-6}$alkoxy; preferably $R^{4b}$ is hydroxyl, halogen, or methoxy.

Further preferred embodiments of the invention are compounds having one of the following structural formulas:

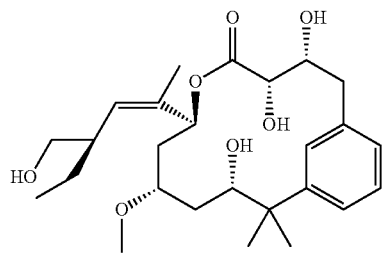

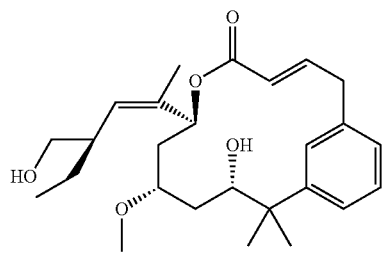

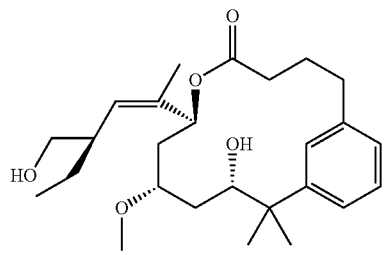

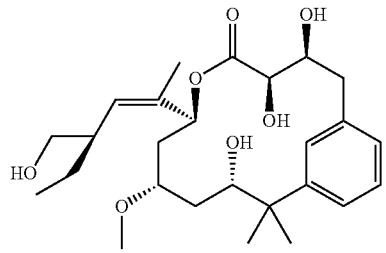

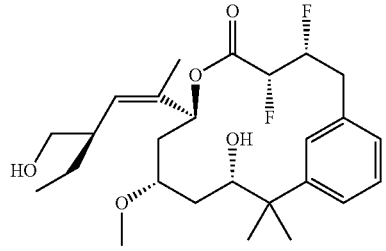

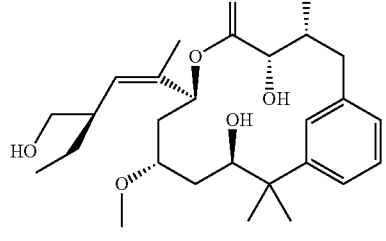

-continued

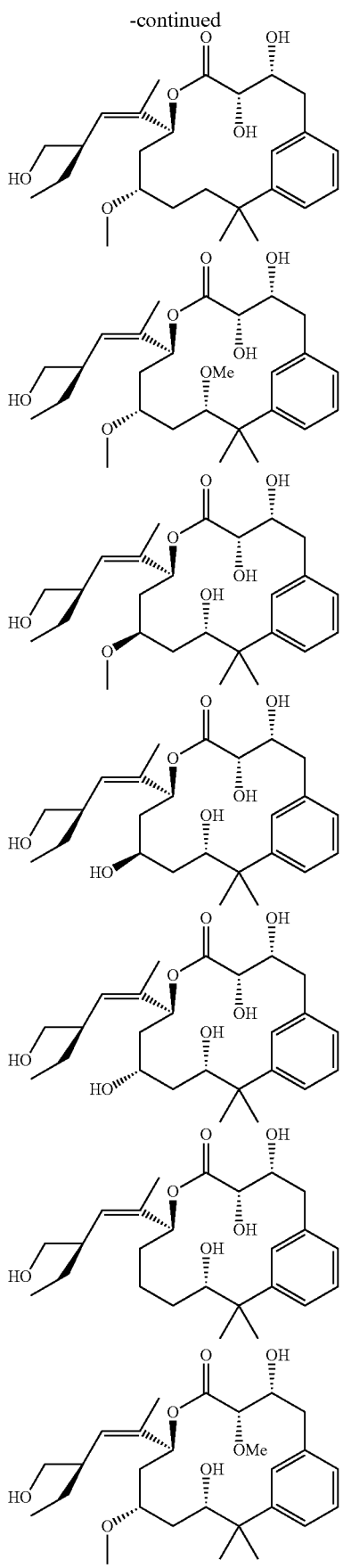

-continued

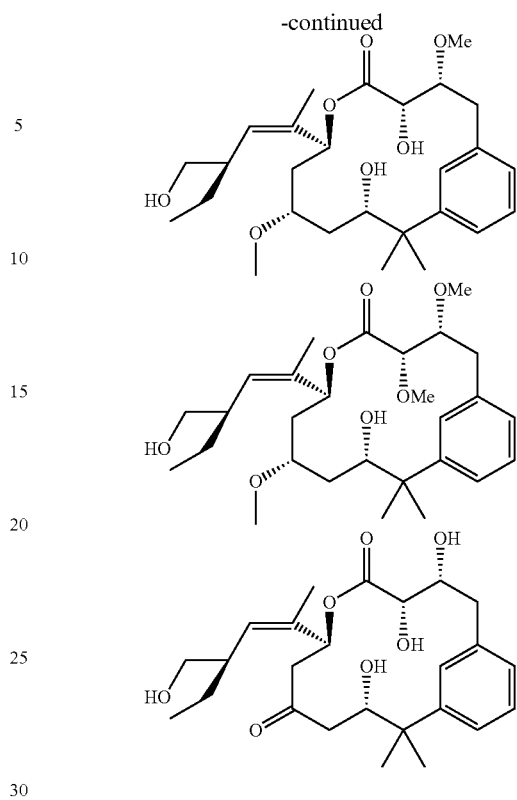

In the compounds defined herein, the term "halo" or "halogen" as a group or part of a group is generic for fluoro, chloro, bromo, or iodo.

In the compounds defined herein, the term "oxo" as used herein refers to the group =O.

In the compounds defined herein, the term "hydroxyl" or "hydroxy" as used herein refers to the group —OH.

The term "alkyl", as a group or part of a group, refers to a hydrocarbyl group of Formula $C_nH_{2n+1}$ wherein n is a number of at least 1. Alkyl groups may be linear, or branched and may be substituted as indicated herein. Generally, the alkyl groups comprise from 1 to 6 carbon atoms, more preferably 1, 2, 3, 4, 5, or 6 carbon atoms. When a subscript is used herein following a carbon atom, the subscript refers to the number of carbon atoms that the named group may contain. For example, the term "$C_{1-6}$alkyl", as a group or part of a group, refers to a hydrocarbyl group of Formula $C_nH_{2n+1}$ wherein n is a number ranging from 1 to 6. Thus, for example, $C_{1-20}$alkyl groups include all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers. For example, $C_{1-6}$ alkyl includes all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers. When the suffix "ene" is used in conjunction with an alkyl group, i.e. "alkylene", this is intended to mean the alkyl group as defined herein having two single bonds as points of attachment to other groups. Non-limiting examples of alkylene groups includes methylene, ethylene, methylmethylene, propylene, ethylethylene, and 1,2-dimethylethylene. Similarly, where alkenyl groups as defined herein and alkynyl groups as defined herein, respectively, are divalent groups having single bonds for attachment to two other groups, they are termed "alkenylene" and "alkynylene" respectively.

In the compounds defined herein, the term "$C_{2-6}$alkenyl" as a group or part of a group, refers to an unsaturated hydrocarbyl group, which may be linear, branched or cyclic, comprising one or more carbon-carbon double bonds. Alkenyl groups thus preferably comprise between 2 and 6 carbon atoms. Examples of alkenyl groups are ethenyl, 2-propenyl, 2-butenyl, 3-butenyl, 2-pentenyl and its isomers, 2-hexenyl and its isomers and the like.

In the compounds defined herein, the term "$C_{2-6}$alkynyl" as a group or part of a group, refers to a class of monovalent unsaturated hydrocarbyl groups, wherein the unsaturation arises from the presence of one or more carbon-carbon triple bonds. Alkynyl groups thus preferably comprise between 2 and 6 carbon atoms. Non limiting examples of alkynyl groups are ethynyl, 2-propynyl, 2-butynyl, 3-butynyl, 2-pentynyl and its isomers, 2-hexynyl and its isomers and the like.

In the compounds defined herein, the term "$C_{1-6}$alkoxy", as a group or part of a group, refers to a group having the Formula —$OR^a$ wherein $R^a$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

In the compounds defined herein, the term "$C_{6-10}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 10 atoms; wherein at least one ring is aromatic. The aromatic ring may optionally include one to two additional rings (either cycloalkyl, heterocyclyl or heteroaryl) fused thereto. Examples of suitable aryl include C6-10aryl, more preferably C6-8aryl. Non-limiting examples comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl. When the suffix "ene" is used in conjunction with an aryl group, this is intended to mean the aryl group as defined herein having two single bonds as points of attachment to other groups, such as phenylene, biphenylylene, naphthylene, indenylene, and the like. Where a carbon atom in an aryl group is replaced with a heteroatom, the resultant ring is referred to herein as a heteroaryl ring.

In the compounds defined herein, the term "$C_{6-10}$aryl-$C_{1-6}$alkyl", as a group or part of a group, means a $C_{1-6}$alkyl as defined herein, wherein at least one hydrogen atom is replaced by at least one $C_{6-10}$aryl as defined herein. Non-limiting examples of $C_{6-10}$aryl$C_{1-6}$alkyl group include benzyl, phenethyl, dibenzylmethyl, methylphenylmethyl, 3-(2-naphthyl)-butyl, and the like.

The term "proliferative disease or disorder" is meant to include all neoplastic cell growth and proliferation, whether malignant or benign, including all transformed cells and tissues and all cancerous cells and tissues. Proliferative diseases or disorders include, but are not limited to, premalignant or precancerous lesions, abnormal cell growths, benign tumours, malignant tumours, and cancer.

Additional examples of proliferative diseases and/or disorders include, but are not limited to neoplasms, whether benign or malignant, located in the prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and/or urogenital tract. In a preferred embodiment, the proliferative disorder involves tumour.

As used herein, the terms "tumour" or "tumour tissue" refer to an abnormal mass of tissue that results from excessive cell division. A tumour or tumour tissue comprises "tumour cells" which are neoplastic cells with abnormal growth properties and no useful bodily function. Tumours, tumour tissue and tumour cells may be benign or malignant. A tumour or tumour tissue may also comprise "tumour-associated non-tumour cells", e.g., vascular cells which form blood vessels to supply the tumour or tumour tissue. Non-tumour cells may be induced to replicate and develop by tumour cells, for example, the induction of angiogenesis in a tumour or tumour tissue. In another preferred embodiment, the proliferative disorder involves malignancy or cancer.

As used herein, the term "malignancy" refers to a non-benign tumour or a cancer. As used herein, the term "cancer" connotes a type of proliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioblastoma, cervical cancer, ovarian cancer, Kaposi's sarcoma, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, hematological cancer. The term "cancer" includes primary malignant cells or tumours (e.g., those whose cells have not migrated to sites in the subject's body other than the site of the original malignancy or tumour) and secondary malignant cells or tumours (e.g., those arising from metastasis, the migration of malignant cells or tumour cells to secondary sites that are different from the site of the original tumour).

In a further embodiment, the proliferative disorder is a premalignant condition. Premalignant conditions are known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell 1976 (Basic Pathology, 2d Ed., W. B. Saunders Co., Philadelphia, pp. 68-79).

"Hyperplasia" is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

"Metaplasia" is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

"Dysplasia" is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia. Additional preneoplastic disorders include, but are not limited to, benign dysproliferative disorders (e.g., benign tumours, fibrocystic conditions, tissue hypertrophy, intestinal polyps, colon polyps, and oesophageal dysplasia), leukoplakia, keratoses, Bowen's disease, Farmer's Skin, solar cheilitis, and solar keratosis.

In preferred embodiments, the proliferative disorder is chosen from glioma, preferably glioblastoma; prostate cancer; non-small-cell lung cancer (NSCLC); melanoma, head and neck cancer, pancreas cancer or colon cancer. By showing the anti-proliferative effect of the compounds of the invention on cell-lines derived from each of these cancertypes, the inventors realised that the above cancer types can particularly benefit from the methods and agents of the invention.

As used herein, the term "glioma" refers to its art-recognised connotation. By virtue of further illustration and not limitation, the term "glioma" refers to a tumour originating in the neuroglia of the brain or spinal cord. Gliomas can be derived from glial cell types, such as, e.g., astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults. Oligodendrogliomas typically occur in the cerebral hemispheres of adults. Malignant astrocytic gliomas are associated with the worst prognoses because of their ability to infiltrate diffusely into the normal brain parenchyma and include World Health Organization (WHO) grades II, III and grade IV tumors.

The present invention also provides methods of treating proliferative disorders in a subject needing such therapy, comprising administering a therapeutically effective amount of the compound or the pharmaceutical composition as defined herein.

As used herein, the terms "treat" or "treatment" refer to both therapeutic treatment and prophylactic or preventative measures, wherein the objective is to prevent or slow down (lessen) an undesired physiological change or disorder, such as the development or spread of proliferative disease, e.g., cancer. Beneficial or desired clinical results include, but are not limited to, alleviation of symptoms, diminishment of extent of disease, stabilised (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a phrase such as "a subject in need of treatment" includes subjects, such as mammalian subjects, that would benefit from treatment of a given condition, preferably a proliferative disease, such as, e.g., cancer, e.g., as above.

Such subjects will typically include, without limitation, those that have been diagnosed with the condition, preferably a proliferative disease, e.g., cancer, those prone to have or develop the said condition and/or those in whom the condition is to be prevented.

The term "therapeutically effective amount" refers to an amount of a compound or pharmaceutical composition as defined herein effective to treat a disease or disorder in a subject, i.e., to obtain a desired local or systemic effect and performance. By means of example and not limitation, in the case of proliferative disease, e.g., cancer, therapeutically effective amount of a drug may reduce the number of cancer cells; reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; enhance efficacy of another cancer therapy; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the cancer being treated. In particular, these terms refer to the quantity of compound or pharmaceutical composition according to the invention which is necessary to prevent, cure, ameliorate, or at least minimize the clinical impairment, symptoms, or complications associated with cancer in either a single or multiple doses.

The compound or the pharmaceutical composition as defined herein may be used alone or in combination with any of the cancer therapies selected from the group comprising chemotherapy, radiation therapy, immunotherapy, and/or gene therapy. As used herein the term "cancer therapy" is meant to encompass radiation therapy, chemotherapy, immunotherapy, gene-based therapy, surgery, as well as combinations thereof.

In another preferred embodiment the compound or the pharmaceutical composition as defined herein may be used alone or in combination with one or more active compounds that are suitable in the treatment of cancer. The term "active compound" refers to a compound other than the agents of the invention which is used to treat cancer. The active compounds may preferably be selected from the group comprising radiation therapeutics, chemotherapeutics including but not limited to temozolomide, vincristine, vinorelbine, procarbazine, carmustine, lomustine, taxol, peloruside, taxotere, tamoxifen, retinoic acid, 5-fluorouracil, cyclophosphamide and thalidomide.

The compound or the pharmaceutical composition as defined herein can thus be administered alone or in combination with one or more active compounds. The latter can be administered before, after or simultaneously with the administration of the said agent(s).

The term "pharmaceutically acceptable" as used herein is consistent with the art and means compatible with the other ingredients of a pharmaceutical composition and not deleterious to the recipient thereof.

The compounds as defined herein can optionally be formulated into a pharmaceutically acceptable salt. The term "pharmaceutically acceptable salt" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

The pharmaceutical composition as defined herein may further comprise at least one active compound, as defined above.

The pharmaceutical composition as defined herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods.

The pharmaceutical composition as defined herein can be prepared in a manner known per se to one of skill in the art.

For this purpose, at least one compound as defined herein or a pharmaceutically acceptable salt thereof as defined above, one or more solid or liquid pharmaceutical excipients and, if desired, in combination with other pharmaceutical active compounds, can be brought into a suitable administration form or dosage form which can then be used as a pharmaceutical in human medicine or veterinary medicine.

By means of non-limiting examples, such a formulation may be in a form suitable for oral administration, for parenteral administration (such as by intravenous, intramuscular, or subcutaneous injection, or intravenous infusion), for topical administration (including ocular), for administration by inhalation, by a skin patch, by an implant, by a suppository, etc. Such suitable administration forms—which may be solid, semi-solid, or liquid, depending on the manner of administration—as well as methods and carriers, diluents and excipients for use in the preparation thereof, will be clear to the skilled person as e.g. disclosed in standard textbooks, such as the latest edition of Remington's Pharmaceutical Sciences.

As non-limiting examples, the active compound as defined herein, together with one or more solid or liquid pharmaceutical carrier substances and/or additives (or auxiliary substances) and, if desired, in combination with other pharmaceutically active compounds having therapeutic or prophylactic action, can be brought into a suitable administration form or dosage form which can then be used as a pharmaceutical in human medicine. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the nucleic acid and/or the active compound and to use the resulting lyophilisates, for example, for preparing preparations for injection or infusion. Suitable carriers for microcapsules, implants or rods are, for example, copolymers of glycolic acid and lactic acid.

The pharmaceutical compositions as defined herein can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

For an oral administration form, the pharmaceutical compositions as defined herein can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate, and lactose and/or other excipients, binders, extenders, disintegrants, diluents, and lubricants known in the art.

The oral administration of a pharmaceutical composition as defined herein comprising at least one compound as defined herein, or a pharmaceutically acceptable salt or ester and/or solvate thereof, is suitably accomplished by uniformly and intimately blending together a suitable amount of said compound in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying, and suspending agents, dispersing agents, desintegrants, bulking agents, fillers, preserving agents, sweetening agents, flavoring agents, flow regulators, release agents, etc. The compositions may also be formulated so as to provide rapid, sustained, or delayed release of the active compound(s) contained therein, for example using liposomes or hydrophilic polymeric matrices based on natural gels or synthetic polymers.

The dosage or amount of compounds of the invention used, optionally in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the agent(s) of the invention.

In another embodiment, the invention provides a kit comprising a pharmaceutical composition as defined herein, and a further active compound as defined herein, for simultaneous, separate or sequential administration to a subject in need thereof.

In accordance with the method of treatment as defined herein, said pharmaceutical composition can be administered separately at different times during the course of therapy or concurrently in divided or single combination forms. The treatment method is therefore to be understood as embracing all such regimes of simultaneous or alternating treatment and the term "administering" is to be interpreted accordingly.

Essentially, the primary modes of treatment of solid tumor cancers comprise surgery, radiation therapy, and chemotherapy, separately and in combination. The compounds as defined herein are suitable for use in combination with these medicinal techniques. The compounds as defined herein may be useful in increasing the sensitivity of tumor cells to radiation in radiotherapy and also in potentiating or enhancing damage to tumors by chemotherapeutic agents. The compounds as defined herein and their pharmaceutically acceptable salts and/or solvates may also be useful for sensitizing multidrug-resistant tumor cells. The compounds as defined herein are useful therapeutic compounds for administration in conjunction with other drugs or therapies to potentiate their effect.

In another embodiment of the method of the invention, the administration may be performed with food, e.g., a high-fat meal. The term "with food" means the consumption of a meal either during or no more than about one hour before or after administration of a pharmaceutical composition according to the invention.

Oral administration of a pharmaceutical composition comprising at least one compound as defined herein, or a pharmaceutically acceptable salt or ester and/or solvate thereof can also be accomplished by preparing capsules or tablets containing the desired amount of said compound, optionally blended with a solid carrier as described above. Compressed tablets containing the pharmaceutical composition of the invention can be prepared by uniformly and intimately mixing the active ingredient with a solid carrier such as described above to provide a mixture having the necessary compression properties, and then compacting the mixture in a suitable machine to the shape and size desired. Molded tablets may be made by molding in a suitable machine, a mixture of powdered compound moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions, or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound as defined herein, if desired with the substances customary therefore such as solubilizers, emulsifiers, or further auxiliaries, are brought into solution, suspension, or emulsion. The compounds as defined herein can also be lyophilized and the lyophilizates obtained used, for example, for the production of injection or infusion preparations. Suitable solvents are, for example, water, physiological saline solution, or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents, or solvents, such as mannitol, 1,3-butanediol, water, Ringer's solution, or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters, or polyethylene glycols, which are solid at ordinary temperatures, but liquidify and/or dissolve in the rectal cavity to release the drug.

The pharmaceutical compositions as defined herein can be administered to humans in dosage ranges specific for each compound comprised in said compositions. The compounds comprised in said composition can be administered together or separately.

It will be understood, however, that specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also provides a new synthetic route to obtain the compounds as defined herein in large quantities.

Said new process for producing a compound according to general formula (I) of the invention, comprises the steps of:

(a) reacting a methyl-ketone having structural Formula IIa with an aldehyde having structural Formula IIb, through aldol coupling, wherein $P^5$ is a protecting group, executing suitable functional group interconversions, thereby obtaining a compound having structural Formula II;

(b) protecting the functional groups at positions $X^3$ and $X^4$ in the compound of Formula II where needed;

(c) reacting the compound of Formula II with a compound of the Formula III in the presence of a suitable catalyst, giving rise to a compound of the formula (IV), (d) removing the protecting groups $P^1$ and $P^4$ in the resulting compound and esterifying the deprotected COOH with the $C_{15}$ OH group, executing suitable functional group interconversions, thereby obtaining the lactone having structural Formula V; and (e) deprotecting $P^5$ in the compound having structural Formula V and deprotecting any of the possibly protected $X^1$, $X^2$, $X^3$, or $X^4$ groups, if required after executing additional suitable functional group interconversions, thereby obtaining a compound having structural Formula I, generally following the reaction scheme below:

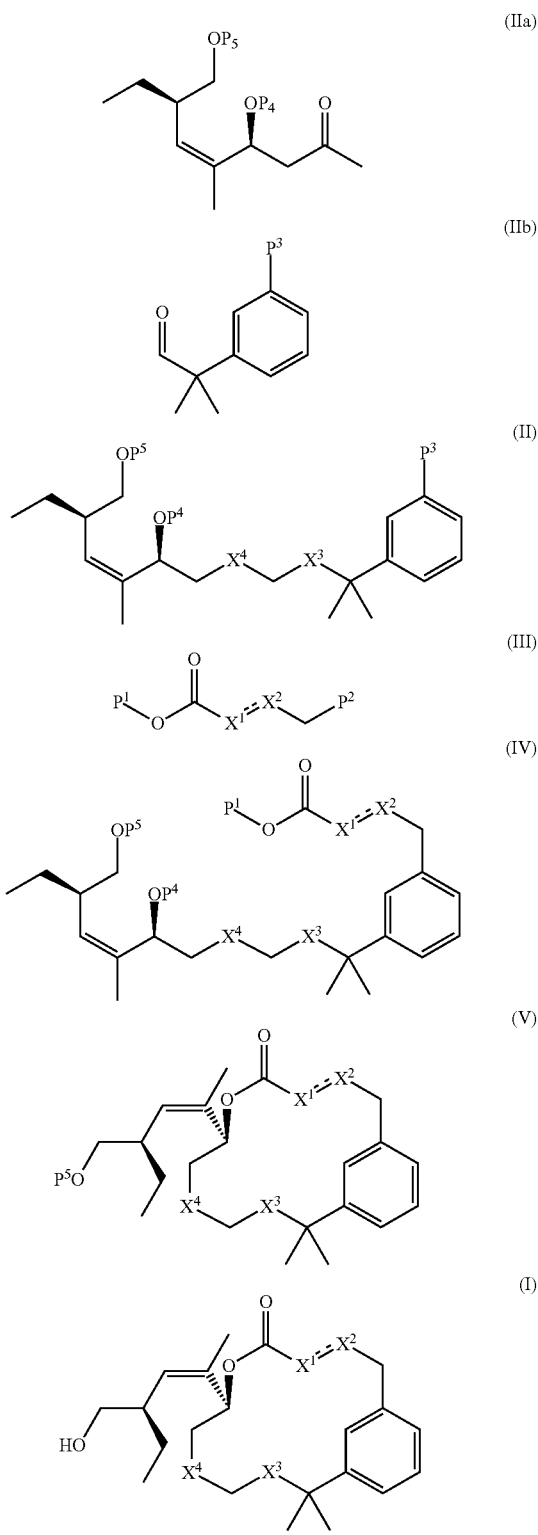

wherein $P^1$ is hydrogen or a carboxyl protecting group; for example optionally substituted alkyl, preferably $P^1$ is methyl;

$P^2$ is selected from halogen, pseudohalogen, $CF_3SO_3$, OAc, preferably $P^2$ is bromo, and simultaneously $P^3$ is a trialkyltin, such as trimethyltin or tri-n-butyltin, a boronic acid or a boronic ester;
or, alternatively,
P² is a trialkyltin, such as trimethyltin or tri-n-butyltin, a boronic acid or ester, and simultaneously P³ is selected from halogen, pseudohalogen, CF$_3$SO$_3$, OAc, (for example P³ is bromo);
P⁴ is selected from an orthogonally chosen protecting group, preferably P⁴ is MPM (4-OMe-Bn);
P⁵ is a protecting group which can be orthogonally removed, preferably selected from:
TBS (tert-butyldimethylsilyl) or MEM (2-methoxyethoxymethyl);
the suitable catalyst is typically a transition metal with ligands. For example, said suitable catalyst can be Pd$_2$(dba)$_3$.CHCl$_3$; and X$^1$, X$^2$, X$^3$, and X$^4$ have the same meaning as that defined above, and wherein, if present, their functional groups are suitably protected in steps (a) and (b), functionally interconverted where needed and deprotected accordingly in step (e).

Depending on the type of functional group or substituent on X$^1$, X$^2$, X$^3$, and X$^4$, there may be a different need to shield them from reacting with the other functional groups during the different coupling steps or to selectively prevent them to undergo a functional group interconversion. It may hence be needed to e.g. protect the functional groups of X$^1$, X$^2$, X$^3$, and X$^4$ in steps (a) and (b) and subsequently deprotect them accordingly in final step (e).

Such protective groups are known in the art. Preferred but non-limiting protective groups can be selected from the group comprising:
a) for hydroxyl groups: Methoxymethyl ether (MOM-OR), (2-Methoxyethoxy)methyl ether (MEM-OR), Tetrahydropyranyl ether (THP-OR), t-Butyl ether, Allyl ether, Benzyl ether (Bn-OR), t-Butyldimethylsilyl ether (TBDMS-OR), t-Butyldiphenylsilyl ether (TBDPS-OR), Acetic acid ester, Pivalic acid ester, Benzoic acid ester, and the like;
b) for carbonyl groups: Dimethyl acetal, 1,3-Dioxane, 1,3-Dioxolane, 1,3-Dithiane, N,N-Dimethylhydrazone, and the like;
c) for carboxyl groups: Methyl ester, Ethyl ester, t-Butyl ester, Benzyl ester, S-t-Butyl ester, 2-Alkyl-1,3-oxazoline, and the like;
d) for amino groups: 9-Fluorenylmethyl carbamate (Fmoc-NRR'), t-Butyl carbamate (Boc-NRR'), Benzyl carbamate (Z—NRR', Cbz-NRR'), Acetamide, Trifluoroacetamide, Phthalimide, Benzylamine (Bn-NRR'), Triphenylmethylamine (Tr-NRR'), Benzylideneamine, p-Toluenesulfonamide (Ts-NRR'), and the like.

The present invention is further illustrated by the following examples, which do not limit the scope of the invention in any way.

EXAMPLES

Example 1: First Synthesis of JC168

The first synthesis of JC168 was based on the aldol reaction between an enantiomerically pure aldehyde with an enantiomerically pure methylketone. This aldol reaction resulted in the wrong stereochemistry at C$_{13}$ and C$_{15}$. Therefore, extra steps (an oxidation/reduction sequence at C$_{13}$ and a Mitsunobu inversion at C$_{15}$) were needed to incorporate the correct stereochemistry. Other key steps involve two consecutive Stille couplings, asymmetric dihydroxylation and macrolactonization.

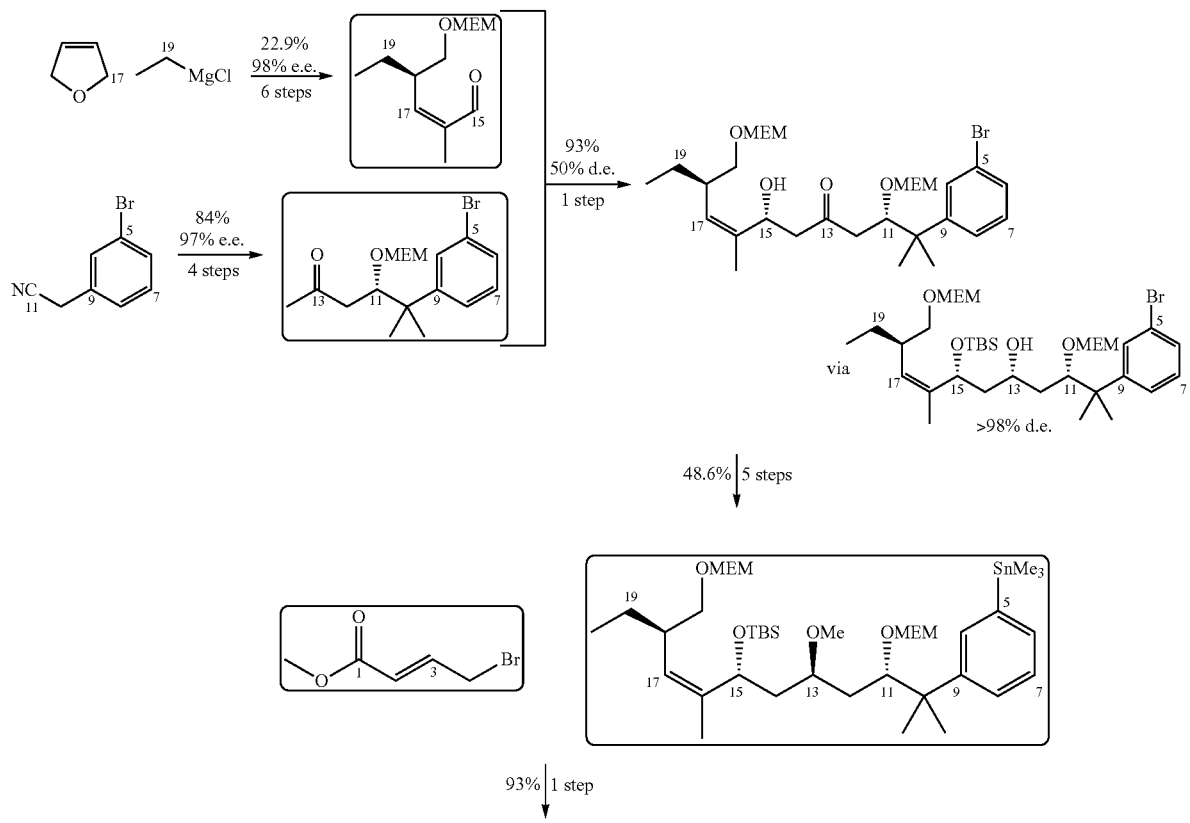

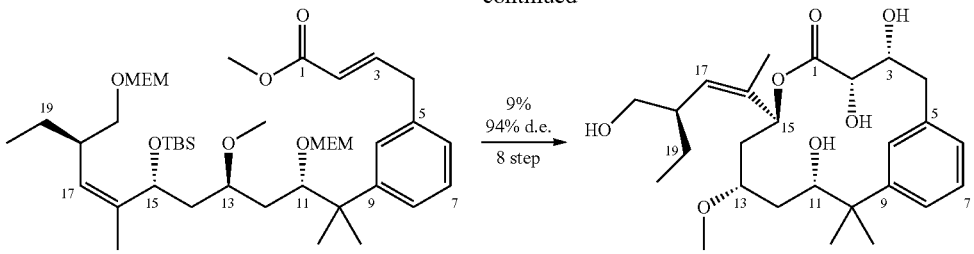

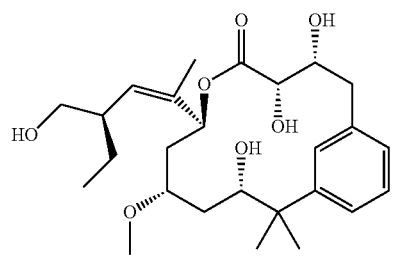

Figure 6:
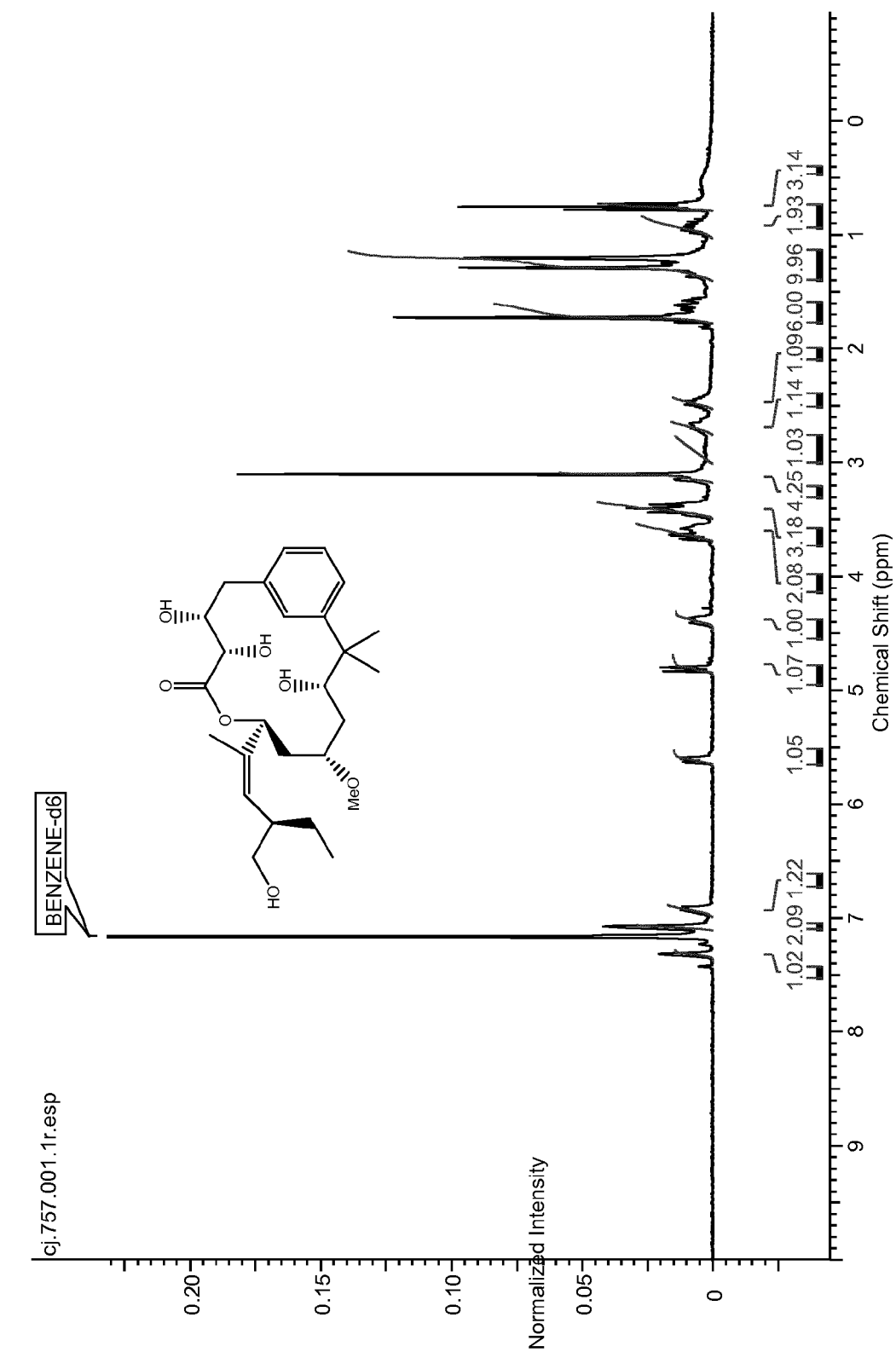
FIG. 6 represents the ¹H NMR spectrum of a compound according to an embodiment of the present invention namely the compound designated JC168.
Figure 7:
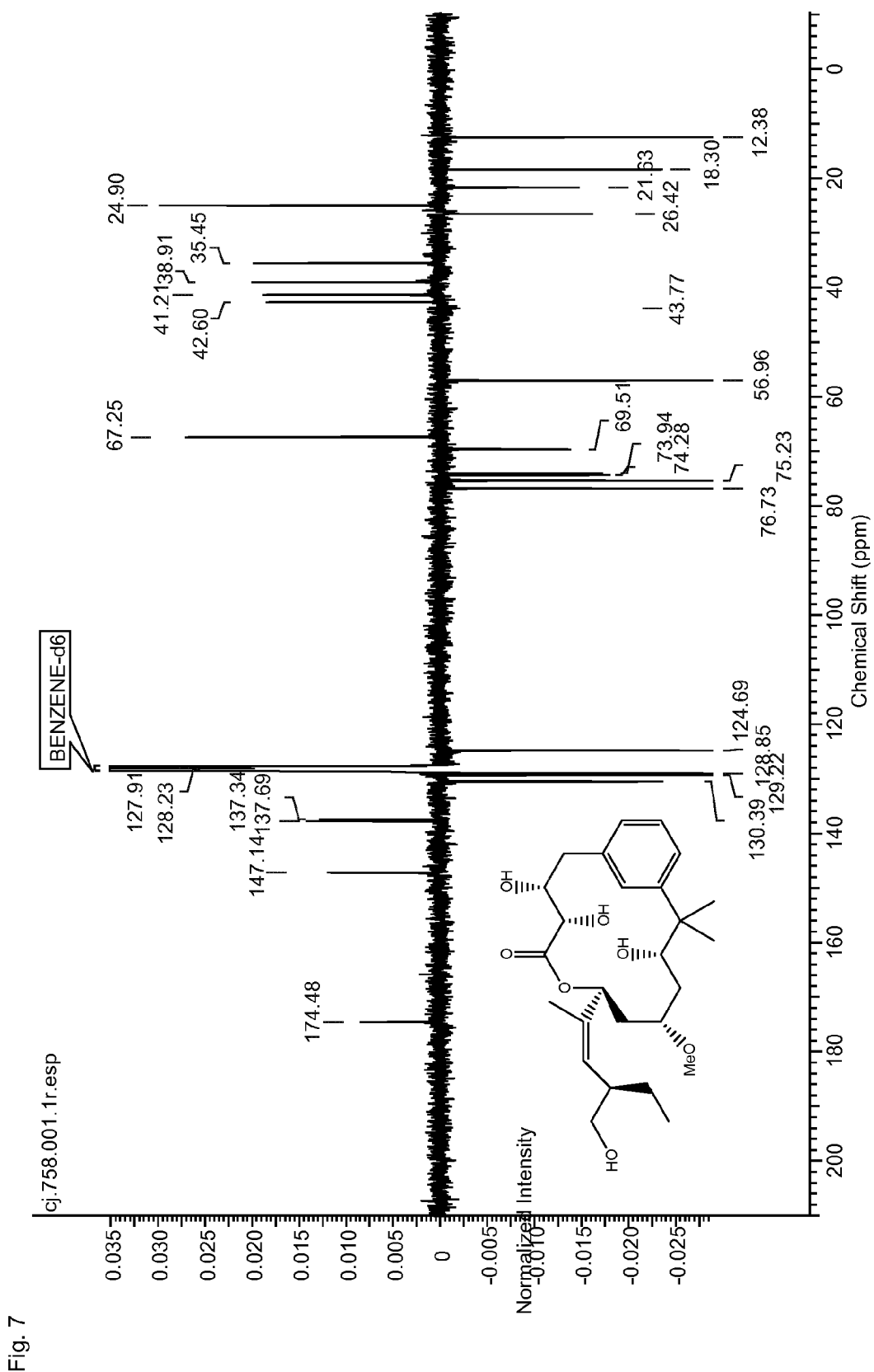
FIG. 7 represents the ¹³C NMR spectrum of a compound according to an embodiment of the present invention namely the compound designated JC168.

(1'Z,3R,3'R,4S,7S,9S,11S)-3,4,11-Trihydroxy-7-(3'-hydroxymethyl-1'-methylpent-1'-enyl)-9-methoxy-12,12-dimethyl-6-oxabicyclo[11.3.1]heptadeca-1(17),13,15-trien-5-one Formula: $C_{26}H_{40}O_7$
Molar Mass: 464.6 g/mol
$R_f$: 0.26 (pentane/acetone 6/4)
The $^1$H NMR spectrum of JC168 is provided in FIG. 6.
$^1$H NMR (300 MHz, $C_6D_6$): δ 7.31 (1H, s), 7.07 (2H, s with fine structure), 6.96-6.90 (1H, m), 5.61 (1H, dd, 3.4 Hz and 10.4 Hz), 4.81 (1H, d 10.4 Hz), 4.40-4.36 (1H, m), 3.65 (1H, 3.8 Hz and 10.6 Hz), 3.60-3.55 (1H, m), 3.15-3.09 (4H, m), 3.09-2.73 (1H, m), 2.73-2.61 (1H, m), 2.53-2.42 (1H, m), 1.82-1.55 (6H, m), 1.36-1.12 (10H, m), 1.01-0.86 (2H, m), 0.75 (3H, t, 7.3 Hz)
The $^{13}$C NMR spectrum of JC168 is provided in FIG. 7.
$^{13}$C NMR (75 MHz, $C_6D_6$): δ 174.48 (C), 147.14 (C), 137.69 (C), 137.35 (C), 130.40 (CH), 129.22 (CH), 128.86 (CH), 128.39-127.74 (C6D6+CH), 124.69 (CH), 76.74 (CH), 75.23 (CH), 74.28 (CH), 73.94 (CH), 69.52 (CH), 67.25 (CH2), 56.97 (CH3), 43.77 (CH), 42.60 (CH2), 41.21 (CH2), 38.91 (CH2), 35.45 (CH2), 26.42 (CH3), 24.90 (CH2), 21.63 (CH3), 18.30 (CH3), 12.38 (CH3)
ESI-MS (m/z): 465.2 (M+H$^+$)

Example 2: New Synthesis of JC168

The general synthesis route was described above and is now exemplified for compound JC 168. The process starts with the coupling of 2 fragments: a methylketone that already possesses the correct stereochemistry at $C_{15}$ and $C_{18}$, and a prochiral aldehyde (cf. Scheme below). Aldol coupling of those 2 fragments delivers a hydroxyketone with the correct stereochemistry at $C_{11}$. Key steps involve a samarium-mediated anti-reduction of this hydroxyketone, securing the correct stereochemistry at $C_{13}$, consecutive Stille couplings to complete the carbon-skeleton of pelofen, asymmetric dihydroxylation and macrolactonization.

Scheme 1: New synthesis route for JC 168

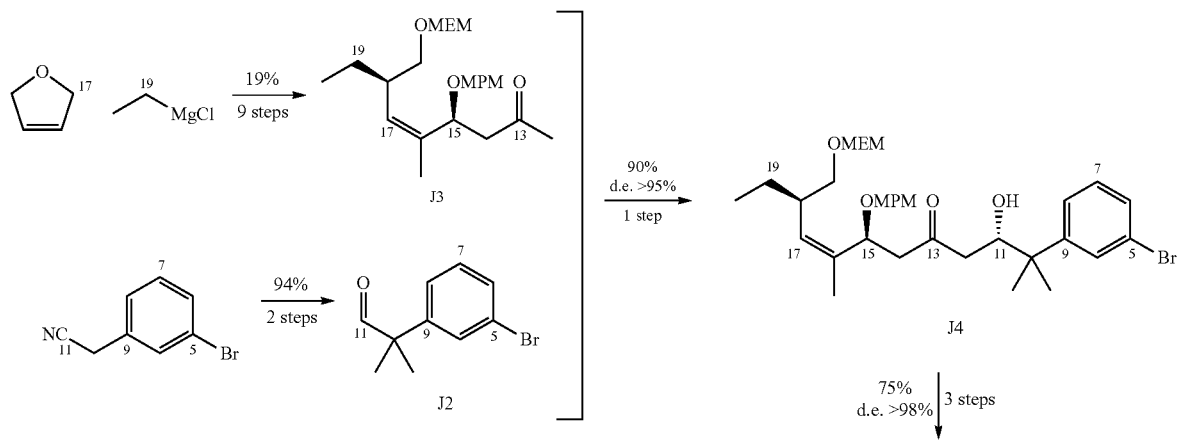

-continued

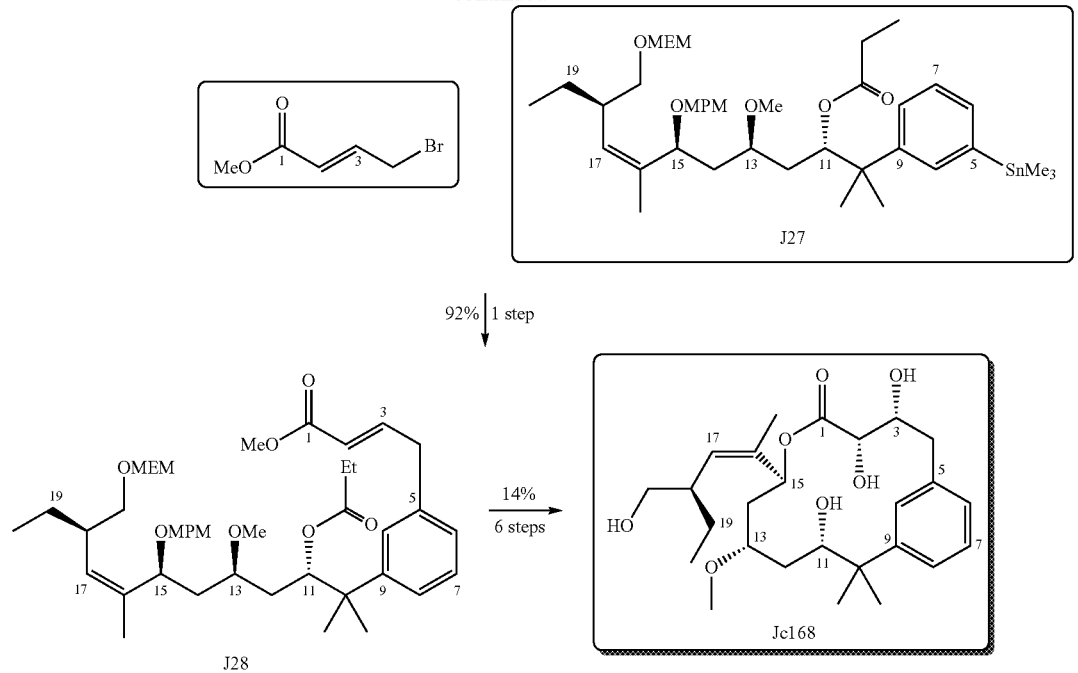

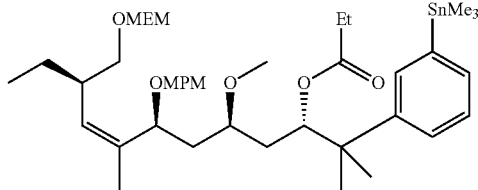

Compound J27

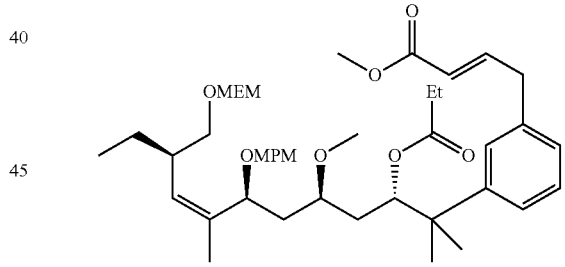

(3'S,5'R,7'S,10'R,Z)-5'-methoxy-7'-((4''-methoxybenzyl)oxy)-10'-(((2'''-methoxyethoxy)methoxy)methyl)-2',8'-dimethyl-2'-(3''''-(trimethylstannyl)phenyl)dodec-8'-en-3'-yl propionate Formula: $C_{40}H_{64}O_8Sn$
Molar Mass: 791.65 g/mol
$R_f$: 0.29 (pentane/diethylether 6/4)
$^1$H NMR (500 MHz, CDCl$_3$) δ 7.48 (app. d, J=2.2 Hz, 1H), 7.35-7.23 (m, 3H), 7.16 (app. d, J=8.7 Hz, 2H), 6.84 (app. d, J=8.7 Hz, 2H), 5.51 (dd, J=9.8, 2.1 Hz, 1H), 5.12 (dd, J=10.3, 1.4 Hz, 1H), 4.69 (d, J=6.7 Hz, 1H, A part of AB-spinsystem), 4.68 (d, J=6.7 Hz, 1H, B part of AB-spinsystem), 4.31 (d, J=11.1 Hz, 1H), 4.20 (dd, J=9.9, 2.9 Hz, 1H), 4.04 (d, J=11.2 Hz, 1H), 3.80 (s, 3H), 3.68-3.65 (m, 2H), 3.56-3.53 (m, 2H), 3.46 (dd, J=9.5, 5.7 Hz, 1H), 3.39 (dd, J=9.6, 6.7 Hz, 1H), 3.37 (s, 3H), 3.22 (s, 3H), 3.18-3.13 (m, 1H), 2.51-2.42 (m, 1H), 2.22 (app. q, J=7.6 Hz, 2H), 2.03 (ddd, J=14.1, 10.0, 4.0 Hz, 1H), 1.66 (d, J=1.4 Hz, 3H), 1.52-1.40 (m, 3H), 1.32-1.26 (m, 1H), 1.31 (s, 3H), 1.29 (s, 3H), 1.19-1.09 (m, 1H), 1.04 (app. t, J=7.6 Hz, 3H), 0.76 (app. t, J=7.5 Hz, 3H), 0.27 (s, 9H)
$^{13}$C NMR (125 MHz, CDCl$_3$) δ 174.00 (Cq), 159.12 (Cq), 145.86 (Cq), 141.76 (Cq), 136.44 (Cq), 133.84 (CH), 133.71 (CH), 131.23 (Cq), 131.12 (CH), 129.19 (2×CH), 127.81 (CH), 126.72 (CH), 113.84 (2×CH), 95.66 (CH$_2$), 76.79 (CH), 75.05 (CH), 73.36 (CH), 71.93 (CH$_2$), 71.51 (CH$_2$), 69.70 (CH$_2$), 66.87 (CH$_2$), 59.18 (CH$_3$), 56.46 (CH$_3$), 55.42 (CH$_3$), 41.95 (Cq), 39.26 (CH), 37.67 (CH$_2$), 35.18 (CH$_2$), 27.93 (CH$_2$), 26.03 (CH$_3$), 25.21 (CH$_2$), 23.66 (CH$_3$), 18.04 (CH$_3$), 11.91 (CH$_3$), 9.52 (CH$_3$), −9.41 (3×CH$_3$)

Compound J28 methyl (E)-4-(3'-((3''S,5''R,7''S,10''R,Z)-5''-methoxy-7''-((4'''-methoxybenzyl)oxy)-10''-(((2''''-methoxyethoxy)methoxy)methyl)-2'',8''-dimethyl-3''-(propionyloxy)dodec-8''-en-2''-yl)phenyl)but-2-enoate Formula: $C_{42}H_{62}O_{10}$
Molar Mass: 726.94 g/mol
$R_f$: 0.31 (pentane/diethylether 4/6)
$^1$H NMR (500 MHz, CDCl$_3$) δ 7.26-7.15 (m, 5H), 7.08 (app. dt, J=15.6, 6.8 Hz, 1H), 6.98 (app. dt, J=6.9, 1.7 Hz, 1H), 6.85 (app. d, J=8.7 Hz, 2H), 5.80 (app. dt, J=15.6, 1.6 Hz, 1H), 5.47 (dd, J=10.1, 1.9 Hz, 1H), 5.12 (dd, J=10.4, 1.5 Hz, 1H), 4.68 (d, J=6.7 Hz, 1H, A part of AB-spinsystem), 4.67 (d, J=6.7 Hz, 1H, B part of AB-spinsystem), 4.32 (d, J=11.3 Hz, 1H), 4.20 (dd, J=10.0, 3.0 Hz, 1H), 4.05 (d, J=11.3 Hz, 1H), 3.80 (s, 3H), 3.70 (s, 3H), 3.68-3.65 (m, 2H), 3.56-3.53 (m, 2H), 3.48 (app. dd, J=6.7, 1.8 Hz, 2H), 3.46 (dd, J=9.2, 5.9 Hz, 1H), 3.39 (dd, J=9.4, 6.7 Hz, 1H), 3.37 (s, 3H), 3.21 (s, 3H), 3.18-3.12 (m, 1H), 2.51-2.42 (m, 1H), 2.21 (app. q, J=7.6 Hz, 2H), 2.03 (ddd, J=14.2, 10.2, 3.9 Hz, 1H), 1.67 (d, J=1.4 Hz, 3H), 1.52-1.38 (m, 3H), 1.33-1.26 (m, 1H), 1.29 (s, 3H), 1.27 (s, 3H), 1.19-1.09 (m, 1H), 1.04 (app. t, J=7.6 Hz, 3H), 0.77 (app. t, J=7.4 Hz, 3H)

$^{13}$C NMR (125 MHz, CDCl$_3$) δ 173.94 (Cq), 167.13 (Cq), 159.12 (Cq), 147.92 (CH), 147.07 (Cq), 137.33 (Cq), 136.46 (Cq), 131.23 Cq), 131.11 (CH), 129.15 (2×CH), 128.50 (CH), 127.20 (CH), 126.63 (CH), 125.14 (CH), 121.95 (CH), 113.84 (2×CH), 95.66 (CH$_2$), 76.65 (CH), 74.97 (CH), 73.29 (CH), 71.93 (CH$_2$), 71.50 (CH$_2$), 69.65 (CH$_2$), 66.88 (CH$_2$), 59.18 (CH$_3$), 56.44 (CH$_3$), 55.42 (CH$_3$), 51.57 (CH$_3$), 41.87 (Cq), 39.28 (CH), 38.87 (CH$_2$), 37.61 (CH$_2$), 35.12 (CH$_2$), 27.91 (CH$_2$), 25.74 (CH$_3$), 25.22 (CH$_2$), 23.84 (CH$_3$), 18.03 (CH$_3$), 11.90 (CH$_3$), 9.49 (CH$_3$)

Example 3: Synthesis of C$_2$-C$_3$ analogue J74

3.1 Synthesis of J20

Preparation of (−)-Diisopinocampheylmethoxyborane:

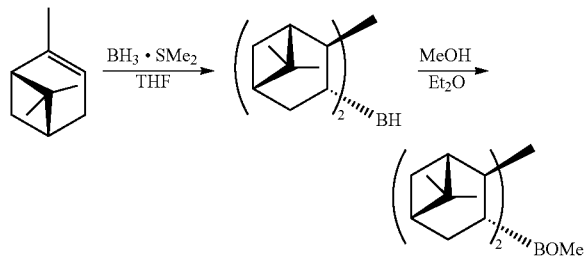

To a stirring solution of (+)-α-pinene, freshly distilled over CaH$_2$, (17.7 ml, 112 mmol, 2.5 eq.) in THF (13.4 ml) was added BH$_3$.SMe$_2$ (4.2 ml, 45 mmol, 1 eq.) over 30 minutes at a constant temperature of 23° C. After the addition, the stirring was stopped and the solution was left untouched overnight, during which white crystals were formed. The solution was then cooled to 0° C. for 2 h, after which the supernatants was removed using a double-ended needle. The white crystals were washed with precooled, dry Et$_2$O (3×8 ml) at 0° C., and dried, first by blowing Ar, then overnight in vacuo, yielding (−)-diisopinocampheylborane (11.4 g, 40 mmol, 89%).

(−)-diiospinocampheylborane (11.4 g, 40 mmol, 1 eq.), was suspended in Et$_2$O (40 ml) and cooled to 0° C. MeOH (1.6 ml, 40 mmol, 1 eq.) was then added dropwise and the solution was stirred at RT until everything had dissolved.

Allylation:

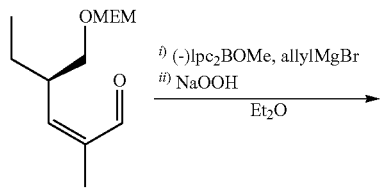

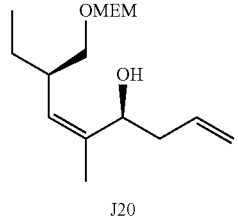

The solution of (−)-diisopinocampheylmethoxyborane (12.6 g, 40 mmol, 2.4 eq) in Et$_2$O (40 ml) was diluted with Et$_2$O (143 ml) and cooled to −78° C. Allylmagnesiumbromide (40 ml, 40 mmol, 1M in Et$_2$O) was added dropwise, upon which the reaction mixture became turbid and a black aggregate was formed. The reaction mixture was first stirred for 15 min at −78° C., followed by 1 h of stirring at RT, resulting in a white solution. The reaction mixture was then cooled back to −78° C., and a solution of the starting material (3.8 g, 17 mmol, 1 eq.) in Et$_2$O (26 ml) at −78° C. was added via a double-ended needle. The reaction mixture was stirred overnight during which the temperature was allowed to rise from −78° C. to −30° C. Tlc-analysis after 13 h (CH$_2$Cl$_2$/acetone 9/1) showed complete conversion of the starting material. The reaction was quenched by adding a solution of NaOOH in water. This solution was prepared beforehand by adding H$_2$O$_2$ (10.5 ml, 119 mmol, 7.2 eq.) to a solution of NaOH (3.2 g, 80 mmol, 4.8 eq.) in H$_2$O (26 ml) at 0° C. in a separate flask. The NaOH-solution was transferred to the reaction mixture at 0° C., after which it was stirred at RT for 4 h. The reaction mixture was then poured in aq. NH$_4$Cl (100 ml), the phases were separated and the aqueous phase was extracted with EtOAc (3×200 ml). The combined organic phases were dried over MgSO$_4$ and concentrated. Purification was accomplished by consecutive flash column chromatography (CH$_2$Cl$_2$/acetone 95/5; Hexane/acetone 8/2; CH$_2$Cl$_2$/acetone 88/12), yielding the target material J20 (3.6 g, 79%) as a clear, colorless oil.

Z-(4S,7R)-7-(((2'-methoxyethoxy)methoxy)methyl)-5-methylnona-1,5-diene-4-ol

Formula: C$_{15}$H$_{28}$O$_4$

Molar mass: 272.38

R$_f$: 0.15 (CH$_2$Cl$_2$/acetone 9/1)

ESI MS: 255.2 (M−H$_2$O+H$^+$)

[α]$_D$: −6.6° (c=8.4 mg/ml in CHCl$_3$)

IR (HATR): 3435 (b), 2929, 2876, 2186 (w), 2009 (w), 1982 (w), 1451, 1408, 1376, 1292, 1242, 1199, 1174, 1111 (m), 1095, 1044 (s), 1019 (s), 989 (m), 938, 911, 852 cm-1

$^1$H NMR (300 MHz, C6D6) δ 5.91 (app. dt, J=17.2, 10.3, 6.9 Hz, 1H), 5.10 (app. ddt, J=17.2, 3.6, 1.8 Hz, 1H), 5.03 (app. ddt, J=10.2, 2.3, 1.1 Hz, 1H), 4.94 (app. dd, J=9.9, 1.8 Hz, 1H), 4.64 (app. t, J=7.2 Hz, 1H), 4.48 (app. s, 2H), 3.59-3.46 (m, 2H), 3.36 (dd, J=9.1, 4.9 Hz, 1H), 3.33-3.26 (m, 2H), 3.14 (dd, J=17.9, 9.0 Hz, 1H), 3.11 (s, 3H), 2.65-2.50 (m, 1H), 2.39-2.28 (m, 1H), 1.89 (d, J=1.5 Hz, 3H), 1.36-1.21 (m, 1H), 1.14-0.97 (m, 1H), 0.78 (app. t, J=7.3 Hz, 3H)

$^{13}$C NMR (75 MHz, C6D$_6$) δ 140.46 (Cq), 136.31 (CH), 131.13 (CH), 116.87 (CH2), 95.86 (CH2), 72.55 (CH2), 71.76 (CH2), 69.25 (CH), 67.62 (CH2), 58.97 (CH3), 39.84 (CH), 39.37 (CH2), 25.60 (CH2), 18.60 (CH3), 12.29 (CH3)

3.2 Synthesis of J23

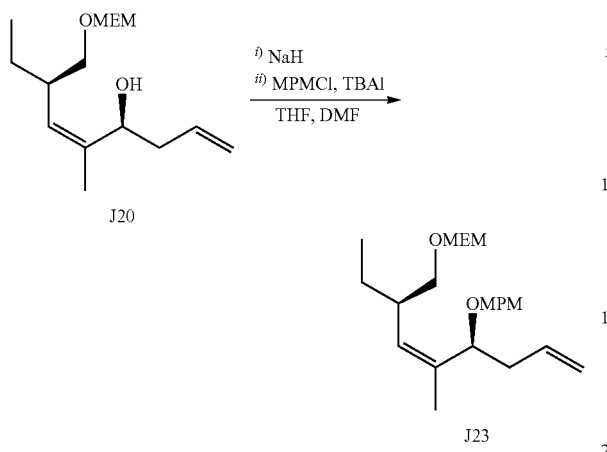

To a flask containing NaH (1.05 g, 26 mmol, 2 eq., 60 m % dispersion in mineral oil) was added a solution of the starting material J20 (3.58 g, 13 mmol, 1 eq.) in THF (40 ml) at 0° C. The reaction mixture was stirred for 30 min at RT, after which methoxyphenylmethyl-chloride (3.6 ml, 26 mmol, 2 eq.) was added dropwise via syringe, followed by a suspension of tetrabutylammoniumiodide (9.7 g, 26 mmol, 2 eq) in DMF (13 ml). The reaction was stirred at RT for 5 h, after which tlc-analysis ($CH_2Cl_2$/acetone 9/1) showed complete conversion of the starting material. The reaction mixture was then gently poured in a separation funnel containing water (200 ml), and extracted with $Et_2O$ (4×200 ml). The combined organic fractions were dried over $MgSO_4$, and concentrated. The product was purified by flash column chromatography (pentane/$Et_2O$ 8/2), yielding the desired product J23 as a clear yellow oil (5.10 g, 13 mmol, 99%)

Z-(4S,7R)-4-((4"-methoxybenzyl)oxy)-7-(((2'-methoxyethoxy)methoxy)methyl)-5-methylnona-1,5-diene Formula: $C_{23}H_{36}O_5$
Molar mass: 392.54
$R_f$: 0.31 (pentane/$Et_2O$ 6/4)
ESI MS: 410.2 ($M+NH_4^+$)
$[\alpha]_D$: −66.9° (c=7.6 mg/ml in $CHCl_3$)
IR (HATR): 3008 (w), 2933 (w), 2876 (w), 1613 (w), 1513, 1462 (w), 1455 (w), 1300 (w), 1247, 1214, 1172, 1110, 1095, 1075, 1049 (m), 991 (w), 916 (w), 847 (w), 823 (w), 751 (s), 666 $cm^{-1}$
$^1H$ NMR (300 MHz, C6D6) δ 7.39 (app. d, J=8.6 Hz, 2H), 6.86 (app. d, J=8.9 Hz, 2H), 5.96 (dddd, J=17.1, 10.2, 7.4, 6.8 Hz, 1H), 5.20 (dd, J=10.3, 2.0 Hz, 1H), 5.10 (app. ddd, J=17.1, 3.6, 1.4 Hz, 1H), 5.04 (app. ddt, J=10.1, 2.2, 1.1 Hz, 1H), 4.61 (app. s, 2H), 4.60 (d, J=11.7 Hz, 1H), 3.39 (dd, J=8.1, 5.8 Hz, 1H), 4.36 (d, J=11.7 Hz, 1H), 3.64-3.60 (m, 2H), 3.42 (app. dd, J=6.4, 3.1 Hz, 2H), 3.39-3.34 (m, 2H), 3.32 (s, 3H), 3.12 (s, 3H), 2.71-2.52 (m, 2H), 3.42 (app. dddt, J=14.1, 7.3, 5.9, 1.3 Hz, 1H), 1.80 (d, J=1.3 Hz, 3H), 1.61-1.46 (m, 1H), 1.27-1.11 (m, 1H), 0.83 (app. t, J=7.4 Hz, 3H)
$^{13}C$ NMR (75 MHz, C6D6) δ 160.98 (Cq), 136.84 (Cq), 136.34 (CH), 132.35 (CH+Cq), 129.67 (2×CH), 116.81 (CH2), 114.42 (2×CH), 96.12 (CH2), 77.12 (CH), 72.61 (CH2), 72.07 (CH2), 70.18 (CH2), 67.59 (CH2), 59.03 (CH3), 55.12 (CH3), 39.79 (CH), 39.54 (CH2), 25.92 (CH2), 18.47 (CH3), 12.33 (CH3)

3.3 Synthesis of J3

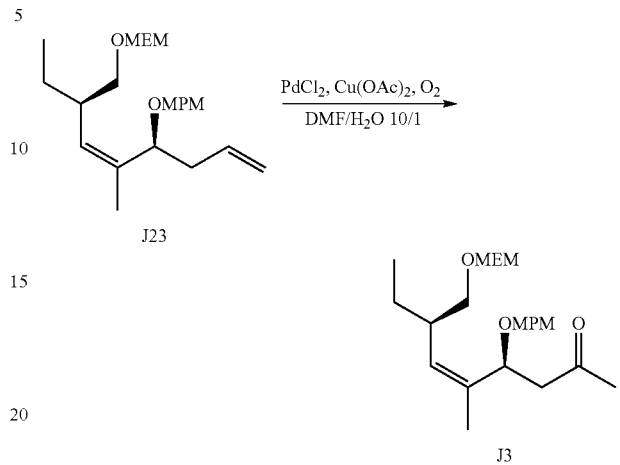

To a solution of the diene J23 (5.10 g, 13 mmol, 1 eq.) in a mixture of DMF (240 ml) and water (24 ml) was added $Cu(OAc)_2$ (3.94 g, 20 mmol, 1.5 eq.) in one portion and $PdCl_2$ (582 mg, 3.3 mmol, 0.25 eq.) in different portions. The reaction mixture was bubbled using $O_2$ and stirred at room temperature until tlc-analysis showed complete conversion of the starting material. The reaction mixture was then poured in water (500 ml) and extracted with $Et_2O$ (3×800 ml). The combined organic phases were dried over $MgSO_4$ and concentrated. After concentration, the crude product was filtered over a patch of Celite®, rinsed with $Et_2O$ (200 ml), and transferred to a separation funnel containing water (300 ml) using $Et_2O$ (100 ml). The phases were separated and the aqueous phase was extracted with $Et_2O$ (2×300 ml). Again, the combined organic phases were dried over $MgSO_4$ and concentrated. Purification via flash column chromatography (pentane/$Et_2O$ 6/4) delivered methyl ketone J3 as a clear yellow oil (4.88 g, 12 mmol, 91%).

Z-(4S,7R)-4-((4"-methoxybenzyl)oxy)-7-(((2'-methoxyethoxy) methoxy)methyl)-5-methylnon-5-en-2-one Formula: $C_{23}H_{36}O_6$
Molar mass: 408.53
$R_f$: 0.16 (pentane/diethylether 6/4)
ESI MS: 426.2 ($M+NH_4^+$); 431.2 ($M+Na^+$)
$[\alpha]_D$: −43.8° (c=8.0 mg/ml in $CHCl_3$)
IR (HATR): 3013 (w), 2957 (w), 2933 (w), 2871 (w), 1714, 1611 (w), 1514, 1462 (w), 1454 (w), 1358 (w), 1300 (w), 1248, 1216, 1173, 1092, 1049, 850 (w), 822 (w), 752 (s), 666 (w) $cm^{-1}$
$^1H$ NMR (300 MHz, C6D6) δ 7.33 (app. d, J=8.3 Hz, 2H), 6.82 (app. d, J=8.4 Hz, 2H), 5.18 (app. d, J=10.2 Hz, 1H), 5.01 (dd, J=9.4, 2.9 Hz, 1H), 4.60 (app. s, 2H), 4.55 (d, J=11.4 Hz, 1H), 4.38 (d, J=11.4 Hz, 1H), 3.66-3.58 (m, 2H), 3.48-3.34 (m, 4H), 3.30 (s, 3H), 3.13 (s, 3H), 2.78 (dd, J=15.4, 9.4 Hz, 1H), 2.78-2.65 (m, 1H), 2.12 (dd, J=15.4, 3.0 Hz, 1H), 1.80 (s, 3H), 1.75 (d, J=1.0 Hz, 3H), 1.59-1.43 (m, 1H), 1.24-1.07 (m, 1H), 0.81 (app. t, J=7.4 Hz, 3H)
$^{13}C$ NMR (75 MHz, C6D6) δ 205.02 (Cq), 160.04 (Cq), 136.12 (Cq), 132.60 (CH), 131.90 (Cq), 129.89 (2×CH), 114.42 (2×CH), 96.11 (CH2), 73.90 (CH), 72.62 (CH2), 72.02 (CH2), 70.60 (CH2), 67.60 (CH2), 59.03 (CH3), 55.11 (CH3), 48.30 (CH2), 39.98 (CH), 31.17 (CH3), 25.76 (CH2), 18.54 (CH3), 12.27 (CH3)

3.4 Synthesis of J4

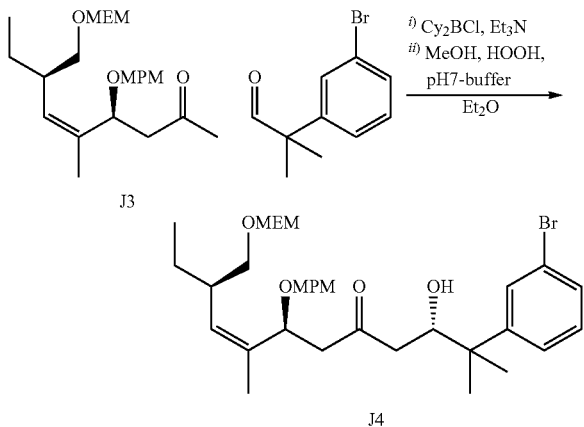

To a stirred solution of ketone J3 (353 mg, 0.86 mmol, 1 eq.) in Et$_2$O (10 ml) was added triethylamine (205 µl, 1.47 mmol, 1.7 eq.) at RT. The solution was then cooled to 0° C. and chlorodicylcohexylborane (1.3 ml, 1.3 mmol, 1.5 eq., 1 M in hexane) was added dropwise, upon which the reaction mixture became turbid. After stirring for 30 min at 0° C., the reaction mixture was further cooled to −15° C. A solution of aldehyde (588 mg, 2.59 mmol, 3 eq.) in Et$_2$O (2 ml) was then added via a double-ended needle and the flask containing the aldehyde was rinsed with Et$_2$O (3×1 ml). The reaction mixture was stirred for 20 h at −11° C., after which tlc-analysis showed complete conversion of the starting material (hexane/acetone 8/2). The reaction was quenched by consecutive addition of pH 7 phosphate buffer (9 ml), MeOH (9 ml) and H$_2$O$_2$ (1 ml, 13 mmol, 15 eq., 35 v % in H$_2$O) and stirred for 3 h at room temperature. The reaction mixture was then poured into a separation funnel containing water (100 ml), extracted with CH$_2$Cl$_2$ (3×100 ml), dried over MgSO$_4$ and concentrated. Purification using gradient flash column chromatography (hexane/acetone 95/5 to hexane/acetone 9/1) yielded the hydroxyketone J4 as a clear colorless oil (481 mg, 0.75 mmol, 87%).

(3S,7S,10R,Z)-2-(3'-bromophenyl)-3-hydroxy-7-((4''-methoxybenzyl)oxy)-10-(((2'''-methoxyethoxy)methoxy)methyl)-2,8-dimethyldodec-8-en-5-one Formula: C$_{33}$H$_{47}$BrO$_7$
Molar mass: 635.63
R$_f$: 0.32 (hexane/acetone 8/2)
HR-MS: calculated (M+NH$_4^+$) 652.2843. found 652.2850. calculated (M+Na$^+$) 657.2397. found 657.2411.

$^1$H NMR (500 MHz, CD$_2$Cl$_2$) δ 7.52 (app. t, J=1.9 Hz, 1H), 7.34 (ddd, J=7.8, 2.1, 1.0 Hz, 1H), 7.31 (ddd, J=8.0, 1.9, 1.0 Hz, 1H), 7.20-7.14 (m, 3H), 6.85 (app. d, 8.7 Hz, 2H), 5.18 (dd, J=10.5, 1.5 Hz, 1H), 4.72 (dd, J=10.1, 3.0 Hz, 1H), 4.64 (d, J=6.6 Hz, 1H, A part of AB-spinsystem), 4.63 (d, J=6.6 Hz, 1H, B part of AB-spinsystem), 4.31 (d, J=11.1 Hz, 1H), 4.124 (d, J=11.1 Hz, 1H), 4.118 (dd, J=10.5, 1.8 Hz, 1H), 3.79 (s, 3H), 3.63-3.60 (m, 2H), 3.51-3.48 (m, 2H), 3.46 (dd, J=9.4, 5.8 Hz, 1H), 3.37 (dd, J=9.4, 7.0 Hz, 1H), 3.31 (s, 3H), 2.85 (dd, J=15.3, 10.1 Hz, 1H), 2.62-2.53 (m, 1H), 2.43 (dd, J=17.2, 1.8 Hz, 1H), 2.26 (dd, J=17.2, 10.4 Hz, 1H), 2.20 (dd, J=15.3, 3.0 Hz, 1H), 1.69 (d, J=1.4 Hz, 3H), 1.55-1.45 (m, 1H), 1.28 (s, 3H), 1.26 (s, 3H), 1.20-1.10 (m, 1H), 0.78 (app. t, J=7.5 Hz, 3H)

$^{13}$C NMR (125 MHz, CD$_2$Cl$_2$) δ 210.22 (Cq), 159.59 (Cq), 150.01 (Cq), 135.28 (Cq), 132.56 (CH), 131.10 (Cq), 130.30 (CH), 130.06 (CH), 129.73 (2×CH), 129.49 (CH), 125.90 (CH), 122.73 (Cq), 113.99 (2×CH), 95.84 (CH2), 74.65 (CH), 73.51 (CH), 72.21 (CH2), 71.71 (CH2), 70.15 (CH2), 67.13 (CH2), 58.98 (CH3), 55.61 (CH3), 48.03 (CH2), 46.16 (CH2), 42.16 (Cq), 39.71 (CH), 25.35 (CH2), 25.12 (CH3), 23.66 (CH3), 17.97 (CH3), 11.92 (CH3)

3.5 Synthesis of J7

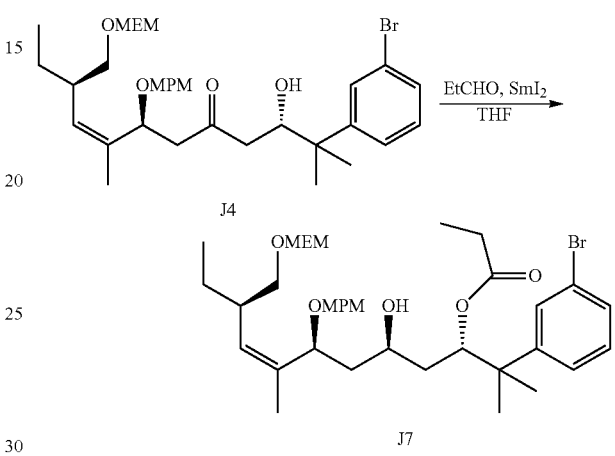

To a solution of propionaldehyde (200 µl, 2.79 mmol, 4 eq.) in THF (5 ml) was added SmI$_2$ (3.5 ml, 0.35 mmol, 0.5 eq., 0.1M solution in THF) at 0° C. The solution colored blue, changed rapidly to green and in the end to yellow. The solution was further cooled to −20° C. and a solution of hydroxyketone J4 (443 mg, 0.70 mmol, 1 eq.) in THF (2 ml) was added using a double-ended needle and the flask containing the starting material was rinsed with THF (5 ml). The reaction was stirred at −20° C. for 4 hours, after which tlc-analysis (hexane/acetone 8/2) showed complete conversion (There was only a very subtle difference in Rf-value, however, when looking at the back of the tlc-plate after staining with the molybdate containing reagent, the starting material had a red/pink shine, whereas the target material had a blue/green shine). The reaction was quenched by adding NaHCO$_3$ (15 ml) and water (10 ml), extracted with EtOAc (3×25 ml), dried over MgSO$_4$ and concentrated.

Purification using flash column chromatography (hexane/acetone 87.5/12.5) delivered alcohol J7.

(3S,5R,7S,10R,Z)-2-(3'-bromophenyl)-5-hydroxy-7-((4''-methoxybenzyl)oxy)-10-(((2'''-methoxyethoxy)methoxy)methyl)-2,8-dimethyldodec-8-en-3-yl propionate Formula: C$_{36}$H$_{53}$BrO$_8$
Molar mass: 693.71
R$_f$: 0.25 (hexane/acetone 8/2)
HRMS: calculated (M+NH$_4^+$) 710.3262. found 710.3254. calculated (M+Na$^+$) 715.2816. found 715.2823.

$^1$H NMR (500 MHz, CDCl$_3$) δ 7.49 (app. t, J=1.9 Hz, 1H), 7.33 (ddd, J=7.8, 2.0, 1.0 Hz, 1H), 7.31 (ddd, J=7.9, 2.0, 1.0 Hz, 1H), 7.20-7.14 (m, 3H), 6.84 (app. d, J=8.7 Hz, 2H), 5.33 (dd, J=10.8, 1.8 Hz, 1H), 5.18 (dd, J=10.4, 1.6 Hz, 1H), 4.68 (d, J=7.0 Hz, 1H, A part of AB-spinsystem), 4.67 (d, J=7.0 Hz, 1H, B part of AB-spinsystem), 4.43 (dd, J=9.1, 4.7

Hz, 1H), 4.36 (d, J=11.2 Hz, 1H), 4.15 (d, J=11.2 Hz, 1H), 3.79 (s, 3H), 3.67-3.64 (m, 2H), 3.55-3.52 (m, 2H), 3.52-3.46 (m, 1H), 3.47 (dd, J=9.5, 5.9 Hz, 1H), 3.39 (dd, J=9.4, 6.8 Hz, 1H), 3.36 (s, 3H), 2.57-2.48 (m, 1H), 2.27 (qd, J=7.6, 3.8 Hz, 2H), 1.87 (app. dt, J=14.3, 9.0 Hz, 1H), 1.67 (d, J=1.4 Hz, 3H), 1.51-1.31 (m, 4H), 1.300 (s, 3H), 1.297 (s, 3H), 1.19-1.12 (m, 1H), 1.08 (app. t, J=7.6 Hz, 3H), 0.79 (app. t, J=7.5 Hz, 3H)

$^{13}$C NMR (125 MHz, CDCl$_3$) δ 174.87 (Cq), 159.24 (Cq), 148.91 (Cq), 135.48 (Cq), 132.15 (CH), 130.79 (Cq), 129.93 (CH), 129.86 (CH), 129.47 (CH), 129.37 (2×CH), 125.41 (CH), 122.55 (Cq), 113.95 (2×CH), 95.67 (CH$_2$), 76.84 (CH), 76.01 (CH), 71.93 (CH$_2$), 71.41 (CH$_2$), 69.61 (CH$_2$), 66.88 (CH$_2$), 59.17 (CH), 55.42 (CH$_3$), 41.90 (Cq), 40.80 (CH$_2$), 39.18 (CH), 38.12 (CH$_2$), 27.91 (CH$_2$), 25.26 (CH$_3$), 25.22 (CH$_2$), 24.21 (CH$_3$), 17.87 (CH$_3$), 11.81 (CH$_3$), 9.40 (CH$_3$)

Preparation of SmI$_2$ (Szostak et al., *J. Org. Chem.*, 2012, 77 (7), pp 3049-3059).

Metallic samarium (601 mg, 4 mmol, 2 eq.) was first activated by stirring dry in a flask fitted with a rubber septum for 2 days under Ar atmosphere. After activation, THF (16.5 ml) was added to the metal, followed by a red solution of I$_2$ (508 mg, 2 mmol, 1 eq.) in THF (3.5 ml). The septum was then replaced by a glass stopper and the brown reaction mixture was heated to 60° C. Stirring was continued for 24 h at 60° C., after which the solution turned dark blue. The mixture was cooled down to RT and the flask was fitted with a septum again and flushed with argon. This procedure yielded a solution of SmI$_2$ in THF with a concentration of 0.1 M. Upon stirring, the solution can be maintained for a couple of days. Two hours before using it, stirring had to be stopped.

3.6. Synthesis of J26

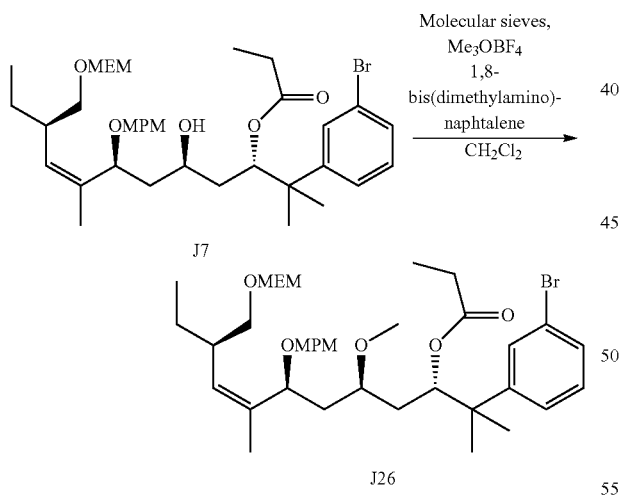

To a solution of alcohol J7 (811 mg, 1.17 mmol, 1 eq.) in CH$_2$Cl$_2$ (29 ml) were added molecular sieves (4 Å) (470 mg), and the suspension was stirred at RT. After 30' 1,8-bis(dimethylamino)naphtalene (652 mg, 3.04 mmol, 2.6 eq.) and trimethyloxonium tetrafluoroborate (433 mg, 2.92 mmol, 2.5 eq.) were added, respectively. The mixture was stirred for 24 h, after which tlc-analysis (hexane/acetone 8/2) showed complete conversion of the starting material. The reaction mixture was filtered, rinsed with 100 ml EtOAc and washed with a solution of CuSO$_4$ in water (2×80 ml, 1M). The aqueous phases were combined and extracted with EtOAc (3×150 ml). All organic phases were collected, dried over MgSO$_4$ and concentrated in vacuo. Flash column chromatography (hexane/EtOAc 7/3) delivered the methylether J26 (805 mg, 1.14 mmol, 97%) as a clear oil.

(3S,5R,7S,10R,Z)-2-(3'-bromophenyl)-5-methoxy-7-((4''-methoxybenzyl)oxy)-10-(((2'''-methoxyethoxy)methoxy)methyl)-2,8-dimethyldodec-8-en-3-yl propionate Formula: C$_{37}$H$_{55}$BrO$_8$
Molar mass: 707.74
R$_f$: 0.31 (hexane/acetone 8/2)

$^1$H NMR (500 MHz, CDCl$_3$) δ 7.50 (app. t, J=1.9 Hz, 1H) 7.32 (app. dd, J=7.9, 1.9 Hz, 2H) 7.18-7.13 (m, 3H) 6.85 (app. d, J=8.7 Hz, 2H) 5.42 (dd, J=9.8, 2.3 Hz, 1H) 5.12 (dd, J=10.5, 1.0 Hz, 1H) 4.69 (d, J=6.7 Hz, 1H, A part of AB-spinsystem) 4.68 (d, J=6.7 Hz, 1H, B part of AB-spinsystem) 4.31 (d, J=11.2 Hz, 1H) 4.19 (dd, J=10.1, 2.6 Hz, 1H) 4.04 (d, J=11.3 Hz, 1H) 3.81 (s, 3H) 6.68-3.65 (m, 2H) 3.56-3.53 (m, 2H) 3.47 (dd, J=9.2, 5.9 Hz, 1H) 3.41-3.36 (m, 1H) 3.38 (s, 3H) 3.23 (s, 3H) 3.18-3.12 (m, 1H) 2.50-2.42 (m, 1H) 2.24 (app. q, J=7.6 Hz, 2H) 2.04 (ddd, J=14.1, 10.3, 3.7 Hz, 1H) 1.67 (d, J=1.3 Hz, 3H) 1.53-1.38 (m, 3H) 1.33-1.27 (m, 1H) 1.275 (s, 3H) 1.266 (s, 3H) 1.18-1.10 (m, 1H) 1.06 (app. t, J=7.6 Hz, 3H) 0.77 (app. t, J=7.4 Hz, 3H)

$^{13}$C NMR (125 MHz, CDCl$_3$) δ 173.88 (Cq), 159.11 (Cq), 149.03 (Cq), 136.46 (Cq), 131.20 (Cq), 130.00 (CH), 129.76 (CH), 129.36 (CH), 129.22 (2×CH), 125.55 (CH), 122.45 (Cq), 113.86 (2×CH), 95.66 (CH$_2$), 76.36 (CH), 74.93 (CH), 73.23 (CH), 71.93 (CH$_2$), 71.54 (CH$_2$), 69.69 (CH$_2$), 66.88 (CH$_2$), 59.18 (CH$_3$), 56.58 (CH$_3$), 55.44 (CH$_3$), 42.04 (Cq), 39.33 (CH), 37.49 (CH$_2$), 35.20 (CH$_2$), 27.90 (CH$_2$), 25.56 (CH$_3$), 25.22 (CH$_2$), 24.04 (CH$_3$), 18.04 (CH$_3$), 11.95 (CH$_3$), 9.50 (CH$_3$), 3.7 Synthesis of S2

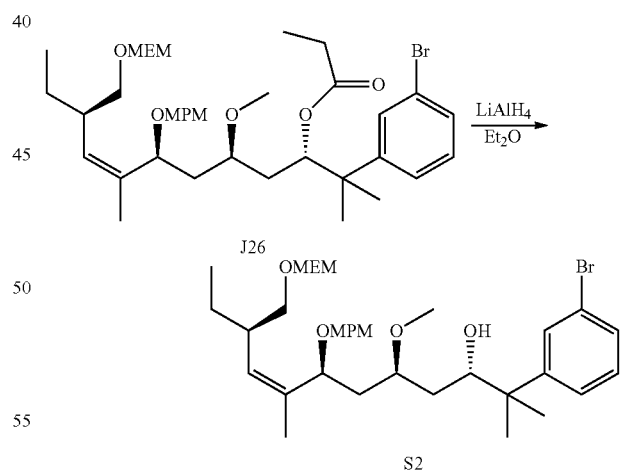

To a cooled (0° C.) suspension of LiAlH$_4$ (152 mg, 4.01 mmol, 3 eq.) in Et$_2$O (32 ml) was added a solution of ester J26 (946 mg, 1.34 mmol, 1 eq.) in Et$_2$O (32 ml) using a double-ended needle. The solution was stirred for 1 h at 0° C., upon which tlc-analysis (hexane/EtOAc 7/3) indicates full conversion of the starting material. The excess LiAlH$_4$ was quenched by adding EtOAc (10 ml). Then, a saturated aqueous solution of Rochelle's salt (25 ml) was added, and the resulting mixture was stirred for 1 h at RT. The mixture was transferred to a separation funnel containing another portion of a saturated aqueous solution of Rochelle's salt (25 ml), extracted with EtOAc (3×50 ml), dried over MgSO₄ and concentrated. Flash column chromatography (hexane/acetone 8/2) delivered alcohol S2 (871 mg, 1.34 mmol, 100%) as an oil.

(3S,5S,7S,10R,Z)-2-(3'-bromophenyl)-5-methoxy-7-((4''-methoxybenzyl)oxy)-10-(((2'''-methoxyethoxy)methoxy)methyl)-2,8-dimethyldodec-8-en-3-ol Formula: $C_{34}H_{51}BrO_7$
Molar mass: 651.67
$R_f$: 0.40 (hexane/acetone 7/3)
$^1$H NMR (500 MHz, CDCl₃) δ 7.49 (app. t, J=1.9 Hz, 1H), 7.32 (ddd, J=7.9, 2.0, 1.0 Hz, 1H), 7.29 (ddd, J=7.9, 1.8, 1.0 Hz, 1H), 7.21 (app. d, J=8.8 Hz, 2H), 7.16 (app. t, J=7.9 Hz, 1H), 6.86 (app. d, J=8.7 Hz, 2H), 5.17 (dd, J=10.4, 1.6 Hz, 1H), 4.70 (d, J=6.7 Hz, 1H, A part of AB-spinsystem), 4.69 (d, J=6.7 Hz, 1H, B part of AB-spinsystem), 4.35 (d, J=11.3 Hz, 1H), 4.24 (dd, J=10.0, 3.3 Hz, 1H), 4.04 (d, J=11.3 Hz, 1H), 3.81 (s, 3H), 3.81-3.78 (m, 1H), 3.69-3.66 (m, 2H), 3.56-3.50 (m, 3H), 3.50 (dd, J=9.4, 5.9 Hz, 1H), 3.42 (dd, J=9.5, 6.9 Hz, 1H), 3.37 (s, 3H), 3.25 (s, 3H), 2.97 (bs, 1H), 2.57-2.48 (m, 1H), 2.17 (ddd, J=14.3, 10.1, 4.2 Hz, 1H), 1.71 (d, J=1.5 Hz, 3H), 1.58-1.50 (m, 1H), 1.49 (ddd, J=14.3, 7.8, 3.3 Hz, 1H), 1.43 (ddd, J=14.8, 10.3, 4.6 Hz, 1H), 1.34 (ddd, J=14.7, 5.9, 2.0 Hz, 1H), 1.24-1.17 (m, 1H), 1.23 (s, 3H), 1.22 (s, 3H), 0.83 (app. t, J=7.5 Hz, 3H)
$^{13}$C NMR (125 MHz, CDCl₃) δ 159.31 (Cq), 150.10 (Cq), 136.19 (Cq), 131.54 (CH), 130.87 (Cq), 130.07 (CH), 129.72 (CH), 129.64 (2×CH), 129.12 (CH), 125.63 (CH), 122.56 (Cq), 113.93 (2×CH), 95.69 (CH₂), 77.33 (CH), 75.88 (CH), 73.08 (CH), 71.93 (CH₂), 71.47 (CH₂), 69.63 (CH₂), 66.89 (CH₂), 59.18 (CH₃), 56.55 (CH₃), 55.46 (CH₃), 42.64 (Cq), 39.31 (CH), 36.26 (CH₂), 33.53 (CH₂), 25.28 (CH₂), 24.53 (CH₃), 23.98 (CH₃), 18.12 (CH₃), 11.87 (CH₃)

3.8 Synthesis of S3

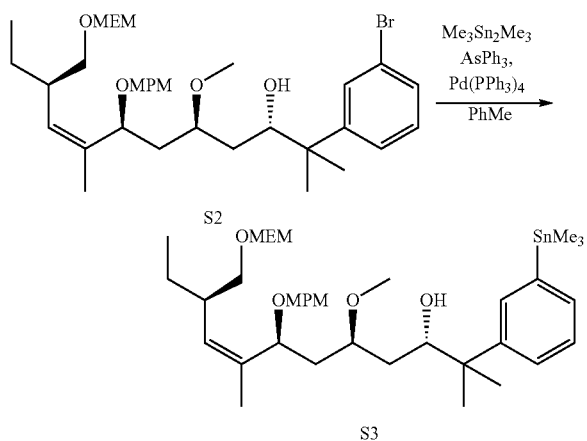

In a pressure tube was added to a solution of alcohol S2 (873 mg, 1.34 mmol, 1 eq.) in toluene (13 ml), respectively hexamethylditin (555 μl, 2.68 mmol, 2 eq.), AsPh₃ (164 mg, 0.54 mmol, 0.4 eq.) and tetrakis(triphenylphosphine)palladium(0) (50 mg, 34 μmol, 3.3 mol %). The solution was heated to 70° C. and stirred for 94 h, after which there was clear formation of Pd-black. Although tlc-analysis (hexane/acetone 8/2) did not show complete conversion, the reaction was quenched using a saturated aqueous solution of NaHCO₃ (15 ml) and water (15 ml). The aqueous phase was extracted with EtOAc (3×30 ml), dried over MgSO₄ and concentrated. Starting and target material were isolated together using flash column chromatography (hexane/acetone 8/2). This mixture was then put back into reaction, using the same conditions as described above. Every 20 h fresh catalyst (50 mg, 34 μmol, 3.3 mol %) was added for 3 times. Quenching and workup was accomplished as described. After performing flash column chromatography, the mixture of starting and target material was put into reaction for a 3rd time, but now using 4 eq. of hexamethylditin, to prevent homo-coupling. Quenching and workup proceeded exactly as described above. Flash column chromatography (hexane/acetone 9/1) now provided the stannane S3 (804 mg, 1.09 mmol, 81%) as a sticky oil.

(3S,5S,7S,10R,Z)-5-methoxy-7-((4'-methoxybenzyl)oxy)-10-(((2''-methoxyethoxy)methoxy)methyl)-2,8-dimethyl-2-(3'''-(trimethylstannyl)phenyl)dodec-8-en-3-ol Formula: $C_{37}H_{60}O_7Sn$
Molar mass: 735.58
$R_f$: 0.28 (hexane/acetone 8/2)
1H NMR (500 MHz, CDCl₃) δ 7.49-7.47 (m, 1H), 7.33-7.27 (m, 3H), 7.21 (app. d, J=8.7 Hz, 2H) 6.85 (app. d, J=8.7 Hz, 2H), 5.17 (dd, J=10.5, 1.7 Hz, 1H), 4.70 (d, J=6.7 Hz, 1H, A part of AB-spinsystem), 4.69 (d, J=6.7 Hz, 1H, B part of AB-spinsystem), 4.34 (d, J=11.3 Hz, 1H), 4.28 (dd, J=9.6, 3.5 Hz, 1H), 4.06 (d, J=11.3 Hz, 1H), 3.87 (dd, J=10.1, 3.4 Hz, 1H), 3.80 (s, 3H), 3.68-3.65 (m, 2H), 3.56-3.50 (m, 3H), 3.49 (dd, J=9.3, 5.8 Hz, 1H), 3.42 (dd, J=9.3, 6.8 Hz, 1H), 3.37 (s, 3H), 3.24 (s, 3H), 2.66 (d, J=3.4 Hz, 1H), 2.60-2.51 (m, 1H), 2.15 (ddd, J=14.4, 9.7, 4.5 Hz, 1H), 1.70 (d, J=1.4 HZ, 3H), 1.56-1.46 (m, 3H), 1.41 (ddd, J=14.4, 6.4, 2.1 Hz, 1H), 1.28 (s, 3H), 1.25 (s, 3H), 1.24-1.16 (m, 1H), 0.83 (app. t, J=7.5 Hz, 3H), 0.27 (s, 9H, satellite peaks: J=27.5, 26.2 Hz)
$^{13}$C NMR (125 MHz, CDCl₃) δ 159.24 (Cq), 146.93 (Cq), 141.96 (Cq), 136.28 (Cq), 133.85 (CH), 133.60 (CH), 131.44 (CH), 131.00 (Cq), 129.62 (2×CH), 127.84 (CH), 126.79 (CH), 113.90 (2×CH), 95.69 (CH₂), 77.21 (CH), 76.05 (CH), 73.35 (CH), 71.93 (CH₂), 71.44 (CH₂), 69.71 (CH₂), 66.88 (CH₂), 59.18 (CH₃), 56.43 (CH₃), 55.43 (CH₃), 42.54 (Cq), 39.23 (CH), 36.75 (CH₂), 34.04 (CH₂), 25.29 (CH₂), 24.43 (CH₃), 23.73 (CH₃), 18.33 (CH₃), 11.85 (CH₃), −9.34 (3×CH₃)

3.9 Synthesis of D1

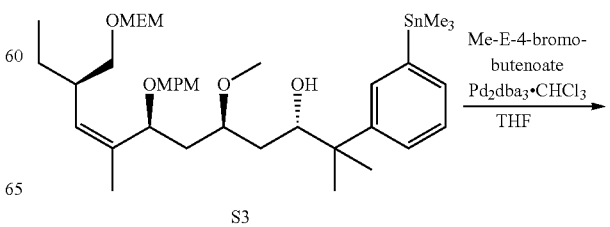

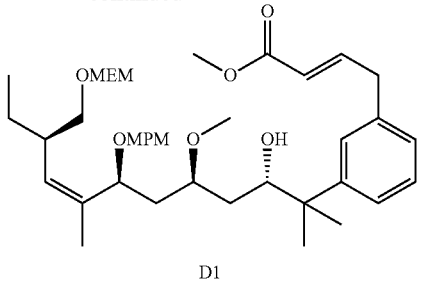

D1

To a solution of stannane S3 (250 mg, 0.34 mmol, 1 eq.) in THF (1.7 ml) were added methyl-E-4-bromobutenoate (81 μl, 0.68 mmol, 2 eq.) and Pd₂dba₃.CHCl₃ (5 mg, 5.1 μmol, 1.5 mol %) in a pressure tube and the resulting red-brown mixture was heated to 70° C., upon which it coloured yellow. Tlc-analysis (hexane/acetone 7/3) after 4 h showed complete conversion of the starting material. The reaction was then quenched with a saturated aqueous solution of NaHCO₃ (15 ml), extracted with CH₂Cl₂ (4×15 ml), dried over MgSO₄ and concentrated. Flash column chromatography (hexane/acetone 8/2) yielded the unsaturated ester D1 (228 mg, 0.34 mmol, 100%) as a yellow oil.

Methyl (E)-4-(3'-((3"S,5"S,7"S,10"R,Z)-3"-hydroxy-5"-methoxy-7"-((4'''-methoxybenzyl)oxy)-10"-(((2''''-methoxyethoxy)methoxy)methyl)-2",8"-dimethyldodec-8"-en-2"-yl)phenyl)but-2-enoate Formula: $C_{39}H_{58}O_9$
Molar mass: 670.87
$R_f$: 0.14 (hexane/acetone 8/2)
¹H NMR (500 MHz, CDCl₃) δ 7.25-7.19 (m, 4H), 7.16-7.14 (m, 1H), 7.09 (app. dt, J=15.6, 6.9 Hz, 1H), 7.00-6.97 (m, 1H), 6.85 (app. d, J=8.9 Hz, 2H), 5.81 (app. dt, J=15.4, 1.7 Hz, 1H), 5.17 (app. dd, J=10.4, 1.5 Hz, 1H), 4.70 (d, J=6.7 Hz, 1H, A part of AB-spinsystem), 4.69 (d, J=6.7 Hz, 1H, B part of AB-spinsystem), 4.35 (d, J=11.4 Hz, 1H), 4.27 (dd, J=9.8, 3.4 Hz, 1H), 4.05 (d, J=11.3 Hz, 1H), 3.83 (ddd, J=10.3, 3.4, 2.0 Hz, 1H), 3.80 (s, 3H), 3.71 (s, 3H), 3.68-3.65 (m, 2H), 3.56-3.46 (m, 6H), 3.42 (dd, J=9.4, 6.8 Hz, 1H), 3.37 (s, 3H), 3.23 (s, 3H), 2.80 (d, J=3.4 Hz, 1H), 2.59-2.50 (m, 1H), 2.16 (ddd, J=14.1, 9.6, 4.6 Hz, 1H), 1.70 (d, J=1.6 Hz, 3H), 1.57-1.46 (m, 2H), 1.44 (ddd, J=14.7, 10.2, 4.6 Hz, 1H), 1.36 (ddd, J=14.5, 6.2, 2.0 Hz, 1H), 1.27-1.19 (m, 1H), 1.24 (s, 3H), 1.23 (s, 3H), 0.83 (app. t, J=7.5 Hz, 3H)
¹³C NMR (125 MHz, CDCl₃) δ 167.06 (Cq), 159.26 (Cq), 148.08 (Cq), 148.00 (CH), 137.36 (Cq), 136.25 (Cq), 131.46 (CH), 130.95 (Cq), 129.64 (2×CH), 128.48 (CH), 127.29 (CH), 126.42 (CH), 125.21 (CH), 121.92 (CH), 113.90 (2×CH), 95.68 (CH₂), 77.26 (CH), 76.01 (CH), 73.20 (CH), 71.92 (CH₂), 71.42 (CH₂), 69.64 (CH₂), 66.88 (CH₂), 59.17 (CH₃), 56.45 (CH₃), 55.42 (CH₃), 51.59 (CH₃), 42.44 (Cq), 39.24 (CH), 38.92 (CH₂), 36.53 (CH₂), 33.72 (CH₂), 25.28 (CH₂), 24.45 (CH₃), 23.97 (CH₃), 18.11 (CH₃), 11.83 (CH₃)

3.10 Synthesis of J70

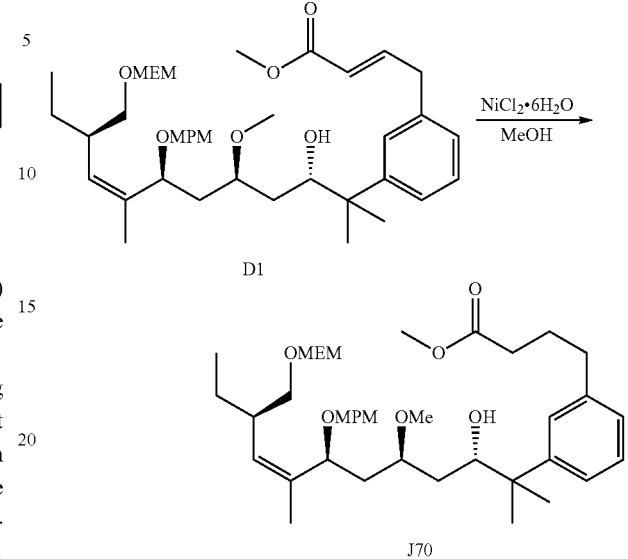

To a solution of ester unsaturated ester D1 (111 mg, 0.18 mmol, 1 eq.) in MeOH (3.6 ml), was added NiCl₂.6H₂O (1 mg, 0.7 μmol, 4 mol %) and the red solution was cooled to 0° C. Then, NaBH₄ (14 mg, 0.36 mmol, 2 eq.) was added, gas started to evolve and the solution turned first brown, then black. After 10', tlc-analysis (hexane/acetone 8/2) showed complete conversion of the starting material, upon which the reaction mixture was filtered over Celite® and concentrated. Flash column chromatography (hexane/acetone 8/2) yielded saturated ester J70 (116 mg, 0.17 mmol, 96%) as a colorless oil.

Methyl 4-(3'-((3"S,5"S,7"S,10"R,Z)-3"-hydroxy-5"-methoxy-7"-((4'''-methoxybenzyl)oxy)-10"-(((2''''-methoxyethoxy)methoxy)methyl)-2",8"-dimethyldodec-8"-en-2"-yl)phenyl)-butanoate Formula: $C_{39}H_{60}O_9$
Molar mass: 672.90
$R_f$: 0.3 (hexane/acetone 8/2)
HRMS: calculated (M+Na⁺) 695.4130. found 695.4115.
$[\alpha]_D$: −48.2° (c=7.3 mg/ml)
¹H NMR (500 MHz, CDCl₃) δ (7.23-7.16 (m, 5H), 7.00 (app. dt, J=6.7, 1.8 Hz, 1H), 6.85 (app. d, J=8.7 Hz, 2H), 5.17 (dd, J=10.5, 1.6 Hz, 1H), 4.69 (d, J=6.6 Hz, 1H, A part of AB-spinsystem), 4.68 (d, J=6.6 Hz, 1H, B part of AB-spinsystem), 4.34 (d, J=11.3 Hz, 1H), 4.28 (dd, J=9.6, 3.5 Hz, 1H), 4.07 (d, J=11.3 Hz, 1H), 3.85 (dd, J=9.5, 2.8 Hz, 1H), 3.80 (s, 3H), 3.69-3.65 (m, 2H), 3.66 (s, 3H), 3.56-3.48 (m, 3H), 3.49 (dd, J=9.5, 5.9 Hz, 1H), 3.42 (dd, J=9.4, 6.7 Hz, 1H), 3.37 (s, 3H), 3.24 (s, 3H), 2.65-2.52 (m, 3H), 2.32 (app. t, J=7.4 Hz), 2H), 2.15 (ddd, J=14.4, 9.8, 4.5 Hz, 1H), 1.98-1.91 (m, 2H), 1.70 (d, J=1.4 Hz, 3H), 1.56-1.37 (m, 4H), 1.27 (s, 3H), 1.25 (s, 3H), 1.24-1.18 (m, 1H), 0.84 (app. t, J=7.5 Hz, 3H)
¹³C NMR (125 MHz, CDCl₃) δ 174.05 (Cq), 159.34 (Cq), 147.70 (Cq), 141.14 (Cq), 136.38 (Cq), 131.41 (CH), 131.18 (Cq), 129.56 (2×CH), 128.22 (CH), 127.08 (CH), 126.11 (CH), 124.52 (CH), 113.98 (2×CH), 95.77 (CH₂), 77.26 (CH), 76.10 (CH), 73.49 (CH), 72.01 (CH₂), 71.54 (CH₂), 69.76 (CH₂), 66.98 (CH₂), 59.13 (CH₃), 56.41 (CH₃), 55.45 (CH₃), 51.56 (CH₃), 42.48 (Cq), 39.29 (CH), 36.95 (CH₂), 35.62 ($CH_2$), 34.23 ($CH_2$), 33.67 ($CH_2$), 26.79 ($CH_2$), 25.35 ($CH_2$), 24.54 ($CH_3$), 23.94 ($CH_3$), 18.10 ($CH_3$), 11.78 ($CH_3$)

3.11 Synthesis of J71

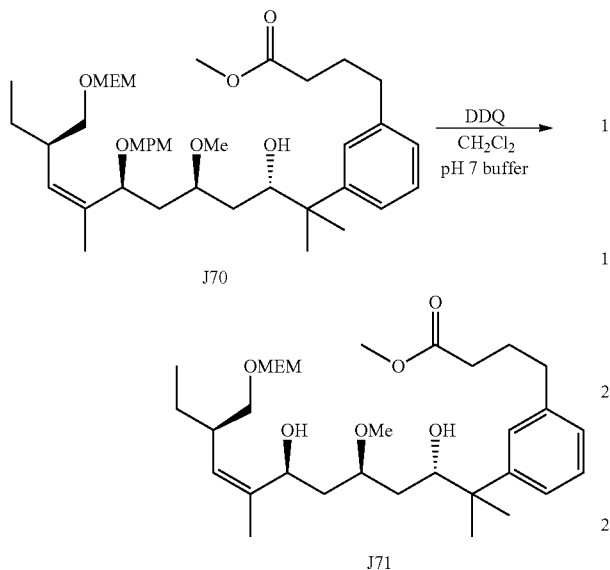

To a solution of ester J70 (68 mg, 102 µmol, 1 eq.) in $CH_2Cl_2$ (5 ml) and pH 7 phosphate buffer (0.5 ml) at 0° C. was added 2,3-dichloro-5,6-dicyanobenzoquinone (115 mg, 508 µmol, 5 eq.) in one portion. The reaction mixture was stirred at 0° C. for 2 h, after which tlc-analysis (hexane/acetone 8/2) showed complete conversion of the starting material. The reaction was quenched using a saturated aqueous solution of $NaHCO_3$ (5 ml) and water (5 ml), diluted with $CH_2Cl_2$ (5 ml) and the phases were separated. The aqueous phase was extracted with $CH_2Cl_2$ (3×10 ml), the combined organic phases were dried over $MgSO_4$ and concentrated. Flash column chromatography (hexane/acetone 8/2) provided diol J71 as a colorless oil (53 mg, 96 µmol, 96%).

Methyl-4-(3'-((3"S,5"R,7"S,10"R,Z)-3",7"-dihydroxy-5"-methoxy-10"-(((2'"-methoxyethoxy)methoxy)methyl)-2",8"-dimethyldodec-8"-en-2"-yl)phenyl)butanoate Formula: $C_{31}H_{52}O_8$
Molar mass: 552.74
$R_f$: 0.07 (hexane/acetone 8/2)
HR-MS: calculated for (M+Na$^+$) 575.3554. found 575.3550.
$[\alpha]_D$: −15.8° (c=7.3 mg/ml)
$^1$H NMR (500 MHz, CDCl$_3$) δ 7.25-7.18 (m, 3H), 7.04-6.99 (m, 1H), 4.97 (dd, J=10.1, 1.6 Hz, 1H), 4.68 (d, J=6.8 Hz, 1H, A part of AB-spinsystem), 4.66 (d, J=6.8 Hz, 1H, B part of AB-spinsystem), 4.57 (dd, J=8.7, 4.6 Hz, 1H), 3.90 (dd, J=10.2, 1.4 Hz, 1H), 3.67-3.61 (m, 2H), 3.65 (s, 3H), 3.56-3.44 (m, 4H), 3.38 (s, 3H), 3.29-3.23 (m, 1H), 3.28 (s, 3H), 3.00 (bs, 1H), 2.84 bs, 1H), 2.64-2.54 (m, 3H), 2.33 (app. t, J=15.2 Hz, 2H), 2.03 (ddd, J=14.4, 8.5, 6.9 Hz, 1H), 1.99-1.91 (m, 2H), 1.70 (d, J=1.3 Hz, 3H), 1.62-1.38 (m, 4H), 1.33 (s, 3H), 1.32 (s, 3H), 1.23-1.12 (m, 1H), 0.84 (app. t, J=7.5 Hz, 3H)
$^{13}$C NMR (125 MHz, CDCl$_3$) δ 174.11 (Cq), 147.49 (Cq), 141.19 (Cq), 139.60 (Cq), 130.67 (CH), 128.27 (CH), 127.02 (CH), 126.23 (CH), 124.42 (CH), 95.50 ($CH_2$), 78.66 (CH), 76.24 (CH), 71.90 ($CH_2$), 71.26 ($CH_2$), 67.02 ($CH_2$), 66.49 (CH), 59.15 ($CH_3$), 56.80 ($CH_3$), 51.66 ($CH_3$), 42.46 (Cq), 39.30 (CH), 37.27 ($CH_2$), 35.57 ($CH_2$), 34.25 ($CH_2$), 33.61 ($CH_2$), 26.78 ($CH_2$), 25.04 ($CH_2$), 24.51 ($CH_3$), 23.82 ($CH_3$), 18.30 ($CH_3$), 11.95 ($CH_3$)

3.12 Synthesis of J72

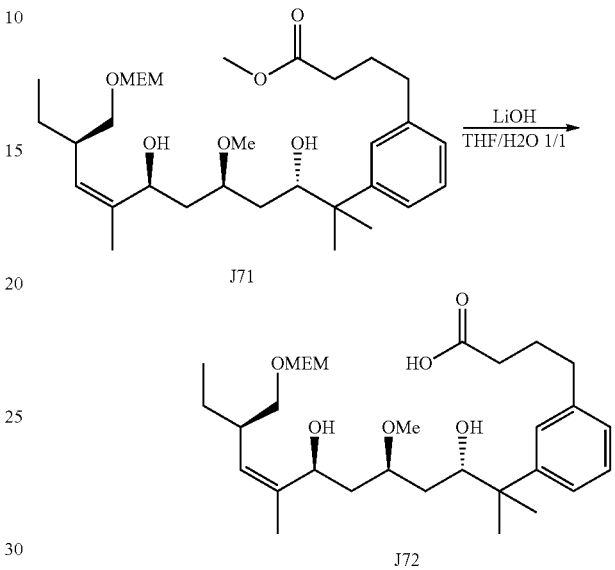

To a solution of diol J71 (10 mg, 18 µmol, 1 eq.) in a mixture of THF (360 µl) and water (360 µl) was added LiOH.H$_2$O (7 mg, 180 mmol, 10 eq.) at RT. The reaction mixture was stirred overnight. Tlc-analysis (hexane/acetone 6/4) indicated complete conversion of the starting material. The reaction mixture was then poured into a saturated aqueous NH$_4$Cl solution (5 ml), extracted with EtOAc (5×5 ml), dried over MgSO$_4$ and concentrated. Dry toluene (1 ml) was added to the crude product and evaporated, yielding carboxylic acid J72 (10 mg, 18 µmol, 100%) as a clear oil, which was used without further purification.

4-(3-((3S,5R,7S,10R,Z)-3,7-dihydroxy-5-methoxy-10-(((2-methoxyethoxy)methoxy)methyl)-2,8-dimethyldodec-8-en-2-yl)phenyl)butanoic acid Formula: $C_{30}H_{50}O_8$
Molar mass: 538.72
$R_f$: 0.55 ($CH_2Cl_2$/MeOH/AcOH 95/5/1)

3.13 Synthesis of J73

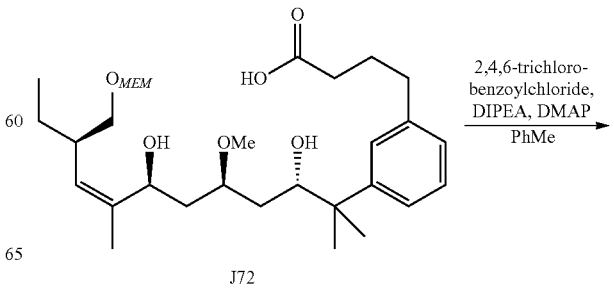

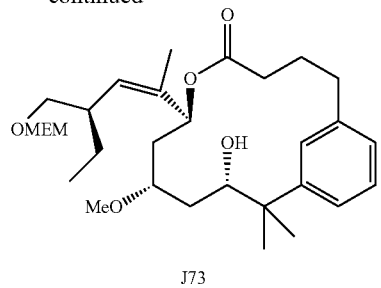

J73

To a solution of the crude carboxylic acid J72 (10 mg, 18 μmol, 1 eq.) in PhMe (540 μl) was added consecutive DIPEA (24 μl, 135 μmol, 7.5 eq.) and 2,4,6-trichlorobenzoylchloride (14 μl, 90 μmol, 5 eq.) at RT. After 45' of anhydride formation, the reaction mixture was diluted with PhMe (5 ml), and sucked into a syringe. The flask was rinsed with PhMe (4.4 ml in 3 times) and everything was added to the same syringe. The solution containing the anhydride (10 ml total volume) was then added at RT over 12 h (0.8 ml/h) to a solution of DMAP (55 mg, 450 mmol, 25 eq.) in PhMe (18 ml) using a syringe pump. 22 h after the start of the addition, tlc-analysis ($CH_2Cl_2$/MeOH/AcOH 95/5/1) showed complete conversion of the starting material. The reaction was poured into diluted HCl (20 ml, 0.1 M) and the phases were separated. The aqueous phase was extracted with EtOAc (2×30 ml), the combined organic phases were washed with a saturated aq. $NaHCO_3$-solution (25 ml), dried over $MgSO_4$ and concentrated. Purification using flash column chromatography (hexane/acetone 88/12) yielded the macrocyclic ester J73 as a sticky oil (8 mg, 15 μmol, 88% over 2 steps).

(3'R,7S,9R,11 S,Z')-11-hydroxy-9-methoxy-7-(3'-(2''-methoxyethoxymethoxymethyl)-1'-methylpent-1'-enyl)-12,12-dimethyl-6-oxabicyclo-[11.3.1]-heptadeca-1(17),13,15-trien-5-one Formula: $C_{30}H_{48}O_7$
Molar mass: 520.71
$R_f$: 0.39 (hexane/acetone 9/1)
HRMS: calculated ($M+NH_4^+$) 538.3738. found 538.3753.
$[\alpha]_D$: −72.7° (c=7.3 mg/ml)
$^1$H NMR (500 MHz, $CDCl_3$) δ 7.28-7.23 (m, 2H), 7.06-7.01 (m, 2H), 5.52 (dd, J=10.4, 1.3 Hz, 1H), 4.97 (dd, J=10.4, 1.4 Hz, 1H), 4.704 (d, J=6.9 Hz, 1H, A part of AB-spinsystem), 4.695 (d, J=6.9 Hz, 1H, B part of AB-spinsystem), 3.79-3.74 (m, 1H), 3.74-3.64 (m, 2H), 3.61-3.54 (m, 2H), 3.50 (dd, J=9.4, 5.0 Hz, 1H) 3.40 (s, 3H), 3.40-3.33 (m, 2H), 3.36 (dd, J=9.4, 6.7 Hz, 1H), 3.23 (s, 3H), 2.88 (ddd, J=13.5, 8.6, 4.7 Hz, 1H), 2.69-2.61 (m, 2H), 2.29-2.16 (m, 3H), 1.93 (ddd, J=17.6, 10.3, 2.9 Hz, 1H), 1.89-1.79 (m, 2H), 1.66-1.50 (m, 3H), 1.57 (d, J=1.5 Hz), 1.40 (s, 3H), 1.37 (s, 3H), 1.21-1.14 (m, 1H), 1.05 (ddd, J=14.8, 8.5, 2.4 Hz, 1H), 0.81 (app. t, J=7.5 Hz, 3H)
$^{13}$C NMR (125 MHz, $CDCl_3$) δ 171.70 (Cq), 145.84 (Cq), 139.91 (Cq), 135.04 (Cq), 129.67 (CH), 128.60 (CH), 127.90 (CH), 126.57 (CH), 124.84 (CH), 95.68 ($CH_2$), 77.03 (CH), 75.95 (CH), 72.00 ($CH_2$), 70.91 ($CH_2$), 68.37 (CH), 66.75 ($CH_2$), 59.15 ($CH_3$), 56.59 ($CH_3$), 42.38 (Cq), 39.36 (CH), 36.79 ($CH_2$), 35.55 ($CH_2$), 34.53 ($CH_2$), 31.49 ($CH_2$), 27.54 ($CH_3$), 25.16 ($CH_2$), 23.47 ($CH_3$), 23.22 ($CH_2$), 18.67 ($CH_3$), 11.84 ($CH_3$)

3.14 Synthesis of J74

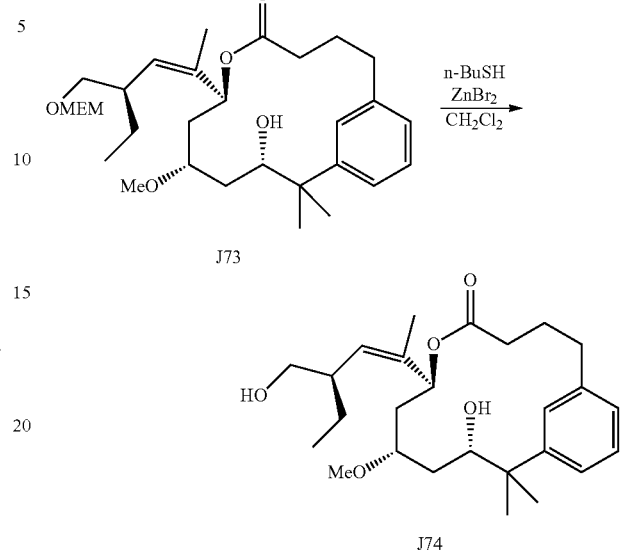

To a solution of the MEM-ether J73 (7 mg, 13 μmol, 1 eq.) in $CH_2Cl_2$ (540 μl) was added n-BuSH (2 μl, 20 μmol, 1.5 eq.) and $ZnBr_2$ (5 mg, 20 μmol, 1.5 eq.) at RT. The reaction was followed using tlc-analysis (hexane/acetone 8/2) and stirred for 25', after which the mixture was poured into a saturated aqueous $NaHCO_3$-solution (5 ml). The mixture was extracted with $CH_2Cl_2$ (4×5 ml), dried over $MgSO_4$ and concentrated. Flash column chromatography (hexane/acetone 8/2) delivered the macrocyclic diol J74 as a white solid (5.5 mg, 12.5 μmol, 96%).

Before submitting the sample to biological testing, it was extra purified using preparative HPLC (Luna C18 column, 50% MeCN to 100% MeCN in 30').

(3'R,7S,9R,11 S,Z')-11-hydroxy-9-methoxy-7-(3'-hydroxymethyl-1'-methylpent-1'-enyl)-12,12-dimethyl-6-oxabicyclo-[11.3.1]-heptadeca-1(17),13,15-trien-5-one Formula: $C_{26}H_{40}O_5$
Molar mass: 432.60
$R_f$: 0.19 (hexane/acetone 8/2)
HRMS: calculated ($M+H^+$) 433.2949. found 433.2958.
$[\alpha]_D$: −53.7° (c=5.6 mg/ml in $CHCl_3$)
$^1$H NMR (500 MHz, $CDCl_3$) δ 7.30-7.22 (m, 2H), 7.06-7.02 (m, 2H), 5.46 (dd, J=10.5, 1.2 Hz, 1H), 4.91 (dd, J=10.8, 1.5 Hz, 1H), 3.76 (dd, J=8.9, 2.4 Hz, 1H), 3.63 (dd, J=10.3, 4.1 Hz, 1H), 3.46-3.40 (m, 1H), 3.27 (s, 3H), 3.24 (app. t, J=10.1 Hz, 1H), 2.83 (ddd, J=13.7, 8.8, 4.6 Hz, 1H), 2.67-2.58 (m, 2H), 2.27 (ddd, J=17.2, 6.8, 3.4, 1H), 2.24-2.15 (m, 1H), 1.96 (ddd, J=17.2, 10.2, 3.3 Hz, 1H), 1.89 (ddd, J=15.1, 10.4, 2.7 Hz, 1H), 1.88-1.80 (m, 1H), 1.65 (ddd, J=15.1, 5.8, 1.5 Hz, 1H), 1.57 (d, J=1.4 Hz, 3H), 1.50 (ddd, J=14.8, 11.0, 2.4 Hz, 1H), 1.41 (s, 3H), 1.41-1.34 (m, 1H), 1.38 (s, 3H), 1.11-1.04 (m, 1H), 1.01 (ddd, J=14.9, 8.9, 2.4 Hz, 1H), 0.82 (app. t, J=7.4 Hz, 3H)
$^{13}$C NMR (125 MHz, $CDCl_3$) δ 173.27 (Cq), 145.74 (Cq), 139.84 (Cq), 136.10 (Cq), 131.24 (CH), 128.73 (CH), 128.10 (CH), 126.56 (CH), 124.79 (CH), 76.80 (CH), 75.80 (CH), 69.58 (CH), 66.85 ($CH_2$), 56.84 ($CH_3$), 42.71 (CH), 42.39 (Cq), 37.04 ($CH_2$), 35.34 ($CH_2$), 34.44 ($CH_2$), 31.55 ($CH_2$), 27.56 ($CH_3$), 24.80 ($CH_2$), 23.47 ($CH_2$), 23.07 ($CH_3$), 18.10 ($CH_3$), 12.05 ($CH_3$)

Example 4: Synthesis of Two $C_{13}$-Analogues: J45 and J51

4.1 Synthesis of TBS Ether J35

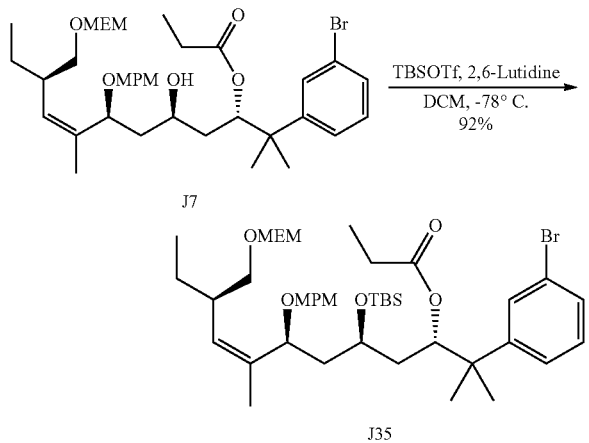

To a cooled (−78° C.) solution of alcohol J7 (1.31 g, 1.89 mmol, 1.00 equivalent) in 11.3 ml $CH_2Cl_2$ was added 2,6-lutidine (546 µl, 4.72 mmol, 2.50 equivalent), followed by TBSOTf (867 µl, 3.77 mmol, 2.00 equivalent). After stirring 3 h at −78° C., 14 ml sat. aq. $NaHCO_3$ was added and stirring was continued allowing the mixture to warm to room temperature. The combined organic phases of the extraction with $CH_2Cl_2$ (5×15 ml) were dried over $MgSO_4$ and concentrated. The orange oil (2.23 g) was then purified by flash chromatography (FC) ($SiO_2$, $CH_2Cl_2$/diethyl ether 97/3) to provide J35 (1.41 g, 92%) as a clear yellow oil.

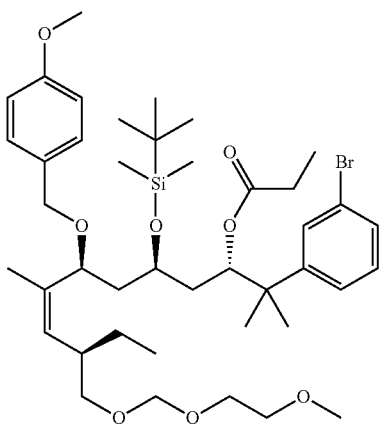

(3S,5R,7S,10R,Z)-2-(3'-bromophenyl)-5-(tert-butyldimethylsilyloxy)-7-(4'-methoxybenzyloxy)-10-(2'-methoxyethoxymethoxymethyl)-2,8-dimethyldodec-8-en-3-yl propionate Formula: $C_{42}H_{67}BrO_8Si$
Molar Mass: 807.97 g/mol
$R_f$: 0.32 (hexane/acetone 8/2)
ESI-MS: 824.3 $(M+NH_4^+)$ HR-MS: 824.4140 ($[M+NH_4]^+$, $C_{42}H_{71}NO_8Si^+$, calculated: 824.4127)

$[\alpha]_D$: −38.3 (c=0.83, $CHCl_3$)
$[\alpha]_{365}$: −111.5 (c=0.83, $CHCl_3$)

$^1$H NMR (CHLOROFORM-d, 700 MHz): δ=7.50 (app t, J=1.7 Hz, 1H), 7.30-7.34 (m, 2H), 7.17-7.20 (m, J=8.6 Hz, 2H), 7.16 (app t, J=7.9 Hz, 1H), 6.83-6.88 (m, 2H), 5.39 (d, J=9.7 Hz, 1H), 5.11 (d, J=9.5 Hz, 1H), 4.71 (d, J=6.9 Hz, 1H), 4.69 (d, J=6.7 Hz, 1H), 4.34 (d, J=11.6 Hz, 1H), 4.10 (dd, J=10.9, 1.8 Hz, 1H), 4.06 (d, J=11.4 Hz, 1H), 3.78-3.82 (m (containing a singlet, 3.81), 4H), 3.67-3.70 (m, 2H), 3.55-3.58 (m, 2H), 3.47 (dd, J=9.3, 5.8 Hz, 1H), 3.37-3.41 (m (containing a singlet, 3.39), 4H), 2.39-2.46 (m, 1H), 2.13-2.25 (m, 2H), 2.00 (ddd, J=14.0, 11.0, 3.0 Hz, 1H), 1.65 (d, J=1.1 Hz, 3H), 1.46-1.59 (m, 2H), 1.21-1.30 (m (containing two singlets, 1.28 and 1.27), 8H), 1.09-1.19 (m, 1H), 1.03 (app t, J=7.6 Hz, 3H), 0.89 (s, 9H), 0.76 (app t, J=7.4 Hz, 3H), 0.09 (s, 3H), 0.02 (s, 3H)

$^{13}$C NMR (CHLOROFORM-d, 176 MHz): δ=173.8 (C), 158.8 (C), 149.0 (C), 136.3 (C), 131.3 (C), 130.7 (CH), 129.8 (CH), 129.6 (CH), 129.2 (CH), 128.5 (2CH), 125.4 (CH), 122.4 (C), 113.6 (2CH), 95.5 ($CH_2$), 76.8 (CH), 73.6 (CH), 71.8 ($CH_2$), 71.4 ($CH_2$), 69.4 ($CH_2$), 66.9 (CH), 66.7 ($CH_2$), 59.0 ($CH_3$), 55.3 ($CH_3$), 42.7 (C), 42.2 ($CH_2$), 39.2 (CH), 38.1 ($CH_2$), 27.7 ($CH_2$), 26.0 (3$CH_3$), 25.9 ($CH_3$), 25.0 ($CH_2$), 23.4 ($CH_3$), 18.0 (C), 17.9 ($CH_3$), 11.8 ($CH_3$), 9.3 ($CH_3$), −3.8 ($CH_3$), −4.8 ($CH_3$)

4.2 Synthesis of Stannane J36

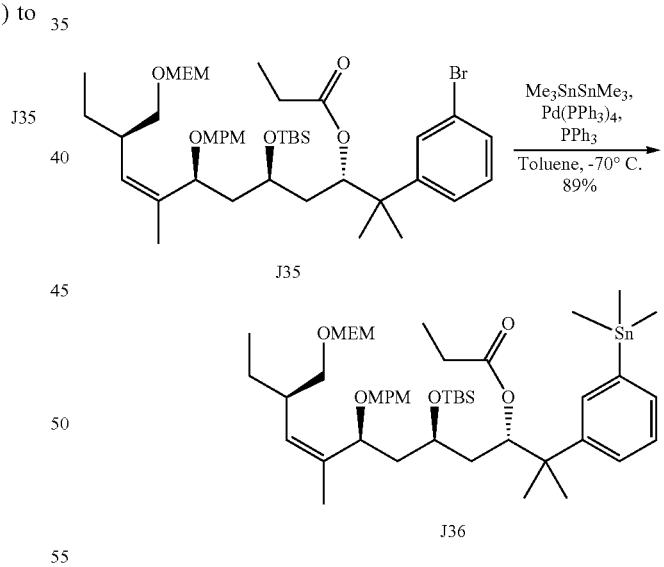

To a solution of J35 (1.39 g, 1.72 mmol, 1.00 equivalent) and $PPh_3$ (180 mg, 0.68 mmol, 0.40 equivalent) in 17.2 ml toluene was added $Me_3SnSnMe_3$ (713 µl, 3.44 mmol, 2.00 equivalent). $Pd(PPh_3)_4$ (200 mg, 0.17 mmol, 0.10 equivalent) was added and the yellow solution was heated at 70° C. After stirring for 48 h at 70° C., the reaction mixture was poured in 31 ml sat. aq. $NaHCO_3$ and 31 ml water, extracted with $CH_2Cl_2$ (3×62 ml), dried over $MgSO_4$ and concentrated. The residue (2.62 g, yellow oil with an orange solid) was purified by FC ($SiO_2$, pentane/diethyl ether 8/2) to provide J36 (1.37 g, 89%) as a pale oil.

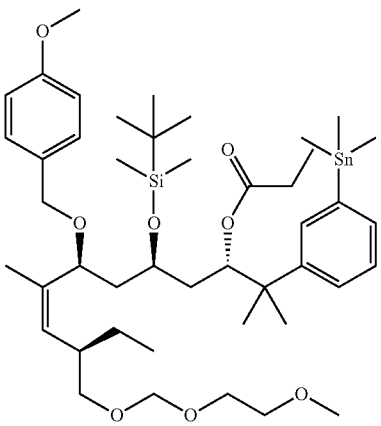

(3S,5R,7S,10R,Z)-5-(tert-butyldimethylsilyloxy)-7-(4'-methoxybenzyloxy)-10-(2'-methoxy-ethoxymethoxymethyl)-2,8-dimethyl-2-(3'-trimethyl-stannylphenyl)dodec-8-en-3-yl propionate Formula: C$_{45}$H$_{76}$O$_8$SiSn
Molar Mass: 891.88 g/mol R$_f$: 0.28 (pentane/diethyl ether 8/2)
ESI-MS: 910.5 [M+NH$_4$]$^+$
HR-MS: 910.4696 ([M+NH$_4$]$^+$, C$_{45}$H$_{80}$NO$_8$SiSn$^+$, calculated: 910.4670)
[α]$_D$: −32.5 (c=1.04, CHCl$_3$)
[α]$_{365}$: −91.4 (c=1.04, CHCl$_3$)
$^1$H NMR (CHLOROFORM-d, 500 MHz): δ=7.40-7.53 (m, 1H), 7.24-7.36 (m, 3H), 7.16-7.22 (m, 2H), 6.81-6.88 (m, 2H), 5.43 (d, J=9.8 Hz, 1H), 5.11 (d, J=9.5 Hz, 1H), 4.71 (d, J=6.9 Hz, 1H), 4.69 (d, J=6.9 Hz, 1H), 4.34 (d, J=11.4 Hz, 1H), 4.12 (dd, J=10.4, 1.8 Hz, 1H), 4.07 (d, J=11.6 Hz, 1H), 3.78-3.85 (m (containing a singlet, 3.81), 4H), 3.66-3.70 (m, 2H), 3.52-3.58 (m, 2H), 3.47 (dd, J=9.8, 6.0 Hz, 1H), 3.35-3.42 (m (containing a singlet, 3.39), 4H), 2.40-2.49 (m, 1H), 2.11-2.18 (m, 2H), 2.00 (ddd, J=14.0, 11.1, 3.2 Hz, 1H), 1.65 (d, J=1.1 Hz, 3H), 1.57-1.62 (m, 1H), 1.43-1.53 (m, 1H), 1.20-1.39 (m (containing two singlets, 1.31 and 1.30, 8H), 1.08-1.19 (m, 1H), 0.98 (app t, J=7.6 Hz, 3H), 0.88 (s, 9H), 0.75 (app t, J=7.4 Hz, 3H), 0.28 (s, 9H), 0.08 (s, 3H), 0.01 (s, 3H)

$^{13}$C NMR (CHLOROFORM-d, 126 MHz): δ=173.7 (C), 158.8 (C), 145.8 (C), 141.6 (C), 136.4 (C), 133.5 (2CH), 131.3 (C), 130.6 (CH), 128.5 (2CH), 127.6 (CH), 126.7 (CH), 113.6 (2CH), 95.5 (CH2), 77.2 (CH), 73.7 (CH), 71.8 (CH2), 71.4 (CH2), 69.4 (CH2), 67.1 (CH), 66.7 (CH2), 59.0 (CH3), 55.2 (CH3), 42.7 (CH2), 42.1 (C), 39.2 (CH), 38.1 (CH2), 27.7 (CH2), 26.1 (3CH3), 25.6 (CH3), 25.0 (CH2), 23.7 (CH3), 18.0 (C), 17.9 (CH3), 11.8 (CH3), 9.3 (CH3), −3.8 (CH3), −4.8 (CH3), −9.6 (3CH3)

4.3 Synthesis of Ester J37

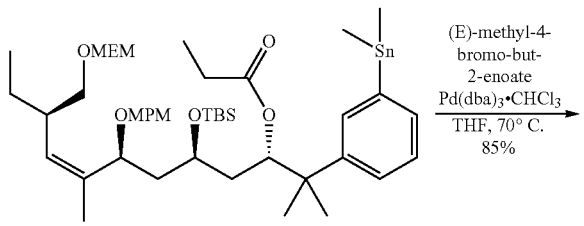

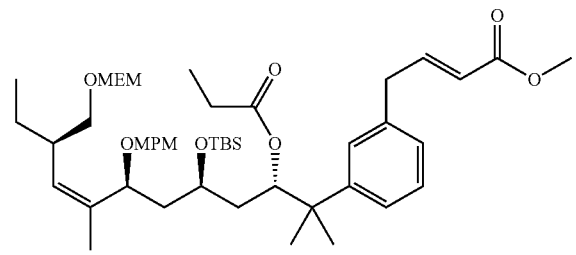

To a solution of J36 (1.34 g, 1.50 mmol, 1.00 equivalent) and (E)-methyl-4-bromo-but-2-enoate (360 μl, 3.01 mmol, 2.00 equivalent) in 7.52 ml THF was added Pd(dba)$_3$.CHCl$_3$ (23.3 mg, 0.02 mmol, 0.015 equivalent). The red solution was heated at 70° C. to become a clear yellow solution. After stirring for 5 h at 70° C., the reaction mixture was poured in 36 ml sat. aq. NaHCO$_3$, extracted with CH$_2$Cl$_2$ (3×36 ml), dried over MgSO$_4$ and concentrated. The yellow oil (2.62 g) was purified by FC (SiO$_2$, pentane/diethyl ether 6/4) to afford J37 (1.06 g, 89%) as a pale yellow oil.

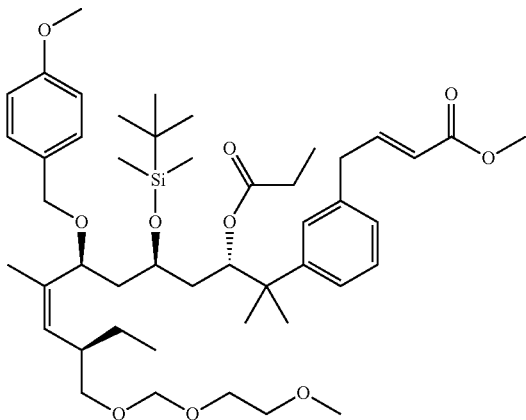

(3"S,5"R,7"S,10"R,Z)-methyl 4-(3'-(5"-(tert-butyldimethylsilyloxy)-7"-(4'''-methoxybenzyloxy)-10"-(2'''-methoxyethoxymethoxymethyl)-2",8"-dimethyl-3"-(propionyloxy)dodec-8"-en-2"-yl)phenyl)but-2-enoate Formula: $C_{47}H_{74}O_{10}Si$
Molar Mass: 827.17 g/mol $R_f$: 0.25 (pentane/diethyl ether 6/4)
ESI-MS: 844.4 [M+NH$_4$]$^+$
HR-MS: 844.5398 ([M+NH$_4$]$^+$, $C_{47}H_{78}NO_{10}Si^+$, calculated: 844.5390), 849.4953 ([M+Na]$^+$, $C_{47}H_{74}NaO_{10}Si^+$, calculated: 849.4944)
[α]$_D$: −35.8 (c=0.70, CHCl$_3$)
[α]$_{365}$: −101.2 (c=0.70, CHCl$_3$)

$^1$H NMR (CHLOROFORM-d, 300 MHz): δ=7.15-7.26 (m, 5H), 7.09 (dt, J=15.4, 7.0 Hz, 1H), 6.96-7.02 (m, 1H), 6.81-6.91 (m, 2H), 5.82 (dt, J=15.5, 1.6 Hz, 1H), 5.44 (d, J=9.6 Hz, 1H), 5.10 (dd, J=10.2, 0.9 Hz, 1H), 4.67-4.73 (m, 2H), 4.34 (d, J=11.5 Hz, 1H), 4.11 (dd, J=10.5, 1.5 Hz, 1H), 4.07 (d, J=11.5 Hz, 1H), 3.79-3.83 (m (containing a singlet), 3.81, 4H), 3.71 (s, 3H), 3.65-3.70 (m, 2H), 3.53-3.59 (m, 2H), 3.35-3.52 (m (containing a singlet, 3.39), 7H), 2.38-2.50 (m, 1H), 2.12-2.22 (m, 2H), 1.99 (ddd, J=13.9, 11.1, 3.0 Hz, 1H), 1.65 (d, J=1.1 Hz, 3H), 1.42-1.59 (m, 2H), 1.17-1.34 (m (containing two singlets, 1.29 and 1.27), 8H), 1.08-1.17 (m, 1H), 1.01 (app t, J=7.6 Hz, 3H), 0.88 (s, 9H), 0.76 (app t, J=7.4 Hz, 3H), 0.08 (s, 3H), 0.01 (s, 3H)

$^{13}$C NMR (CHLOROFORM-d, 75 MHz): δ=173.8 (C), 167.6 (C), 147.7 (CH), 147.1 (C), 137.2 (C), 136.4 (C), 131.3 (C), 130.6 (CH), 128.5 (2CH), 128.3 (CH), 127.0 (CH), 126.4 (CH), 125.0 (CH), 121.8 (CH), 121.7 (C), 113.6 (2CH), 95.5 (CH$_2$), 77.1 (CH), 73.6 (CH), 71.8 (CH$_2$), 71.4 (CH$_2$), 69.4 (CH$_2$), 66.9 (CH), 66.7 (CH$_2$), 59.0 (CH$_3$), 55.2 (CH$_3$), 51.4 (CH$_3$), 42.7 (C), 42.0 (CH$_2$), 39.2 (CH), 38.7 (CH$_2$), 38.0 (CH$_2$), 27.7 (CH$_2$), 26.0 (4CH$_3$), 25.0 (CH$_2$), 23.2 (CH$_3$), 18.0 (C), 17.9 (CH$_3$), 11.8 (CH$_3$), 9.3 (CH$_3$)-3.8 (CH$_3$), −4.9 (CH$_3$)

4.4 Synthesis of Diol J38

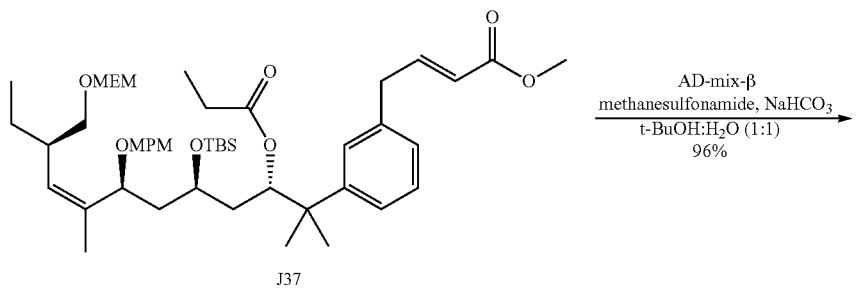

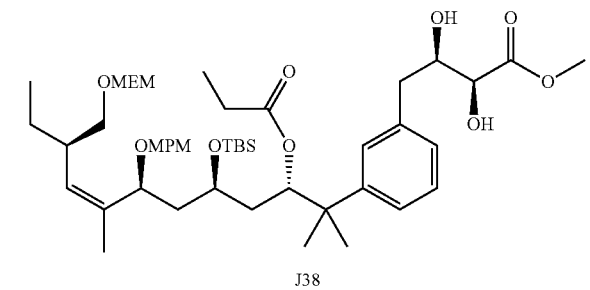

A solution of AD-mix-β 4.44 g), methanesulfonamide (235 mg, 2.47 mmol, 2.00 equivalent) and NaHCO$_3$ (995 mg, 11.8 mmol, 9.60 equivalent) in 1.33 ml t-BuOH and 12.3 ml H$_2$O was stirred for 10 min. A solution of J37 in 5 ml t-BuOH was added dropwise and the flask was rinsed with t-BuOH (3×2 ml). The greenish reaction mixture was vigorously stirred at room temperature for 41 h. 43 ml sat.

aq. NaS$_2$O$_3$ and 20 ml water was added and stirred for 1 h to become a clear solution followed by extracting with CH$_2$Cl$_2$ (5×250 ml), drying over MgSO$_4$ and concentrating. The residue (pale oil with white solid) was purified by FC (SiO$_2$, pentane/acetone 75/25) to afford J38 (1.02 g, 96%) as a pale oil.

J38

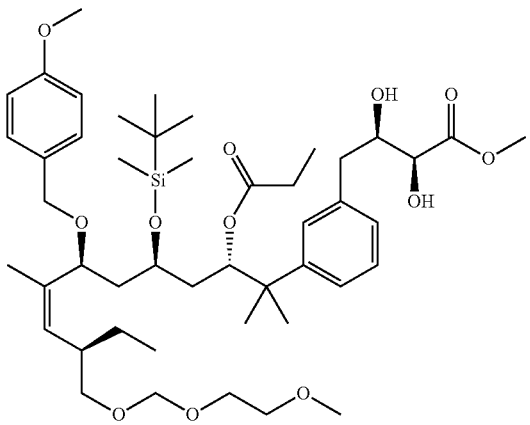

(2S,3R,3"S,5"R,7"S,10"R,Z)-methyl-4-(3'-(5"-(tert-butyldimethylsilyloxy)-7"-(4'''-methoxybenzyloxy)-10"-(2'''-methoxyethoxymethoxymethyl)-2",8"-dimethyl-3"-(propionyloxy)dodec-8"-en-2"-yl)phenyl)-2,3-dihydroxybutanoate Formula: C$_{47}$H$_{76}$O$_{12}$Si
Molar Mass: 861.18 g/mol
R$_f$: 0.28 (pentane/acetone 75/25)
ESI-MS: 878.4 [M+NH$_4$]$^+$
HR-MS: 878.5453 ([M+NH$_4$]$^+$, C$_{47}$H$_{80}$NO$_{12}$Si$^+$, calculated: 878.5444), 883.5004 ([M+Na]$^+$, C$_{47}$H$_{76}$NaO$_{12}$Si$^+$, calculated: 884.4998)

[α]$_D$: −17.7 (c=0.90, CHCl$_3$)
[α]$_{365}$: −36.5 (c=0.90, CHCl$_3$)

$^1$H NMR (CHLOROFORM-d, 500 MHz): δ=7.26-7.28 (m, 1H), 7.21-7.24 (m, 2H), 7.16-7.20 (m, 2H), 7.04-7.12 (m, 1H), 6.82-6.87 (m, 2H), 5.41 (d, J=9.8 Hz, 1H), 5.11 (d, J=10.1 Hz, 1H), 4.71 (d, J=6.7 Hz, 1H), 4.69 (d, J=6.7 Hz, 1H), 4.34 (d, J=11.4 Hz, 1H), 4.09-4.17 (m, 3H), 4.07 (d, J=11.6 Hz, 1H), 3.77-3.83 (m (containing two singlets, 3.81 and 3.80), 7H), 3.67-3.70 (m, 2H), 3.54-3.58 (m, 2H), 3.45-3.50 (m, 1H), 3.34-3.44 (m (containing a singlet, 3.39), 4H), 2.86-2.98 (m, 2H), 2.41-2.51 (m, 1H), 1.95-2.10 (m, 3H), 1.66 (d, J=0.9 Hz, 3H), 1.56-1.64 (m, 1H), 1.46-1.55 (s, 1H), 1.38-1.45 (m, 1H), 1.20-1.37 (m (containing two singlets, 1.30 and 1.29), 7H), 1.10-1.19 (m, 1H), 0.83-0.96 (m, 12H), 0.79 (app. t, J=7.3 Hz, 3H), 0.08 (s, 3H), 0.03 (s, 3H)

$^{13}$C NMR (CHLOROFORM-d, 126 MHz): δ=173.8 (2C), 158.8 (C), 146.9 (C), 137.1 (C), 136.4 (C), 131.2 (C), 130.6 (CH), 128.5 (2CH), 128.3 (CH), 128.2 (CH), 126.9 (CH), 124.9 (CH), 113.6 (2CH), 95.5 (CH$_2$), 77.4 (CH), 73.6 (CH), 73.4 (CH), 72.6 (CH), 71.8 (CH$_2$), 71.4 (CH$_2$), 69.4 (CH$_2$), 67.0 (CH), 66.7 (CH$_2$), 59.0 (CH$_3$), 55.3 (CH$_3$), 52.6 (CH$_3$), 42.7 (CH$_2$), 41.9 (C), 40.5 (CH$_2$), 39.2 (CH), 37.9 (CH$_2$), 27.6 (CH$_2$), 26.0 (3CH$_3$), 25.0 (CH$_2$), 24.4 (CH$_3$), 24.3 (CH$_3$), 18.0 (C), 17.9 (CH$_3$), 11.8 (CH$_3$), 9.2 (CH$_3$), −3.8 (CH$_3$), −4.9 (CH$_3$)

4.5 Synthesis of MOM Ether J39

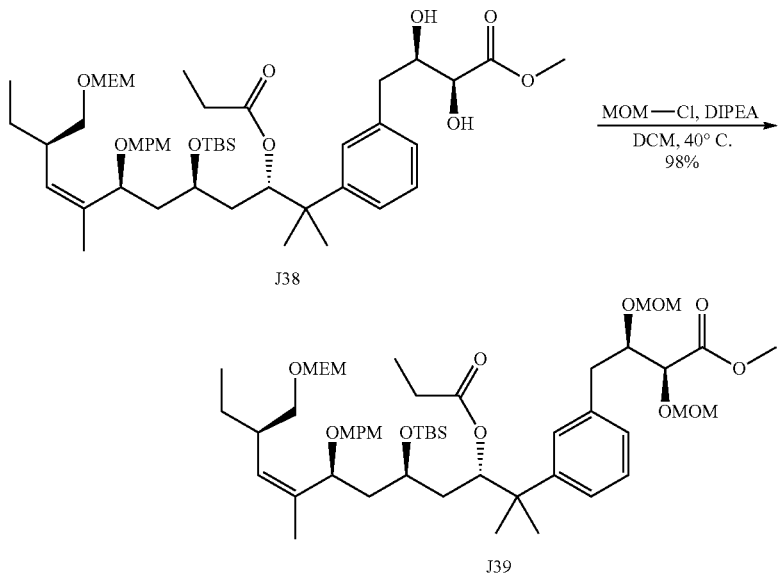

To a solution of diol J38 (955 mg, 1.11 mmol, 1.00 equivalent) in 5.5 ml CH$_2$Cl$_2$ was added DIPEA (1.06 ml, 6.10 mmol, 5.50 equivalent), followed by adding freshly prepared MOM-Cl (2.252M CH$_2$Cl$_2$ and methyl acetate, 2.46 ml, 5.54 mmol, 5.00 equivalent) at 0° C. After stirring 17 h at 40° C., 14 ml water was added and the mixture was extracted with diethyl ether (3×10 ml). The combined organic phases were dried over MgSO$_4$ and concentrated. The orange oil (1.25 g) was then purified by FC (SiO$_2$, hexane/ethyl acetate 55/45) to provide J39 (1.03 g, 98%) as a clear oil.

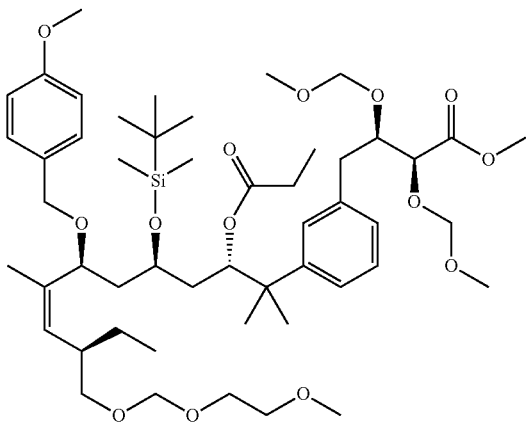

(2S,3R,3"S,5"R,7"SI,10"R,Z)-)-methyl-4-(3'-(5"-tert-butyldimethylsilyloxy)-7"-(4'''-methoxybenzyloxy)-10"-(2'''-methoxyethoxymethoxy)ethyl)-2",8"-dimethyl-3"-(propionyloxydodec-8"-en-2"-yl)phenyl)-2,3-bis(methoxymethoxy)butanoate Formula: $C_{51}H_{84}O_{14}Si$
Molar Mass: 949.29 g/mol $R_f$: 0.19 (hexane/acetone 8/2)
ESI-MS: 966.5 $[M+NH_4^+]$
HR-MS: 966.5999 ($[M+NH_4]^+$, $C_{51}H_{88}NO_{14}Si^+$, calculated: 966.5981), 971.5533 ($[M+Na]^+$, $C_{51}H_{84}NaO_{14}Si^+$, calculated: 971.5523)
$[\alpha]_D$: −36.7 (c=0.90, $CHCl_3$)
$[\alpha]_{365}$: −91.0 (c=0.90, $CHCl_3$)
1H NMR (CHLOROFORM-d, 500 MHz): δ=7.21-7.26 (m, 3H), 7.17-7.21 (m, 2H), 7.09 (app. dt, J=7.2, 1.4 Hz, 1H), 6.83-6.87 (m, 2H), 5.45 (d, J=9.9 Hz, 1H), 5.11 (d, J=9.6 Hz, 1H), 4.77 (d, J=7.0 Hz, 1H), 4.65-4.74 (m, 3H), 4.51 (d, J=7.2 Hz, 1H), 4.39 (d, J=7.2 Hz, 1H), 4.34 (d, J=11.4 Hz, 1H), 4.21 (ddd, J=7.8, 6.4, 2.9 Hz, 1H), 4.16 (d, J=3.1 Hz, 1H), 4.11 (dd, J=10.5, 1.8 Hz, 1H), 4.07 (d, J=11.4 Hz, 1H), 3.77-3.84 (m (containing a singlet, 3.81), 4H), 3.75 (s, 3H), 3.67-3.70 (m, 2H), 3.54-3.57 (m, 2H), 3.44-3.49 (m (containing a singlet, 3.46), 4H), 3.36-3.42 (m (containing a singlet, 3.39), 4H), 3.14 (s, 3H), 2.98 (dd, J=13.7, 7.8 Hz, 1H), 2.93 (dd, J=13.7, 6.3 Hz, 1H), 2.41-2.50 (m, 1H), 2.11-2.22 (m, 2H), 1.99 (ddd, J=13.9, 10.8, 2.9 Hz, 1H), 1.65 (d, J=1.2 Hz, 3H), 1.54-1.61 (m, 1H), 1.46-1.52 (m, 1H), 1.18-1.32 (m (containing two singlets, 1.29 and 1.26), 8H), 1.09-1.18 (m, 1H), 1.00 (app. t, J=7.6 Hz, 3H), 0.88 (s, 9H), 0.77 (app. t, J=7.4 Hz, 3H), 0.09 (s, 3H), 0.01 ppm (s, 3H)
13C NMR (CHLOROFORM-d, 126 MHz): δ=173.8 (C), 171.1 (C), 158.8 (C), 146.8 (C), 137.3 (C), 136.3 (C), 131.3 (C), 130.6 (CH), 128.5 (2CH), 128.2 (CH), 127.7 (CH), 127.0 (CH), 125.0 (CH), 113.6 (2CH), 97.0 ($CH_2$), 96.6 ($CH_2$), 95.5 ($CH_2$), 79.3 (CH), 77.1 (CH), 77.1 (CH), 73.7 (CH), 71.8 ($CH_2$), 71.3 ($CH_2$), 69.4 ($CH_2$), 66.9 (CH), 66.7 ($CH_2$), 59.0 ($CH_3$), 56.5 ($CH_3$), 55.7 ($CH_3$), 55.2 ($CH_3$), 51.9 ($CH_3$), 42.8 ($CH_2$), 42.0 (C), 39.2 (CH), 38.0 ($CH_2$), 37.9 ($CH_2$), 27.7 ($CH_2$), 26.2 ($CH_3$), 26.0 (3$CH_3$), 25.0 ($CH_2$), 23.1 ($CH_3$), 18.0 (C), 17.9 ($CH_3$), 11.8 ($CH_3$), 9.3 ($CH_3$), −3.8 ($CH_3$), −4.8 ($CH_3$)

4.6 Synthesis of Alcohol J40

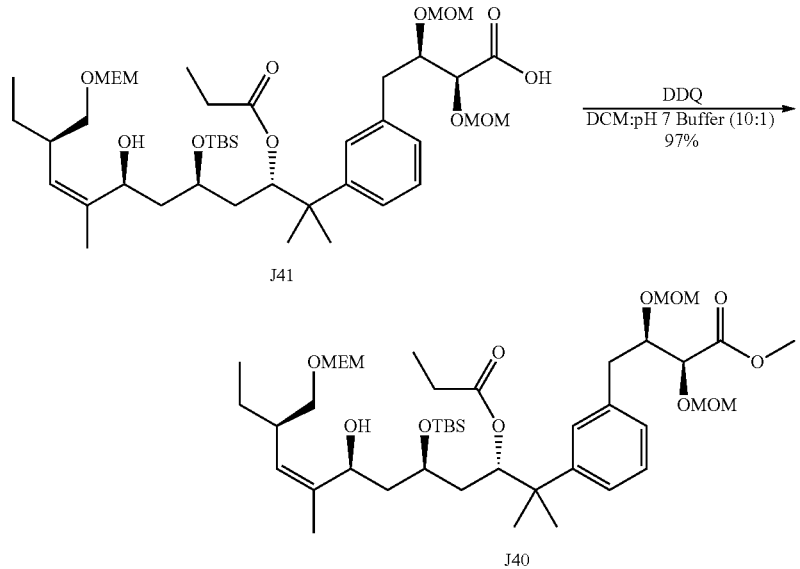

To a stirring solution of J39 (522 mg, 0.55 mmol, 1.00 equivalent) in 22 ml $CH_2Cl_2$ and 2.2 ml pH 7 buffer was added 2,3-dichloro-5,6-dicyano-1,4-benzoquinone (500 mg, 2.20 mmol, 4.00 equivalent) in four portions over 90 min. After stirring the black/brownish/greenish mixture for an extra 30 min, 20 ml sat. aq. $NaHCO_3$ was added. The mixture was extracted with $CH_2Cl_2$ (5×50 ml), dried over $MgSO_4$ and concentrated. The residue was then purified by FC ($SiO_2$, $CH_2Cl_2$/diethyl ether 97/3) to provide J40 (1.41 g, 97%) as a pale oil.

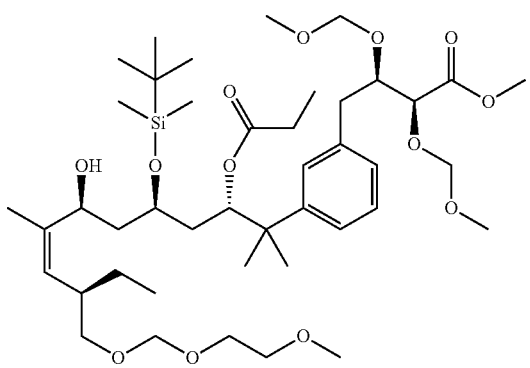

(2S,3R,3"S,5"R,7"S,10"R,Z)-methyl 4-(3"-(5-tert-butyldimethylsilyloxy)-7"-hydroxy-10"-(2"'-methoxyethoxymethoxymethyl)-2",8"-dimethyl-3"-(propionyloxy)dodec-8"-en-2"-yl)phenyl)-2,3-bis(methoxymethoxy)butanoate Formula: $C_{43}H_{76}O_{13}Si$ Molar Mass: 829.14 g/mol $R_f$: 0.18 (hexane/ethyl acetate 1/1)

IR: 2955, 2885, 1739, 1595, 1466, 1363, 1253, 1201, 1181, 1153, 1100, 1049, 913, 840, 776, 734

ESI-MS: 846.4 [M+NH$_4^+$]

HR-MS: 846.5379 ([M+NH$_4$]$^+$, $C_{43}H_{80}NO_{13}Si^+$, calculated: 966.5393), 851.4960 ([M+Na]$^+$, $C_{43}H_{76}NaO_{13}Si^+$, calculated: 851.4947)

[α]$_D$: −21.2 (c=0.68, CHCl$_3$)

[α]$_{365}$: −40.8 (c=0.68, CHCl$_3$)

$^1$H NMR (CHLOROFORM-d, 500 MHz): δ=7.20-7.26 (m, 3H), 7.10 (app. dt, J=7.2, 1.7 Hz, 1H), 5.38 (d, J=8.9 Hz, 1H), 4.93 (d, J=9.2 Hz, 1H), 4.77 (d, J=7.0 Hz, 1H), 4.72 (d, J=7.0 Hz, 1H), 4.69 (d, J=6.9 Hz, 1H), 4.67 (d, J=6.7 Hz, 1H), 4.51 (d, J=7.2 Hz, 1H), 4.44 (dd, J=9.6, 2.6 Hz, 1H), 4.40 (d, J=7.0 Hz, 1H), 4.22 (ddd, J=7.8, 6.4, 2.9 Hz, 1H), 4.16 (d, J=2.9 Hz, 1H), 3.76 (s, 3H), 3.68-3.74 (m, 1H), 3.62-3.66 (m, 2H), 3.50-3.57 (m, 3H), 3.47 (s, 3H), 3.39 (s, 3H), 3.27 (app. t, J=8.9 Hz, 1H), 3.16 (s, 3H), 2.99 (dd, J=13.7, 7.8 Hz, 1H), 2.94 (dd, J=13.6, 6.3 Hz, 1H), 2.70 (br. s, 1H), 2.50-2.61 (m, 1H), 2.25-2.31 (m, 2H), 1.76 (ddd, J=14.2, 9.3, 4.9 Hz, 1H), 1.67 (d, J=1.2 Hz, 3H), 1.56 (ddd, J=13.9, 9.6, 3.8 Hz, 1H), 1.36-1.51 (m, 3H), 1.31 (s, 3H), 1.27 (s, 3H), 1.16-1.24 (m, 1H), 1.10 (app. t, J=7.6 Hz, 3H), 0.82-0.88 (m (containing a singlet, 0.86), 12H), 0.02 (s, 3H), −0.01 (s, 3H)

$^{13}$C NMR (CHLOROFORM-d, 126 MHz): δ=173.9 (C), 171.1 (C), 146.7 (C), 139.6 (C), 137.4 (C), 129.9 (CH), 128.2 (CH), 127.7 (CH), 127.1 (CH), 125.0 (CH), 97.0 (CH$_2$), 96.6 (CH$_2$), 95.3 (CH$_2$), 79.4 (CH), 77.2 (CH), 77.1 (CH), 71.7 (CH$_2$), 71.0 (CH$_2$), 68.7 (CH), 66.8 (CH$_2$), 66.0 (CH), 59.0 (CH$_3$), 56.5 (CH$_3$), 55.8 (CH$_3$), 51.9 (CH$_3$), 42.2 (CH$_2$), 42.0 (C), 39.1 (CH), 38.6 (CH$_2$), 37.9 (CH$_2$), 27.9 (CH$_2$), 26.2 (CH$_3$), 25.9 (3CH$_3$), 24.2 (CH$_2$), 22.9 (CH$_3$), 18.3 (CH$_3$), 17.9 (C), 11.7 (CH$_3$), 9.3 (CH$_3$), −4.3 (CH$_3$), −4.7 (CH$_3$)

4.7 Synthesis of Carboxylic Acid J41

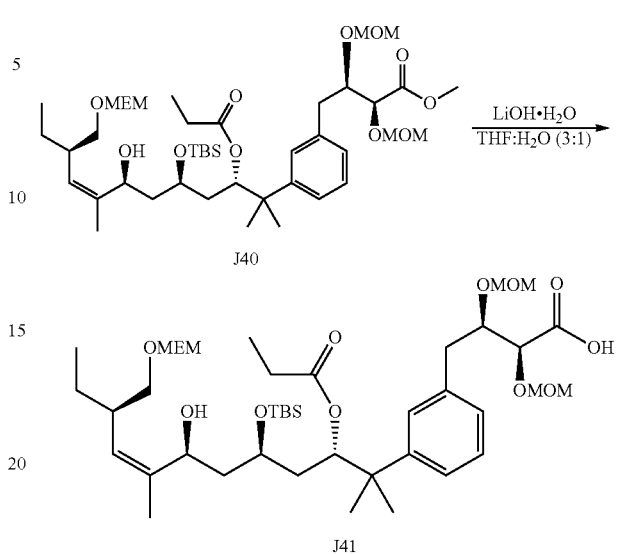

To a cooled (0° C.) solution of J40 (208 mg, 0.25 mmol, 1.00 equivalent) in 5.6 ml THF and 1.9 ml water was added LiOH.H$_2$O (105 mg, 2.51 mmol, 10.0 equivalent) in one portion. After stirring 23 h at room temperature, the mixture was poured in 15 ml sat. aq. NH$_4$Cl, extracted with ethyl acetate (5×15 ml), dried over MgSO$_4$ and concentrated. The residue was dissolved in 10 ml toluene and concentrated to afford crude J41 (217 mg) as a yellow, viscous oil. The carboxylic acid was used without further purification.

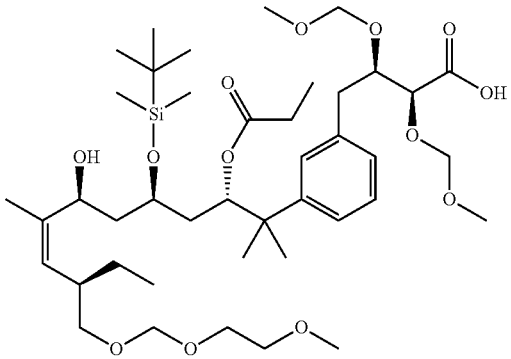

(2S,3R,3'S,5"R,7"S,10"R,Z)-4-(3'-(5"-(tert-butyldimethylsilyloxy)-7"-hydroxy-10"-(2-methoxyethoxymethoxymethyl)-2",8"-dimethyl-3"-(propionyloxy)dodec-8"-en-2"-yl)phenyl)-2,3-bis(methoxymethoxy)butanoic acid Formula: $C_{42}H_{74}O_{13}Si$ Molar Mass: 815.11 g/mol $R_f$: 0.27 (pentane/acetone/acetic acid 69.5/30/0.5)

ESI-MS: 832.4 [M+NH$_4^+$]

HR-MS: 832.5239 ([M+NH$_4$]$^+$, $C_{42}H_{78}NO_{13}Si^+$, calculated: 832.5237), 837.4793 ([M+Na]$^+$, $C_{42}H_{74}NaO_{13}Si^+$, calculated: 837.4791)

4.8 Synthesis of Alcohol J42

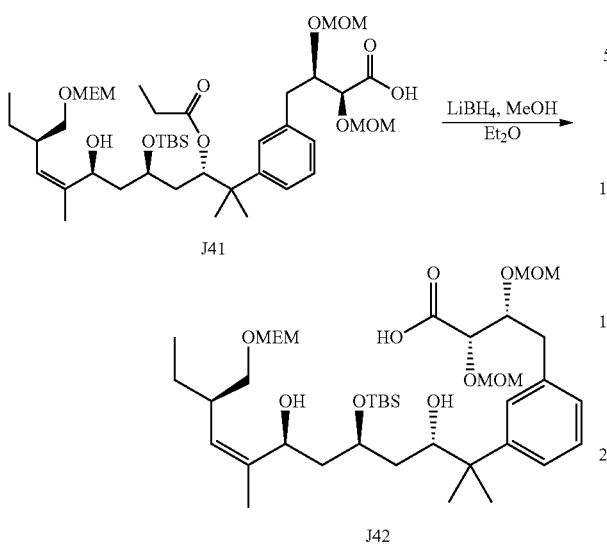

To a cooled (0° C.) solution of crude J41 (217 mg, 0.25 mmol, 1.00 equivalent) in 5 ml diethyl ether and methanol (40.6 µl, 1.00 mmol, 4 equivalent) was added LiBH$_4$ (2M in THF, 502 µl, 1.00 mmol, 4.00 equivalent). After stirring for 15 min, the mixture was allowed to warm to room temperature and stirring was continued for 26 h (LC-MS analysis showed a 70% conversion) before an extra portion of LiBH$_4$ (2M in THF, 251 µl, 0.50 mmol, 2.00 equivalent) was added. After stirring an extra 19 h, the mixture was cooled (0° C.), diluted with 10 ml ethyl acetate and quenched with 125 ml sat. aq. NH$_4$Cl. The mixture was extracted with ethyl acetate (5×125 ml), dried over MgSO$_4$ and concentrated. The residue was dissolved in 1.5 ml toluene and concentrated to afford crude J42 (255 mg) as a yellow, viscous oil. The seco-acid was used without further purification (LC-MS analysis showed a 96.5% conversion of the starting material).

J42

(2S,3R,3"S,5"R,7"S,10"R,Z)-4-(3'-(5"-(tert-butyldimethylsilyloxy)-3",7"-dihydroxy-10"-(2'"-methoxyethoxymethoxymethyl)-2",8"-dimethyldodec-8"-en-2"-yl)phenyl)-2,3-bis(methoxymethoxy) butanoic acid Formula: C$_{39}$H$_{70}$O$_{12}$Si
Molar Mass: 759.05 g/mol R$_f$: 0.21 (pentane/acetone/acetic acid 69.5/30/0.5)
ESI-MS: 757.3 [M−H$^+$]
HR-MS: 757.4557 ([M−H$^+$], C$_{39}$H$_{69}$O$_{13}$Si$^+$, calculated: 757.4564)

4.9 Synthesis of Lactone J43

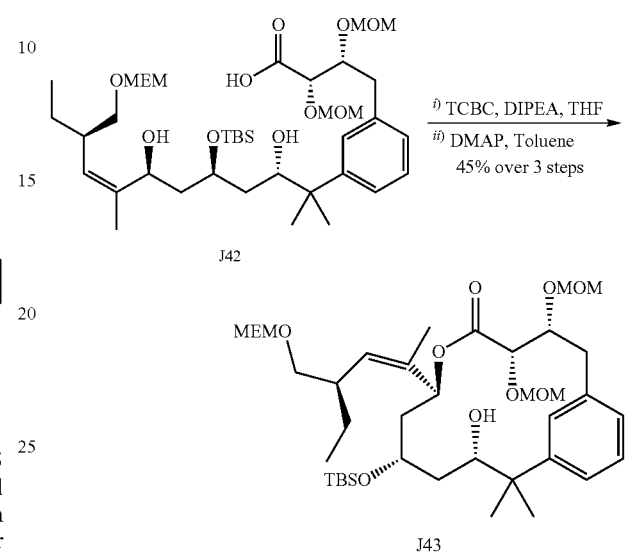

To a cooled (0° C.) solution of crude J42 (255 mg, 0.25 mmol, 1.00 equivalent) in 9.5 ml THF was dropwise added DIPEA (328 µl, 1.88 mmol, 7.50 equivalent) and 2,4,6-trichlorobenzoyl chloride (198 µl, 1.26 mmol, 5.00 equivalent). The yellow mixture was stirred for 4 h at room temperature and THF was removed in vacuo. The residue was dissolved in 50 ml toluene and added to a solution of DMAP (766 mg, 6.27 mmol, 25 equivalent) in 326 ml toluene at room temperature over a period of 14 h via syringe pump. After further stirring for 31 h, the mixture was poured in 300 ml sat. aq. NaHCO$_3$, separated and extracted with ethyl acetate (4×300 ml). The combined organic phases were dried over MgSO$_4$ and concentrated in vacuo. The residue (yellow oil with white crystals) was then purified by FC (SiO$_2$, hexane/ethyl acetate 6/4) to provide J43 (83.5 mg, 45% over three steps) as a pale yellow oil.

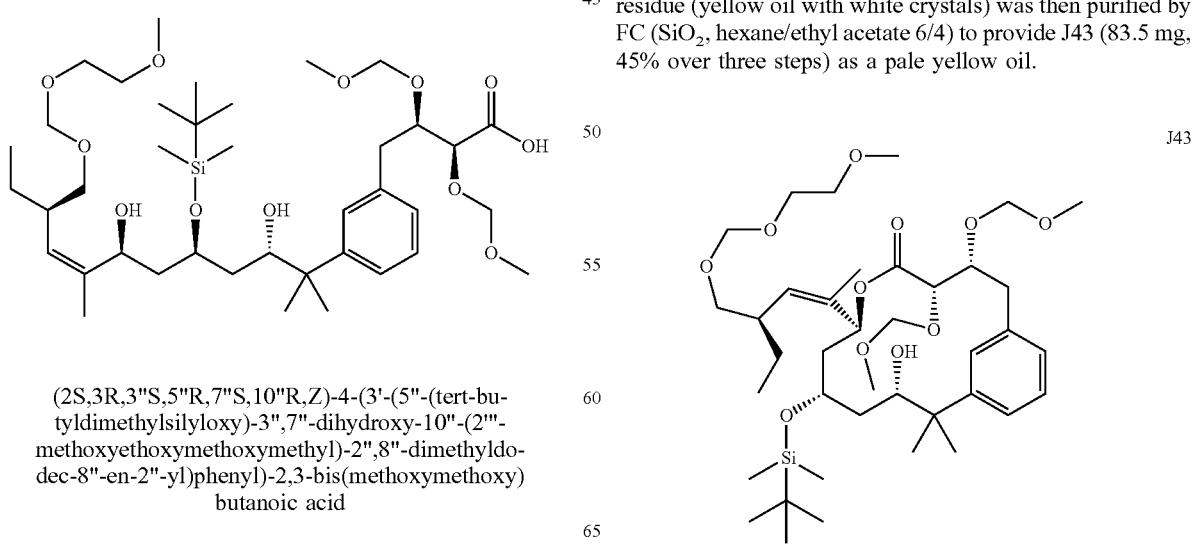

(3R,3'R,4S,7S,9R,11 S,Z)-9-(tert-butyldimethylsilyloxy)-11-hydroxy-7-(3'-(2''-methoxyethoxymethoxymethyl)-1'-methylpent-1'-enyl)-2,3-bis(methoxymethoxy)-12,12-dimethyl-6-oxabicyclo[11.3.1]heptadeca-1(17),13,15-trien-5-one Formula: C$_{39}$H$_{68}$O$_{11}$Si
Molar Mass: 741.04 g/mol
R$_f$: 0.20 (hexane/ethyl acetate 6/4)
IR: 3008, 2951, 2930, 2894, 1749, 1468, 1442, 1364, 1254, 1217, 1150, 1124, 1103, 1049, 1031, 944, 838, 758, 708, 667
ESI-MS: 758.4 [M+NH$_4^+$]
HR-MS: 758.4892 ([M+NH$_4$]$^+$, C$_{39}$H$_{72}$NO$_{11}$Si$^+$, calculated: 758.4869), 799.4645 ([M+CH$_3$COO$^-$], C$_{41}$H$_{71}$O$_{13}$Si$^-$, calculated: 799.4669)
[α]$_D$: −32.6 (c=1.20, CHCl$_3$)
1H NMR (CHLOROFORM-d, 500 MHz): δ=7.34 (br. s, 1H), 7.29-7.24 (m, 2H), 7.10 (app. dt, J=6.7, 1.5 Hz, 1H), 5.51 (dd, J=10.8, 3.1 Hz, 1H), 5.02 (d, J=9.9 Hz, 1H), 4.82 (d, J=7.3 Hz, 2H), 4.81 (d, J=7.3 Hz, 1H), 4.64-4.70 (m, 3H), 4.59 (d, J=6.7 Hz, 1H), 4.28 (ddd, J=10.8, 3.8, 1.5 Hz, 1H), 3.94 (app. t, J=8.9 Hz, 1H), 3.64-3.70 (m, 2H), 3.62 (d, J=1.8 Hz, 1H), 3.58 (dd, J=9.4, 4.5 Hz, 1H), 3.52-3.56 (m, 2H), 3.49 (s, 3H), 3.40-3.46 (m containing a singlet, 3.42), 5H), 3.39 (s, 3H), 3.25 (dd, J=13.1, 4.1 Hz, 1H), 2.95 (dd, J=13.2, 11.2 Hz, 1H), 2.47-2.59 (m, 1H), 1.93-2.13 (m, 1H), 1.89 (d, J=11.0 Hz, 1H), 1.86 (d, J=11.3 Hz, 1H), 1.53-1.72 (m containing a doublet, 1.63), 6H), 1.45 (s, 3H), 1.40 (s, 3H), 1.31 (ddd, J=14.3, 9.5, 1.8 Hz, 2H), 1.15-1.24 (m, 1H), 0.82 (app. t, J=7.5 Hz, 3H), 0.76 (s, 9H), 0.00 (s, 3H), −0.01 (s, 3H)
$^{13}$C NMR (CHLOROFORM-d, 126 MHz): δ=169.5 (C), 146.4 (C), 136.9 (C), 133.8 (C), 129.6 (CH), 128.7 (CH), 128.0 (CH), 128.0 (CH), 125.0 (CH), 96.8 (CH$_2$), 96.8 (CH$_2$), 95.6 (CH$_2$), 80.3 (CH), 77.3 (CH), 75.1 (CH), 71.8 (CH$_2$), 71.7 (CH), 70.2 (CH$_2$), 66.6 (CH$_2$), 66.5 (CH), 59.0 (CH$_3$), 56.5 (CH$_3$), 55.8 (CH$_3$), 42.4 (C), 40.6 (CH$_2$), 40.0 (CH$_2$), 39.4 (CH), 38.3 (CH$_2$), 26.1 (CH$_3$), 25.7 (3CH$_3$), 24.9 (CH$_2$), 22.2 (CH$_3$), 18.2 (C), 17.7 (CH$_3$), 11.7 (CH$_3$), −4.1 (CH$_3$), −5.0 (CH$_3$)

4.10 Synthesis of Analogue J45

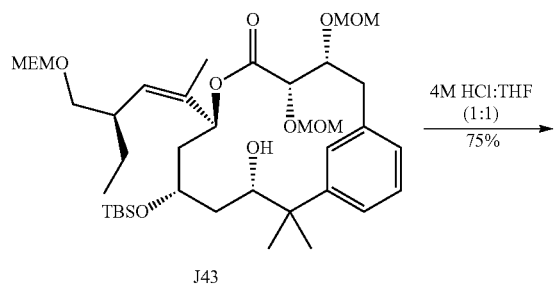

J43

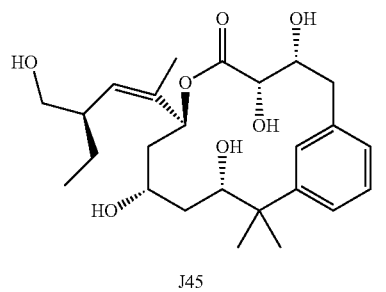

J45

To a cooled (0° C.) solution of J43 (9 mg, 12.1 μmol, 1.00 equivalent) in 3.6 ml THF was added aqueous HCl (4M, 3.6 ml). After stirring 15 h at room temperature, the mixture was diluted with 2 ml ethyl acetate, neutralized to pH 8 with sat. aq. NaHCO$_3$ and extracted with ethyl acetate (5×25 ml). The combined organic extracts were dried over MgSO$_4$ and concentrated in vacuo. The clear oil (16 mg) was purified by FC (SiO$_2$, hexane/acetone 6/4) to provide J45 (6 mg) as a white solid. HP-LC purification (LUNA C18, 0% to 100% acetonitrile in aqueous 5 nM ammonium acetate in 30 min) provided J45 (2.8 mg, 51%) as a white solid.

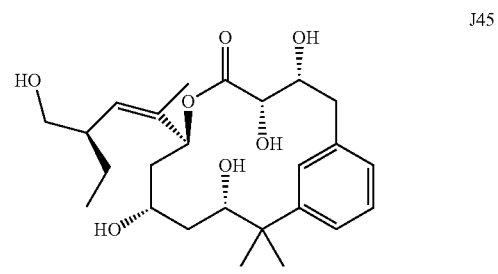 [SMILES: CC[C@H](/C=C(/C)[C@@H]1C[C@@H](O)C[C@H](O)C(C)(C)c2cccc(c2)C[C@@H](O)[C@H](O)C(=O)O1)CO]

J45

(3R,3'R,4S,7S,9R,11 S,Z)-3,4,9,11-tetrahydroxy-7-(3'-hydroxymethyl-1'-methylpent-1'-enyl)-12,12-dimethyl-6-oxabicyclo[11.3.1]heptadeca-1(17),13,15-trien-5-one Formula: C$_{25}$H$_{38}$O$_7$
Molar Mass: 450.57 g/mol
R$_f$: 0.08 (hexane/acetone 6/4)
ESI-MS: 451.2 [M+H$^+$], 433.2 [M−H$_2$O+H$^+$]
1H NMR (CHLOROFORM-d, 500 MHz): δ=7.35 (br. s, 1H), 7.16-7.26 (m, 2H), 7.05 (br. d, J=7.0 Hz, 1H), 5.48 (dd, J=10.4, 2.7 Hz, 1H), 4.93 (d, J=10.4 Hz, 1H), 4.34 (dd, J=11.7, 4.5 Hz, 1H), 4.14 (app. t, J=8.4 Hz, 1H), 3.43-3.52 (m, 3H), 3.14-3.30 (m, 2H), 2.74 (app. t, J=12.3 Hz, 1H), 2.26-2.67 (m, 6H), 1.76-1.91 (m, 2H), 1.57-1.71 (m containing a singlet, 1.67), 4H), 1.50 (s, 3H), 1.24-1.44 (m containing a singlet, 1.36), 5H), 1.04-1.17 (m, 1H), 0.83 ppm (app. t, J=7.4 Hz, 3H)
$^{13}$C NMR (CHLOROFORM-d, 126 MHz): δ=174.3 (C), 146.8 (C), 137.0 (C), 136.7 (C), 129.9 (CH), 129.0 (CH), 128.5 (CH), 127.8 (CH), 124.6 (CH), 76.1 (CH), 74.3 (CH), 73.9 (CH), 69.0 (CH), 67.0 (CH$_2$), 65.5 (CH), 42.7 (CH), 42.5 (C), 40.7 (CH$_2$), 39.6 (CH$_2$), 38.9 (CH$_2$), 26.4 (CH$_3$), 24.5 (CH$_2$), 20.3 (CH$_3$), 17.7 (CH$_3$), 11.9 (CH$_3$)

4.11 Synthesis of Alcohol J49

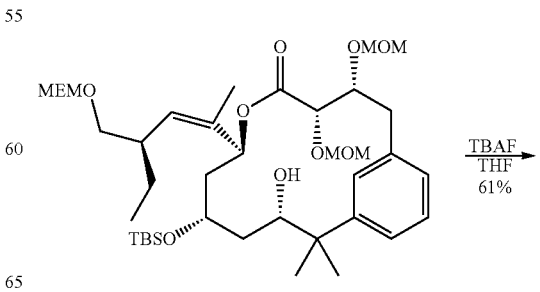

J43

4.12 Synthesis of Ketone J50

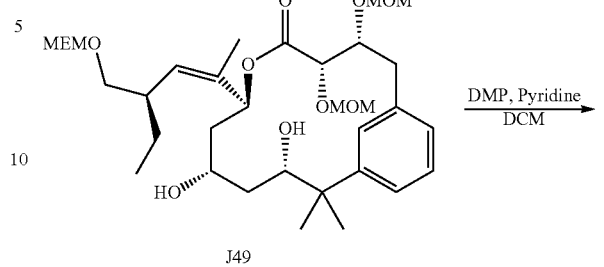

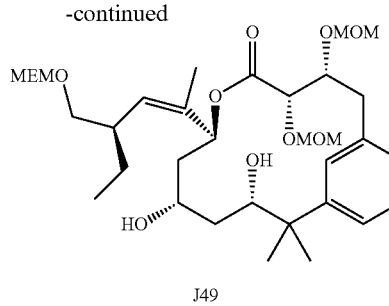

To a cooled (0° C.) solution of J43 (15 mg, 20.2 µmol, 1.00 equivalent) in 405 µl THF was added TBAF (1M in THF, 41 µl, 40.5 µmol, 2 equivalent). After stirring 2 h at room temperature, the mixture was concentrated and purified by FC (SiO$_2$, pentane/acetone 8/2) to provide J49 (7.7 mg, 61%) as a yellow oil.

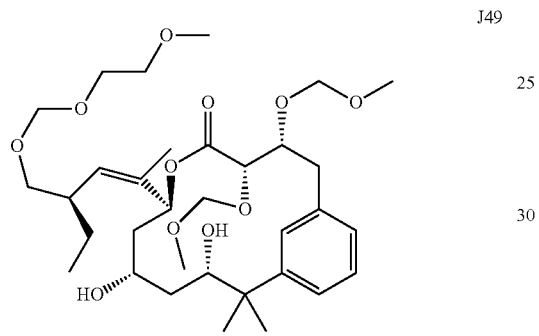

(3R,3'R,4S,7S,9R,11 S,Z)-9,11-dihydroxy-7-(3'-(2"-methoxyethoxymethoxymethyl)-1'-methylpent-1'-enyl)-2,3-bis(methoxymethoxy)-12,12-dimethyl-6-oxabicyclo[11.3.1]heptadeca-1(17),13,15-trien-5-one Formula: C$_{33}$H$_{54}$O$_{11}$
Molar Mass: 626.78 g/mol
R$_f$: 0.38 (pentane/acetone 7/3)
ESI-MS: 644.3 [M+NH$_4^+$]

$^1$H NMR (CHLOROFORM-d, 300 MHz): δ=7.38 (app. dt, J=7.9, 1.4 Hz, 1H), 7.21-7.32 (m, 2H), 7.16 (app. dt, J=7.5, 1.4 Hz, 1H), 5.46 (dd, J=10.2, 2.3 Hz, 1H), 4.99 (d, J=9.4 Hz, 1H), 4.89 (d, J=7.2 Hz, 1H), 4.84 (d, J=7.0 Hz, 1H), 4.67-4.73 (m, 2H), 4.64 (d, J=6.8 Hz, 1H), 4.61 (d, J=6.6 Hz, 1H), 4.17 (ddd, J=10.0, 5.3, 2.6 Hz, 1H), 4.01 (d, J=5.3 Hz, 1H), 3.80 (dd, J=5.9, 4.2 Hz, 1H), 3.61-3.75 (m, 2H), 3.35-3.59 (m (containing three singlets, 3.47, 3.42 and 3.39), 14H), 3.18 (dd, J=14.1, 2.4 Hz, 1H), 2.93 (dd, J=14.1, 10.2 Hz, 1H), 2.48-2.65 (m, 1H), 1.89 (ddd, J=14.5, 10.4, 2.4 Hz, 1H), 1.53-1.69 (m (containing a doublet, 1.62), 5H), 1.32-1.53 (m (containing two singlets, 1.44 and 1.43), 8H), 1.06-1.23 (m, 1H), 0.81 (app. t, J=7.5 Hz, 3H)

$^{13}$C NMR (CHLOROFORM-d, 75 MHz): δ=169.2 (C), 146.1 (C), 137.1 (C), 134.1 (C), 130.2 (CH), 128.5 (CH), 127.9 (CH), 127.6 (CH), 125.5 (CH), 96.6 (CH$_2$), 96.0 (CH$_2$), 95.6 (CH$_2$), 79.2 (CH), 78.0 (CH), 77.5 (CH), 71.8 (CH$_2$), 70.9 (CH$_2$), 70.8 (CH$_2$), 66.6 (CH$_2$), 65.9 (CH), 59.0 (CH$_3$), 56.1 (CH$_3$), 55.8 (CH$_3$), 42.3 (C), 41.3 (CH$_2$), 39.7 (CH), 38.7 (CH$_2$), 37.8 (CH$_2$), 26.6 (CH$_3$), 24.9 (CH$_2$), 24.2 (CH$_3$), 18.1 (CH$_3$), 11.9 (CH$_3$) ppm To a cooled (0° C.) solution of J49 (5.3 mg, 8.46 µmol, 1.00 equivalent) in 250 µl CH$_2$Cl$_2$ was added pyridine (3.4 µl, 42.3 µmom, 5.00 equivalent) and Dess-Martin periodinane (4 mg, 9.31 µmol, 1.10 equivalent). After stirring 40 min at room temperature, 1 ml sat. aq. Na$_2$S$_2$O$_3$ was added and stirred further for 90 min. The two-phase mixture was separated, extracted with ethyl acetate (3×2 ml), dried over MgSO$_4$ and concentrated. The ketone was used without further purification.

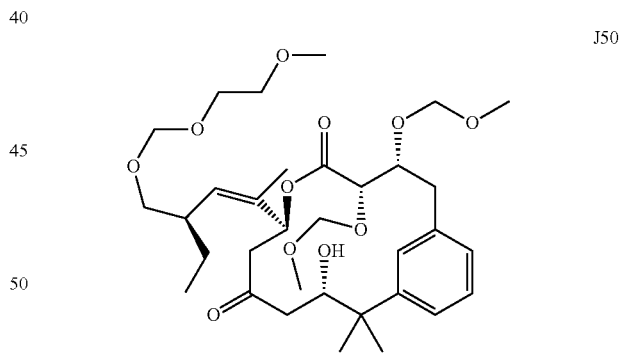

(3R,3'R,4S,7S,11 S,Z)-11-hydroxy-7-(3'-(2"-methoxyethoxymethoxymethyl)-1'-methylpent-1'-enyl)-2,3-bis(methoxymethoxy)-12,12-dimethyl-6-oxabicyclo[11.3.1]heptadeca-1(17),13,15-trien-5,9-dione Formula: C$_{33}$H$_{52}$O$_{11}$
Molar Mass: 624.76 g/mol
R$_f$: 0.26 (pentane/acetone 7/3)
ESI-MS: 642.3 [M+NH$_4^+$]

4.13 Synthesis of Analogue J51

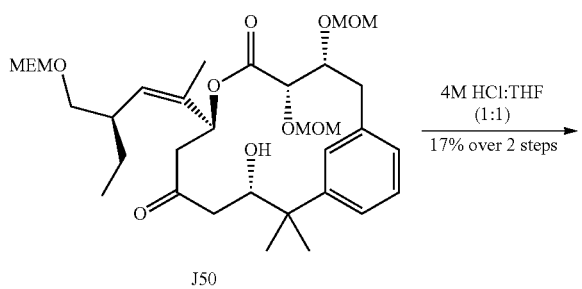

To a cooled (0° C.) solution of J50 (5 mg, 8.0 µmol, 1.00 equivalent) in 2.4 ml THF was added aqueous HCl (4M, 2.4 ml). After stirring 20 h at room temperature, the mixture was diluted with 1 ml ethyl acetate, neutralized to pH 8 with sat. aq. NaHCO$_3$ and extracted with ethyl acetate (5×15 ml). The combined organic extracts were dried over MgSO$_4$ and concentrated in vacuo. The residue was purified HP-LC purification (LUNA C18, 0% to 100% acetonitrile in aqueous 5 nM ammonium acetate in 30 min) provided J51 (0.6 mg, 17% over two steps) as a white solid.

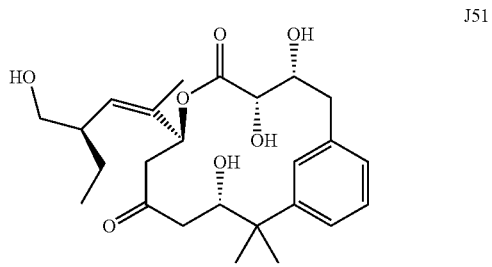 [SMILES: CC[C@H](/C=C(/C)[C@@H]1CC(=O)C[C@H](O)C(C)(C)c2cccc(c2)C[C@@H](O)[C@H](O)C(=O)O1)CO]

(3R,3'R,4S,7S,11 S,Z)-3,4,11-trihydroxy-7-(3'-hydroxymethyl-1'-methylpent-1'-enyl)-12,12-dimethyl-6-oxabicyclo[11.3.1]heptadeca-1(17),13,15-trien-5,9-dione Formula: O$_{25}$H$_{36}$O$_7$
Molar Mass: 448.55 g/mol
ESI-MS: 449.2 [M+H$^+$]
1H NMR (CHLOROFORM-d, 500 MHz): δ=7.33-7.39 (m, 1H), 7.28-7.32 (m, 1H), 7.14 (br. d, J=7.3 Hz, 1H), 7.01-7.05 (m, 1H), 5.40 (dd, J=8.7, 3.4 Hz, 1H), 5.01 (d, J=10.5 Hz, 1H), 4.17-4.25 (m, 2H), 3.62-3.66 (m, 1H), 3.54-3.60 (m, 1H), 3.29 (app. t, J=10.1 Hz, 1H), 3.21 (dd, J=13.4, 4.0 Hz, 1H), 2.88-2.93 (m, 2H), 2.75-2.82 (m, 1H), 2.71 (dd, J=18.3, 4.0 Hz, 1H), 2.35-2.45 (m, 1H), 2.30 (dd, J=18.3, 8.2 Hz, 1H), 2.04-2.12 (m, 1H), 1.67-1.76 (m (containing a doublet, 1.70), 4H), 1.57 (s, 3H), 1.47 (s, 3H), 1.33-1.42 (m, 1H), 1.05-1.17 (m, 1H), 0.83 ppm (app. t, J=7.5 Hz, 3H)

Example 5: Activity Tests of Phenyl Derivatives of Peloruside

Experimental Procedures:
Compounds

The test compound JC168 was dissolved in dimethyl sulfoxide (DMSO) at a concentration of 0.001, 0.01, 0.1 or 1 µg/ml.

The microtubule inhibitor paclitaxel was used as a positive control. It was dissolved in physiologic saline solution (at a concentration of 0.1 or 1 µg/ml).

Cell Lines
MO4 Cells:

As test cells for functional assays MO4 cells were used, which are murine virally transformed fibrosarcoma-like cells. This choice is based on the following elements. These cells:
1. are highly directionally motile and invasive both in vitro and in vivo
2. are sensitive to microtubule inhibitors, and survive the M-block.
3. are tumorigenic in C3H syngeneic mice.

MDA-MB231 GFP-LUC Cells:

Because MO4 cells do not invade when seeded on top of collagen, another cell line was used for performing the collagen invasion assay, namely MDA-MB232 GFP-LUC cells. These cells are derived from a human mammary carcinoma and were stably transfected with green fluorescent protein (GFP) and luciferase (LUC).

PtK2 Cells

The PtK2 cell line was established from the kidney tissue of an adult male rat kangaroo (*Potorous tridactylus*).

Functional Assays

The effect of the peloruside analog JC168 was tested on the following functional assays in vitro:
1. Immunocytochemistry of the Cytoplasmic Microtubule Complex Cells were seeded on glass coverslips in culture medium, supplemented with fetal bovine serum, at an initial concentration of 10,000/coverslip. After incubation overnight to allow spreading, treatments started at 37° C. for 1, 4 or 24 h. Cultures were then rinsed with phosphate-buffered saline and fixed in methanol at −20° C. The primary rabbit anti-tubulin polyclonal antibody was a gift from Dr. De Brabander (Janssen Life Sciences, Beerse, Belgium). Secondary antibodies were goat anti-rabbit, and revealed either with a chromogen or a fluorophor (Dako, Roskilde, Denmark).

2. Sulforhodamine B Assay

The sulforhodamine B (SRB) assay was used for cell density determination. The assay is based on the measurement of cellular protein content ("biomass"). The method allows a large number of samples to be tested within a few days, and is a quantitative assay for growth inhibition by microtubule inhibitors. The method has been optimized for the screening of compounds for growth effects on adherent cells in a 96-well format. After an incubation period, cell monolayers were fixed with 10% (wt/vol) trichloroacetic acid and stained for 30 min, after which the excess dye was removed by washing repeatedly with 1% (vol/vol) acetic acid. The protein-bound dye was dissolved in 10 mM Tris base solution for OD determination at 510 nm using a microplate reader. The results were linear over a 20-fold range of cell numbers, and the sensitivity was comparable to those of fluorometric methods.

3. MTT Assay

MTT (3-(4,5-Dimethylthiazol-2-yl)-2,5-diphenyltetrazolium bromide, a yellow tetrazole), was reduced to purple formazan in living cells. A solubilization solution (dimethyl sulfoxide) was added to dissolve the insoluble purple formazan product into a purple solution. The absorbance of this colored solution was quantified by measuring it at a wavelength between 500 and 600 nm by a spectrophotometer. The absorption maximum is dependent on the solvent employed. The reductions take place only when reductase enzymes are active, and therefore conversion is often used as a measure of viable (living) cells. However, it is important to keep in mind that other viability tests (such as the CASY cell counting technology) sometimes give different results, as many different conditions apart from growth interference can increase or decrease metabolic activity. As stated in another way, changes in metabolic activity can give large changes in MTT results, while the number of viable cells is constant. When the amount of purple formazan produced by cells treated with an agent is compared with the amount of formazan produced by untreated control cells, the effectiveness of the agent in causing death or in changing the metabolism of cells can be deduced through the production of a dose-response curve.

4. Collagen Type I Invasion Assay

Tissue invasion requires infiltration into an extracellular matrix (ECM) dominated by networks of collagen type I. The invasion model, presented here, consists of native, acid-extracted rat tail collagen type I containing nonhelical telopeptides situated at the N- and C-terminal ends. These telopeptides play an important role in intermolecular covalent cross-links necessary for a gel architecture presenting itself as a structural barrier to cancer cell traffic. Collagen type I solution was prepared with a final concentration of 1 mg ml$^{-1}$ collagen type I by mixing the following pre-cooled (stored at 4° C.) components: 4 volumes collagen type I (stock is 3.49 mg ml$^{-1}$), 5 volumes of calcium- and magnesium-free Hank's balanced salt solution (CMF-HBSS), 1 volume of minimal essential medium (MEM) (10×), 1 volume of 0.25 M NaHCO$_3$, 2.65 volumes of standard medium and 0.3 volumes of 1M NaOH to make the solution alkaline. The collagen type I solution was gently poured into the wells of a 6-well plate. The experimental set-up was placed at 37° C. in a humidified atmosphere with 10% CO2 in air for at least 1 h. After gelification, a cell suspension of MDA-MB231 GFP-LUC cells was added on top of the collagen gels and incubated for 24 hours. Invasion of cells was observed in the transparent 3D collagen gels by phase contrast microscopy as cells with extensions penetrating into the collagen gel (FIG. 5B-D). Invasion is calculated as the percentage of invading cells per high powered field and is expressed as the mean and standard deviation. The number of examined fields is 10. The sections were stained with hematoxylin-eosin.

5. Chick Heart Invasion Assay

Aggregates of MO4 cells were prepared by diluting single dissociated cells to appropriate concentrations in 6 ml complete growth medium in a 50 ml Erlenmeyer flask and incubated on a Gyrotory shaker at 37° C. and 70 rpm in a humidified atmosphere with 10% CO2 in air for 72 h. The aggregates were confronted overnight on top of semi-solid agar medium with precultured heart fragments (PHF, diameter 0.4 mm) prepared from 9-day-old chick embryos. Suspension organotypic cultures were incubated in 1.5 ml culture medium with or without a test compound on a Gyrotory shaker at 120 rpm under a controlled atmosphere containing 10% CO2 in air. Cells were fixed in Bouin-Hollande's solution and embedded in paraffin for histologic determination of cell invasiveness. Consecutive sections were stained with haematoxylin-eosin. Invasion is defined as the progressive occupation of PHF by the confronting test cells. Microscopic analysis of all consecutive sections from a confronting culture allowed the reconstruction of the interaction between the cell aggregate and the PHF in three dimensions.

The observation of different patterns of interaction has led to the following scale:

Grade 0: Only PHF is found. No confronting cells can be observed.

Grade I: The confronting test cells are attached to the PHF, and do not occupy the heart tissue, even not the outermost cell layers.

Grade IIa: Occupation of the PHF is limited to the outer fibroblast-like and myoblast cell layers Grade IIb: The PHF has surrounded the cell aggregate without signs of occupation.

Grade III: The confronting cells have occupied the PHF, but have left more than half of the original amount of heart tissue intact.

Grade IV: The confronting cells have occupied more than half of the original volume of the PHF.

Grade I and II are observed with non-invasive cell populations, while grade III an IV are typical of invasion. To evaluate progression with time, histological analysis was done on confronting cultures fixed after different incubation periods.

Results:

1. Immunocytochemistry of the Cytoplasmic Microtubule Complex

PtK2 cells were treated with DMSO (solvent control), JC168, or paclitaxel (positive control). After 1 hour, 4 hours, and 24 hours of incubation, cells were fixed and stained for the cytoplasmic microtubule complex.

TABLE 1

Effects of JC168 and paclitaxel on the cytoplasmic microtubule complex.

| Treatment | Concentration (µg/ml) | 1 hour | 4 hours | 24 hours |
|---|---|---|---|---|
| DMSO | — | normal | normal | normal |
| JC168 | 0.1 | disturbed | disturbed | disturbed |
|  | 1.0 | disturbed | disturbed | disturbed |
| paclitaxel | 0.1 | normal | disturbed | disturbed |
|  | 1.0 | disturbed | disturbed | disturbed |

JC168-treated PtK2 cells showed a disturbed microtubule complex similar to paclitaxel-treated cells. The unordered cytoplasmic microtubule complex was already observed after 1 hour of incubation with JC168.

2. Sulforhodamine B Assay

MO4 cells were treated with DMSO (solvent control), JC168, or paclitaxel. After 4 days of incubation, a sulforhodamine B assay was performed to evaluate the effect of the treatments on cell growth.

Figure 2:
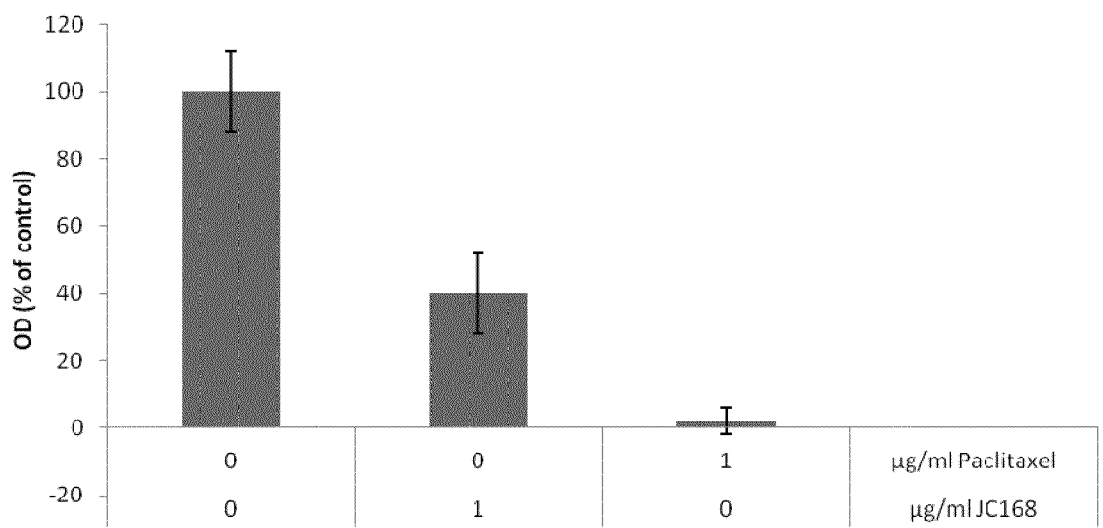
FIG. 2: Comparison of JC168 and paclitaxel to inhibit cell growth. MO4 cells were treated with dimethyl sulfoxide (DMSO, solvent control), 1 μg/ml JC168 or 1 μg/ml paclitaxel for 4 days. After said 4 days of incubation the cells were fixed and stained with sulforhodamine B to determine cellular protein content. Excess dye was removed by washing. Protein-bound dye was dissolved and optical density was measured. Data represent optical density (OD) as a percentage of solvent control (mean and standard deviation, n=6).

FIG. 1 shows that JC168 inhibits cell growth. The potency of JC168 is 5% as compared to paclitaxel (FIG. 2).

3. MTT Assay

MO4 cells were treated with DMSO (solvent control), JC168, or paclitaxel. After 4 days of incubation, a MTT assay was performed to evaluate the effect of the treatments on the viability of the cells, in particular their metabolic activity, more in particular their dehydrogenase activity.

Figure 3:
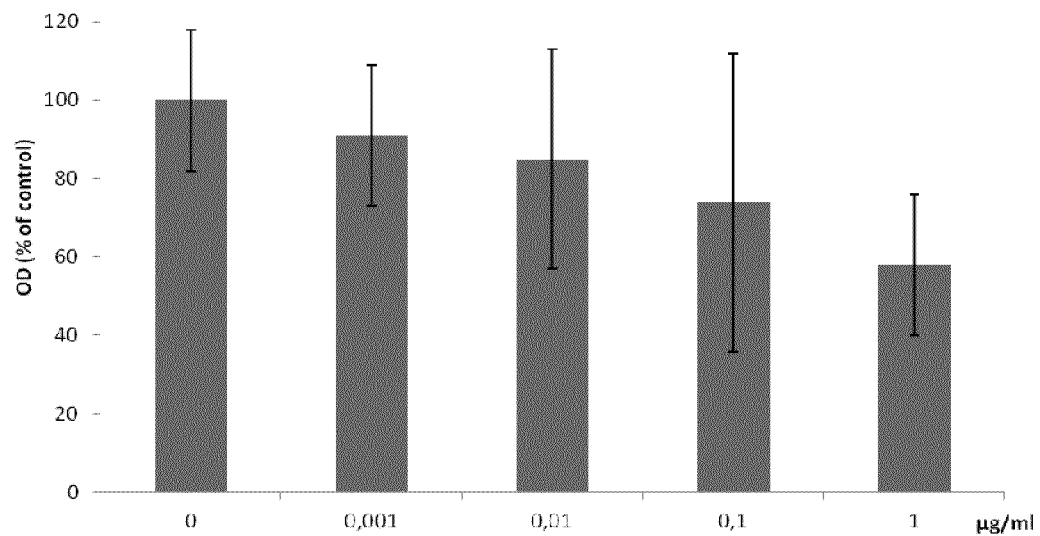
FIG. 3: JC168 inhibits MTT conversion. MO4 cells were treated with dimethyl sulfoxide (DMSO, solvent control), 0.001, 0.01, 0.1 or 1 μg/ml JC168 for 4 days. Then, 3-(4,5-dimethylthiazol-2-yl)-2,5-diphenyltetrazolium bromide was added and the cultures were incubated to allow the cells to reduce the MTT into formazan. The formazan was dissolved and optical density was measured. Data represent optical density (OD) as a percentage of solvent control (mean and standard deviation, n=6).

FIG. 3 shows that JC168 inhibits the conversion of 3-(4,5-dimethylthiazol-2-yl)-2,5-diphenyltetrazolium bromide (MTT) into formazan. This reduction in metabolic activity of jc163-treated MO4 cells is mainly due to the growth-inhibiting effect of jc163 as revealed by the SRB assay (FIGS. 1-2).

Figure 4:
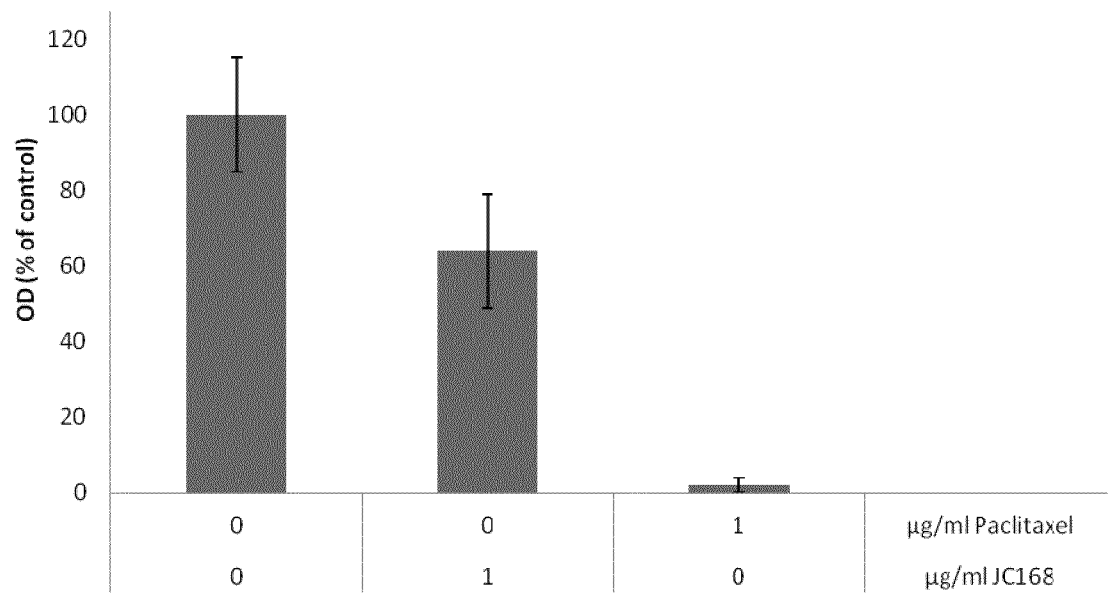
FIG. 4: Comparison of JC168 and paclitaxel to inhibit MTT conversion. MO4 cells were treated with dimethyl sulfoxide (DMSO, solvent control), 1 μg/ml JC168 or 1 μg/ml paclitaxel for 4 days. Then, 3-(4,5-dimethylthiazol-2-yl)-2,5-diphenyltetrazolium bromide was added and the cultures were incubated to allow the cells to reduce the MTT into formazan. The formazan was dissolved and optical density was measured. Data represent optical density (OD) as a percentage of solvent control (mean and standard deviation, n=6).

The potency of jc163 to inhibit MTT conversion is 3% as compared to paclitaxel (FIG. 4).

4. Collagen Invasion Assay

Figure 5:
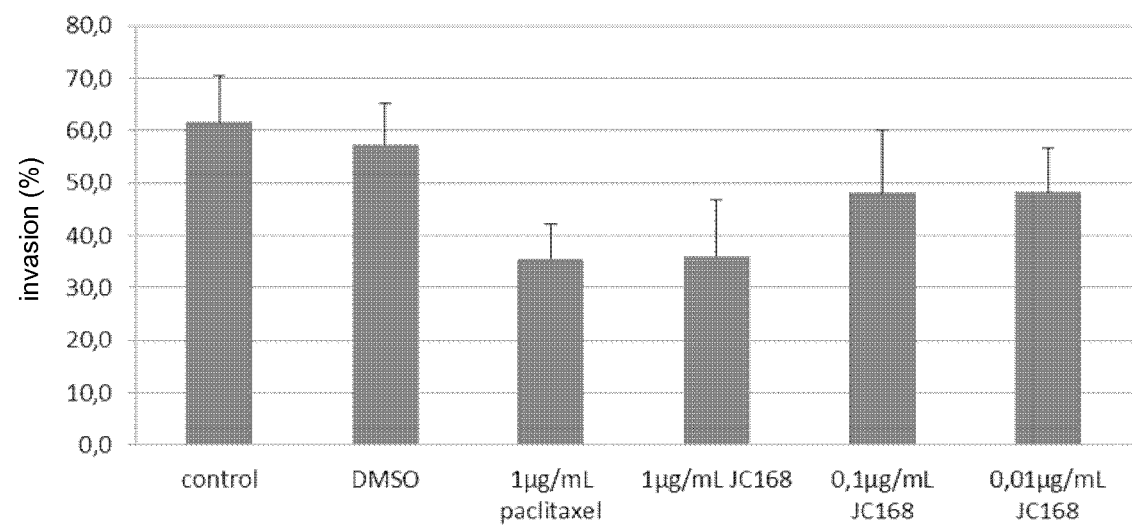
FIG. 5: JC168 inhibits invasion of MDA-MB231 GFP-LUC cells into collagen type I. Single cell suspensions of MDA-MB231 GFP-LUC cells were incubated on top of a collagen type I gel in the absence (control) or presence of DMSO (solvent control), 1 μg/ml paclitaxel, or 0.01, 0.1 or 1 μg/ml JC168 for 24 hours. Invading cells were counted by phase-contrast microscopy as cells with extensions penetrating into the gel. (A) Invasion was calculated as the percentage of invading cells per high powered field (mean and standard deviation, n=10). Microphotographs of representative cultures of MDA-MB231 GFP-LUC cells treated with DMSO (B), 1 μg/ml JC168 (C), and 1 μg/ml paclitaxel (D) after 24 hours of incubation on top of a collagen type I gel. Scalebar=100 μm.
Figure 5:
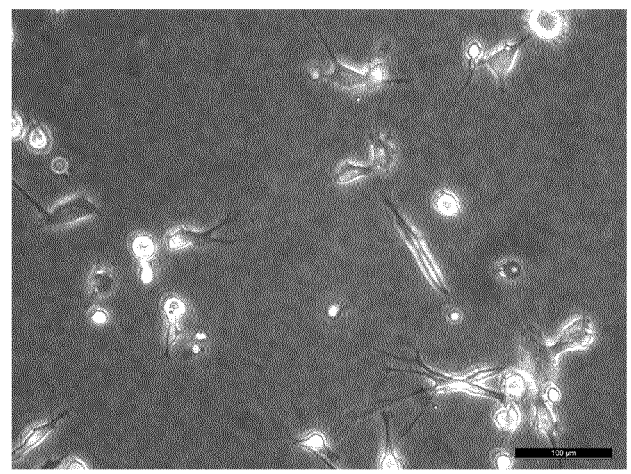
Figure 5:
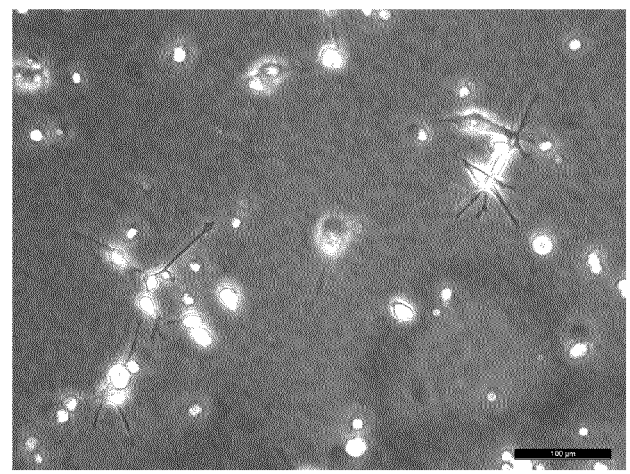
Figure 5:
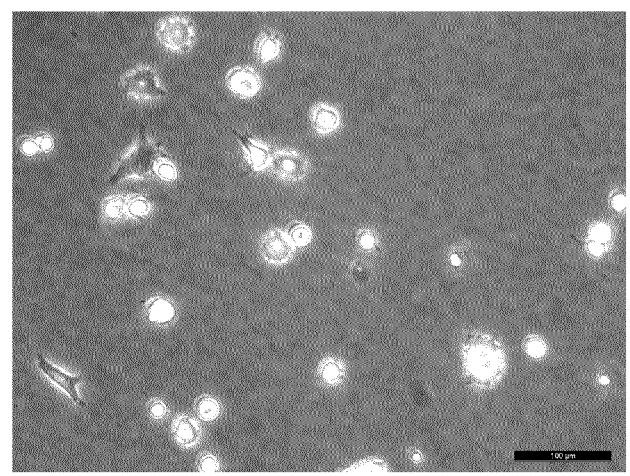

MDA-MB231 GFP-LUC cells were treated with DMSO (solvent control), JC168, or paclitaxel (positive control) or left untreated (control) and incubated on a collagen type I gel. After 24 hours of incubation, invasion into the collagen was evaluated by phase-contrast microscopy. JC168 inhibits invasion of MDA-MB231 GFP-LUC cells into collagen type I as shown in FIG. 5. The potency of JC168 to inhibit invasion in collagen type I is 89% as compared to paclitaxel. The histological sections of the collagen gels after 14 days show a low number of cells on top of the gel for the paclitaxel and JC168 treatments, whereas for the solvent control numerous cells are found on top of and in the collagen gel. From this we can conclude that the number of invaded cells is clearly lower in the treated cultures.

5. Chick Heart Invasion Assay

MO4 cells were confronted with precultured heart fragments and the organotypic cultures were incubated in suspension in the presence of DMSO (solvent control), JC168 or paclitaxel (positive control) for 2-4 days.

TABLE 2

Effect of JC168 (1 μg/ml) and paclitaxel (1 μg/ml) on invasion of MO4 cells into embryonic chick heart. n = number of organotypic cultures classified according to the indicated scale.

| Incubation time | treatment | Grade I | Grade II | Grade III | Grade IV |
|---|---|---|---|---|---|
| 2 days | DMSO | | n = 5 | | |
|  | JC168 | n = 5 | | | |
| 3 days | DMSO | | | n = 2 | n = 3 |
|  | JC168 | | n = 5 | | |
| 4 days | DMSO | | | | n = 5 |
|  | JC168 | | n = 3 | n = 3 | |
| 4 days | DMSO | | | | n = 5 |
|  | paclitaxel | | n = 5 | | |

JC168 inhibits invasion of MO4 cells into embryonic chick heart tissue, but is less potent in inhibiting invasion as compared to paclitaxel (Table 2).

Example 6: Testing Pharmacological Efficacy

In order to evaluate the usefulness of the peloruside analog as a microtubule inhibitor, following additional experiments are performed for the compounds as defined herein:

(1) Test tube experiments to determine the binding affinity between the compound and its molecular target.
(2) Functional tests in vitro to assess the effects of the compound on growth, directional migration and invasion of malignant cell populations. Proposed assays are: (2a) Growth curve determinations via cell counts, sulforhodamine B biomass and MTT conversion measurements. (2b) Directional migration analysis via Boyden chamber and wound healing assays. (2c) Invasion assays in Matrigel, type I collagen gel and embryonic chick heart fragments.
(3) Evaluation of the assays mentioned in (2) on different cell types: mammary, prostate, ovarian, colorectal, lung, melanoma and epidermoid carcinoma as representatives of the most important human cancers, and fibroblasts, myofibroblasts and endothelial cells as representatives of stromal cells.
(4) Functional tests in laboratory nude mice to assess the effect on growth, invasion and metastasis formation. Proposed assays are: (4a) Assessment of growth, invasion, metastasis and angiogenesis of fluorescently labeled tumor cells in the chick chorio-allantois membrane test. (4b) Volume measurements of heterotopically (subcutaneously) implanted tumor cells. (4c) Histology evaluation of invasion by orthotopically implanted cancer cells. (4d) Metastasis analysis of luciferase-transfected tumor cells (injected intracardially) via bioluminescence detection.

The invention claimed is:
1. A compound of Formula I:

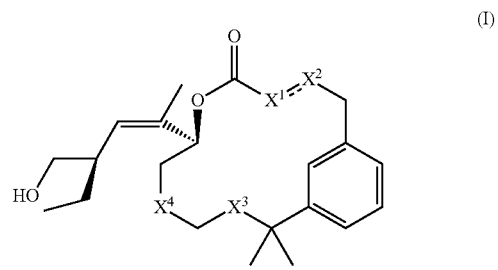

(I)

wherein:
$X^1$ is $CR^{1a}R^{1b}$, $X^2$ is $CR^{2a}R^{2b}$, $X^3$ is $CR^{3a}R^{3b}$, $X^4$ is $CR^{4a}R^{4b}$, and wherein:

$R^{1a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy;

$R^{2a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{3a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy $R^{4a}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy; and
wherein:

$R^{1b}$ is selected from hydrogen, hydroxyl, halogen, and a group selected from $-NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{2b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{3b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group being independently optionally substituted with one or more substituent(s) each independently selected from hydroxyl, halogen, $C_{1-6}$alkyl and $C_{1-6}$alkoxy, $R^{4b}$ is selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl-$C_{1-6}$alkyl and $C_{1-6}$alkoxy, each group independently being independently optionally substituted with one or more substituent(s) each independently selected from hydroxyl, halogen, $C_{1-6}$alkyl and $C_{1-6}$alkoxy;

or wherein $R^{1a}$ and $R^{1b}$, or $R^{2a}$ and $R^{2b}$, or $R^{3a}$ and $R^{3b}$, or $R^{4a}$ and $R^{4b}$ taken together represent an oxo (=O) group; and wherein the bond represented by a dashed and solid line represents a single bond or a double bond and wherein in case of a double bond, $R^{1b}$ and $R^{2b}$ are absent and at least one of $R^{1a}$ and $R^{2a}$ is not OH or —$NR^{10}R^{11}$; and wherein:

$R^{10}$ and $R^{11}$ are each independently selected from hydrogen and $C_{1-6}$alkyl; and wherein:

when $R^{1a}$, $R^{2a}$, $R^{3a}$ or $R^{4a}$ is hydroxyl, the corresponding $R^{1b}$, $R^{2b}$, $R^{3b}$ or $R^{4b}$ is not hydroxyl, is not —$NR^{10}R^{11}$, is not halogen, or is not $C_{1-6}$alkoxy, when $R^{1a}$, $R^{2a}$, $R^{3a}$ or $R^{4a}$ is —$NR^{10}R^{11}$, the corresponding $R^{1b}$, $R^{2b}$, $R^{3b}$ or $R^{4b}$ is not hydroxyl, is not —$NR^{10}R^{11}$, is not halogen, or is not $C_{1-6}$alkoxy, when $R^{1a}$, $R^{2a}$, $R^{3a}$ or $R^{4a}$ is halogen, the corresponding $R^{1b}$, $R^{2b}$, $R^{3b}$ or $R^{4b}$ is not hydroxyl, or is not —$NR^{10}R^{11}$, when $R^{1b}$, $R^{2b}$, $R^{3b}$ or $R^{4b}$ is hydroxyl, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy, and when $R^{1b}$, $R^{2b}$, $R^{3b}$ or $R^{4b}$ is —$NR^{10}R^{11}$, the corresponding $R^{1a}$, $R^{2a}$, $R^{3a}$ or $R^{4a}$ is not hydroxyl, is not —$NR^{10}R^{11}$, is not halogen, or is not $C_{1-6}$alkoxy, when $R^{1b}$, $R^{2b}$, $R^{3b}$ or $R^{4b}$ is halogen, the corresponding $R^{1a}$, $R^{2a}$, $R^{3a}$ or $R^{4a}$ is not hydroxyl, or is not —$NR^{10}R^{11}$, and the stereoisomers, prodrugs, tautomers, racemates, salts, hydrates, or solvates thereof.

2. The compound according to claim 1, wherein $R^{1b}R^{2b}R^{3b}$, and $R^{4b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy; or wherein $R^{1a}$ and $R^{1b}$, and/or $R^{2a}$ and $R^{2b}$, and/or $R^{3a}$ and $R^{3b}$, and/or $R^{4a}$ and $R^{4b}$ taken together form an oxo (=O) group.

3. The compound according to claim 1, having structural Formula Ia,

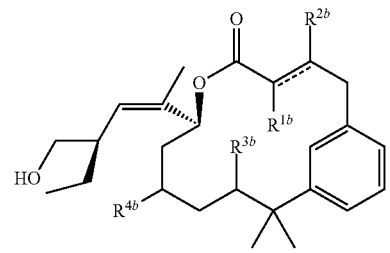

(Ia)

wherein $R^{1b}$, $R^{2b}$, $R^{3b}$, and $R^{4b}$ are each independently selected from hydrogen, hydroxyl, halogen, and a group selected from —$NR^{10}R^{11}$, $C_{1-6}$alkyl, $C_{2-6}$alkenyl, $C_{2-6}$alkynyl, $C_{6-10}$aryl, $C_{6-10}$aryl$C_{1-6}$alkyl and $C_{1-6}$alkoxy, each group independently being optionally substituted with one or more substituent(s) each independently selected from hydroxyl, halogen, $C_{1-6}$alkyl and $C_{1-6}$alkoxy;

$R^{1b}$ and $R^{2b}$ each independently can represent an oxo (=O) group, in which case the bond represented by a dashed and solid line is a single bond and the geminal hydrogen is absent;

$R^{3b}$ and $R^{4b}$ each independently can represent an oxo (=O) group, in which case the geminal hydrogen is absent; and wherein when the bond represented by a dashed and solid line is a double bond with E- or Z-geometry, at least one of $R^{1b}$ and $R^{2b}$ is not hydroxyl or —$NR^{10}R^{11}$;

and the stereoisomers, prodrugs, tautomers, racemates, salts, hydrates, or solvates thereof.

4. The compound according to claim 3, having structural Formula Ib, Ic or Id,

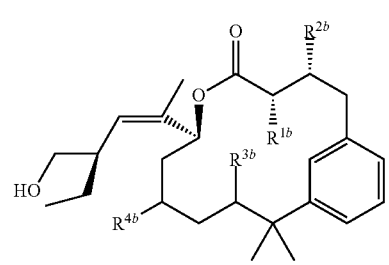

(Ib)

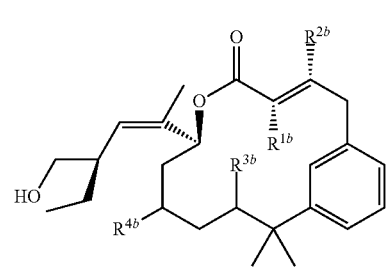

(Ic)

-continued (Id)

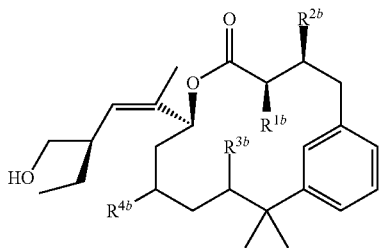

wherein $R^{1b}$, $R^{2b}$, $R^{3b}$, and $R^{4b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy; or wherein $R^{1a}$ and $R^{1b}$, and/or $R^{2a}$ and $R^{2b}$, and/or $R^{3a}$ and $R^{3b}$, and/or $R^{4a}$ and $R^{4b}$ taken together form an oxo (=O) group, and wherein in structure Ic, the double bond can have the E- or Z-geometry.

5. The compound according to claim 3, having structural Formula Ie, If, or Ig, (Ie)

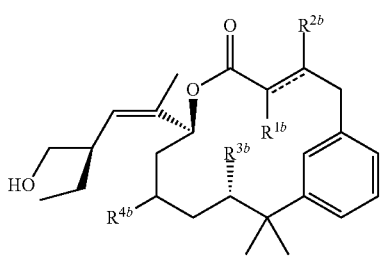

(If)

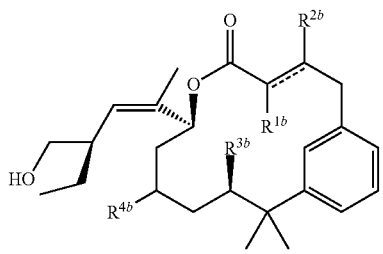

(Ig)

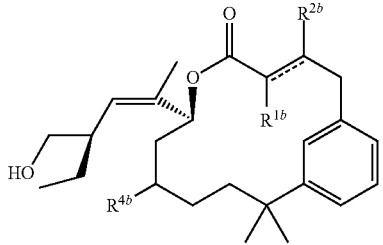

wherein $R^{1b}$, $R^{2b}$, $R^{3b}$, and $R^{4b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy; or wherein $R^{1a}$ and $R^{1b}$, and/or $R^{2a}$ and $R^{2b}$, and/or $R^{3a}$ and $R^{3b}$, and/or $R^{4a}$ and $R^{4b}$ taken together form an oxo (=O) group, and the stereoisomers, prodrugs, tautomers, racemates, salts, hydrates, or solvates thereof.

6. The compound according to claim 3, having structural Formula Ih, Ii or Ij, (Ih)

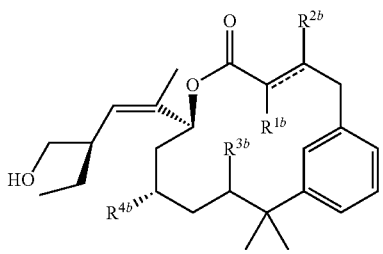

(Ii)

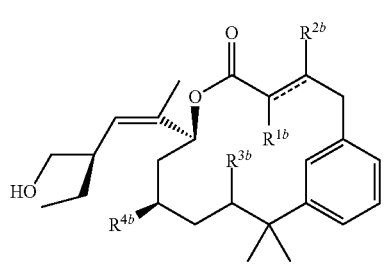

(Ij)

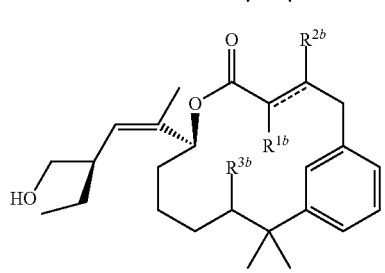

wherein $R^{1b}$, $R^{2b}$, $R^{3b}$, and $R^{4b}$ each independently are selected from hydrogen, halogen, and a group selected from $C_{1-6}$alkyl, $C_{2-6}$alkenyl, $C_{2-6}$alkynyl, $C_{6-10}$aryl, $C_{6-10}$aryl$C_{1-6}$alkyl, and $C_{1-6}$alkoxy, each group being optionally substituted with one or more substituent(s) selected from hydroxyl, halogen, $C_{1-6}$alkyl, or $C_{1-6}$alkoxy; or wherein $R^{1a}$ and $R^{1b}$, and/or $R^{2a}$ and $R^{2b}$, and/or $R^{3a}$ and $R^{3b}$, and/or $R^{4a}$ and $R^{4b}$ taken together form an oxo (=O) group, and the stereoisomers, prodrugs, tautomers, racemates, salts, hydrates, or solvates thereof.

7. The compound according to claim 1, wherein $R^{3b}$ and $R^{4b}$ have an anti-stereorelationship.

8. The compound according to claim 1, wherein $R^{1b}$ and $R^{2b}$ are each independently selected from hydrogen, hydroxyl, —NR$^{10}$R$^{11}$, halogen, $C_{1-6}$alkyl, and $C_{1-6}$alkoxy, or wherein $R^{1b}$ is hydroxyl and $R^{2b}$ is methoxy or vice versa, or wherein $R^{1b}$ is halogen and $R^{2b}$ is methoxy, or vice versa, or wherein $R^{1b}$ is halogen and $R^{2b}$ is hydroxyl, or vice versa, or wherein $R^{1b}$ and $R^{2b}$ are halogen, or wherein $R^{1b}$ and $R^{2b}$ are methoxy, or wherein $R^{1b}$ and $R^{2b}$ are hydroxyl.

9. The compound according to claim 1, wherein $R^{3b}$ is selected from hydrogen, hydroxyl, —$NR^{10}R^{11}$, halogen, $C_{1-6}$alkyl, and $C_{1-6}$alkoxy, or wherein $R^{3b}$ is hydroxyl, methoxy or halogen.

10. The compound according to claim 1, wherein $R^{4b}$ is selected from the group consisting of hydrogen, hydroxyl, —$NR^{10}R^{11}$, halogen, $C_{1-6}$alkyl, and $C_{1-6}$alkoxy, or wherein $R^{4b}$ is hydroxyl, methoxy or halogen.

11. The compound according to claim 1, having one of the following structural formulas:

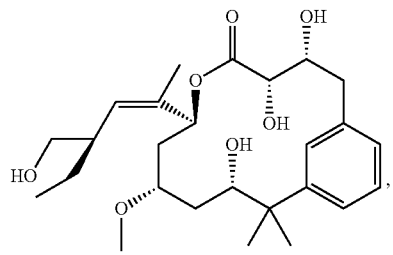,

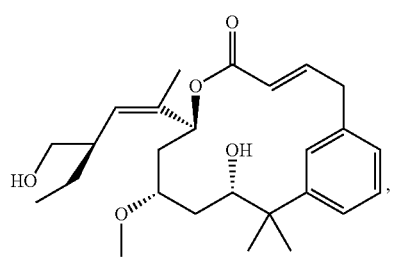,

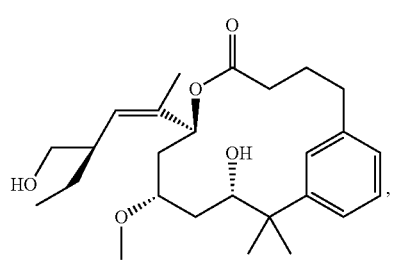,

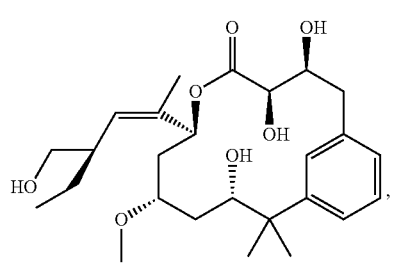,

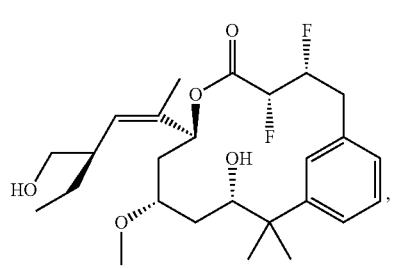,

-continued

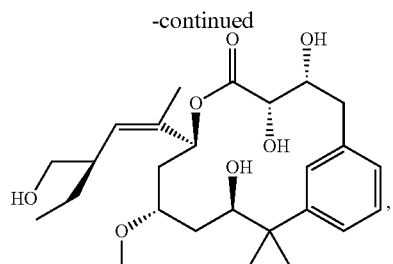,

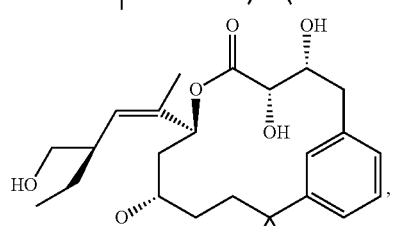,

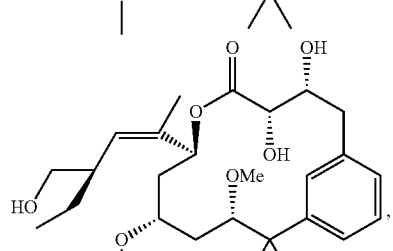,

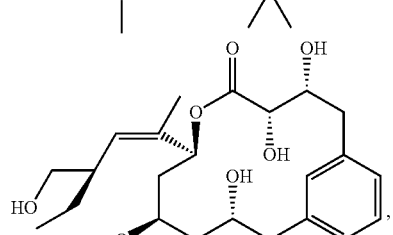,

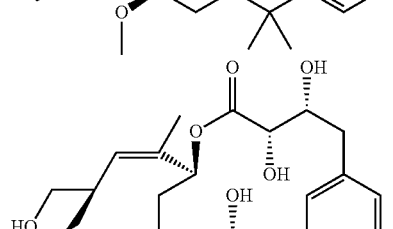,

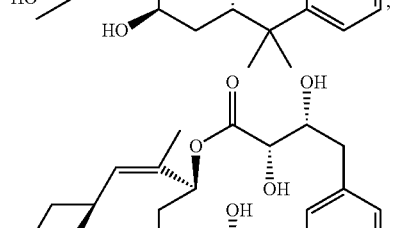,

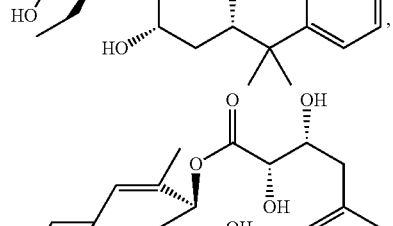,

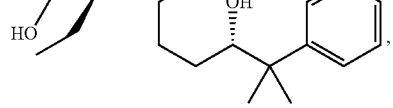

-continued

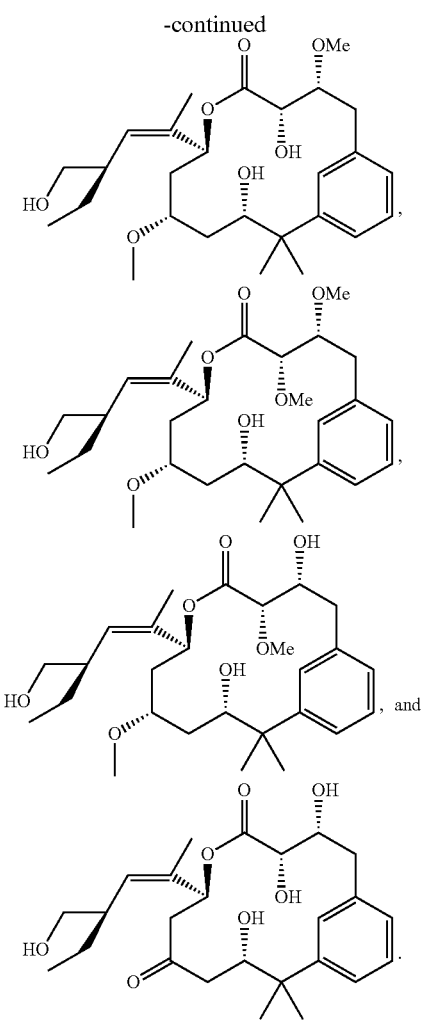

12. A composition comprising a compound according to claim 1, and a pharmaceutically acceptable excipient, and optionally comprising a further active pharmaceutical ingredient.

13. The compound according to claim 1, for use as a medicament.

14. A method of therapeutically treating a proliferative disorder selected from the group consisting of breast cancer, prostate cancer, ovarian cancer, colorectal cancer, lung cancer, melanoma, and epidermoid carcinoma, in a subject in need of such treatment, comprising administering to said subject a therapeutically effective amount of the compound according to claim 1.

15. A process for producing a compound according to claim 1, comprising the steps of:
(a) reacting a methyl ketone having structural Formula IIa with an aldehyde having structural Formula IIb, through aldol coupling, wherein $P^4$ and $P^5$ are protecting groups, and executing suitable functional group interconversions, thereby obtaining a compound having structural Formula II;
(b) protecting the functional groups at positions $X^3$ and $X^4$ in the compound of Formula II where needed;
(c) reacting the compound of Formula II with a compound of the Formula III in the presence of a suitable catalyst, giving rise to a compound of the formula (IV), (d) removing the protecting groups $P^1$ and $P^4$ in the resulting compound and esterifying the deprotected COOH with the $C_{is}$ OH group, executing suitable functional group interconversions, thereby obtaining the lactone having structural Formula V; and (e) deprotecting $P^5$ in the compound having structural Formula V and deprotecting any of the possibly protected $X^1$, $X^2$, $X^3$, or $X^4$ groups, if required after executing additional suitable functional group interconversions, thereby obtaining a compound having structural Formula I:

(IIa)

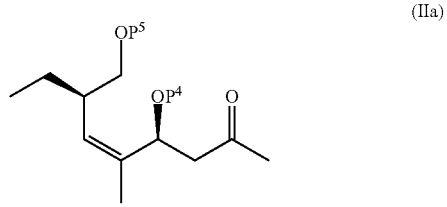

(IIb)

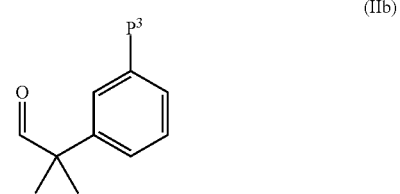

(II)

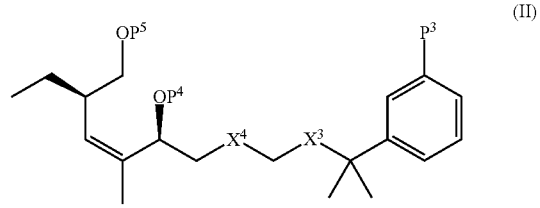

(III)

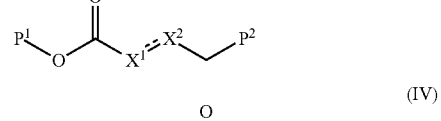

(IV)

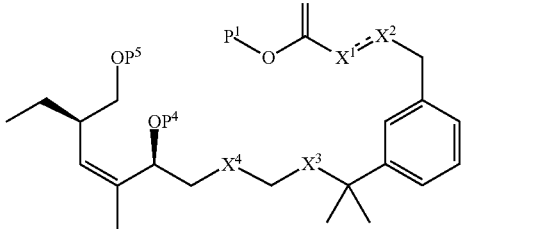

(V)

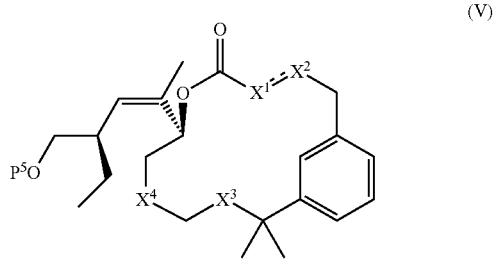

-continued

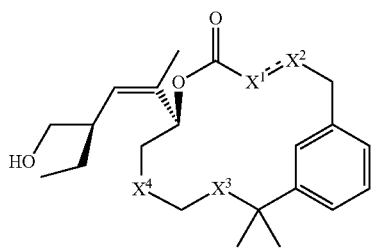

(I)

wherein
P¹ is hydrogen or a carboxyl protecting group;
P² is selected from halogen, pseudohalogen, CF₃SO₃ and OAc, and, simultaneously, P³ is a trialkyltin, or P³ is boronic acid or a boronic ester;
or, alternatively, wherein
P² is a trialkyltin, or P² is boronic acid or a boronic ester, and simultaneously, P³ is selected from halogen, pseudohalogen, CF₃SO₃ and OAc;
P⁴ is selected from an orthogonally chosen protecting group;
P⁵ is a protecting group which can be orthogonally removed;

the catalyst is a transition metal with ligands; and
X¹, X², X³, and X⁴ have the same meaning as that defined in claim 1, and wherein, if present, their functional groups are suitably protected in steps (a) and (b), functionally interconverted where needed and deprotected accordingly in step (e).

16. The compound according to claim 8, wherein $R^{1b}$ and $R^{2b}$ are hydrogen, halogen, hydroxyl or methoxy.

17. The method according to claim 14, wherein the proliferative disorder is non-small cell lung cancer.

18. The method according to claim 14, wherein the proliferative disorder is Kaposi's sarcoma.

19. The process according to claim 15, wherein
P¹ is an optionally substituted alkyl;
P² is bromo, and simultaneously P³ is trimethyltin or tri-n-butyltin;
or, alternatively, wherein
P² is trimethyltin or tri-n-butyltin, and simultaneously P³ is bromo;
P⁴ is 4-OMe-Bn;
P⁵ is a protecting group selected from: TBS and MEM; and
the catalyst is Pd₂(dba)₃.CHCl₃.

20. The process according to claim 15, wherein P¹ is methyl.

* * * * *